(12) United States Patent
Axt et al.

(10) Patent No.: US 6,436,919 B1
(45) Date of Patent: Aug. 20, 2002

(54) LOCAL ANESTHETIC COMPOUNDS

(75) Inventors: Sabine M. Axt, Sunnyvale; Timothy J. Church, San Mateo; John R. Jacobsen, San Francisco; Thomas E. Jenkins, La Honda; Yu-Hua Ji, Redwood City; Huiwei Wu, Foster City, all of CA (US)

(73) Assignee: Theravance Inc., South San Francisco, CA (US)

( * ) Notice: Subject to any disclaimer, the term of this patent is extended or adjusted under 35 U.S.C. 154(b) by 0 days.

(21) Appl. No.: 09/671,630

(22) Filed: Sep. 28, 2000

Related U.S. Application Data

(60) Provisional application No. 60/157,368, filed on Oct. 1, 1999.

(51) Int. Cl.[7] .................... C07D 413/06; C07D 413/14; A61K 31/517; A61P 23/02

(52) U.S. Cl. .................... 514/183; 514/258; 540/467

(58) Field of Search ................ 540/467; 514/183, 514/258

(56) References Cited

U.S. PATENT DOCUMENTS

| | | | |
|---|---|---|---|
| 3,984,555 A | 10/1976 | Amschler et al. | 424/251 |
| 4,597,903 A | 7/1986 | Gokel et al. | 260/330.6 |
| 4,687,844 A | * 8/1987 | Gokel et al. | 540/467 |
| 5,134,232 A | 7/1992 | Tsien et al. | 540/467 |
| 5,389,630 A | 2/1995 | Sato et al. | 514/218 |
| 5,405,975 A | 4/1995 | Kuhn et al. | 548/347 |
| 5,948,906 A | 9/1999 | Tsien et al. | 540/467 |

FOREIGN PATENT DOCUMENTS

| | | |
|---|---|---|
| EP | 292365 A2 * | 11/1988 |
| WO | 99/51565 | 10/1999 |

OTHER PUBLICATIONS

Ager, I.R., et al. "Synthesis and Central Nervous System Activity of Quinazolones Related to 2–Methyl–3–(o–tolyl)–4(3H)–quinazolone (Methaqualone)," *J. Med. Chem.* 20(3): 379–386 (1977).

(List continued on next page.)

*Primary Examiner*—Mukund J. Shah
*Assistant Examiner*—Thomas McKenzie
(74) *Attorney, Agent, or Firm*—David E. Boone; Jeffrey A. Hagenah

(57) ABSTRACT

This invention is directed to novel local anesthetic compounds, pharmaceutical compositions containing these compounds, methods of use and methods of preparing these compounds. In one embodiment, the compounds are of the following formula:

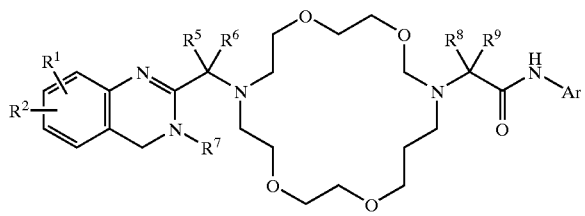

wherein: $R^1$ and $R^2$ are independently selected from the group consisting of hydrogen, alkyl, halo, cyano, hydroxy, alkoxy, amino, monosubstituted or disubstituted amino, carboxy, and alkoxycarbonyl; $R^5$ and $R^6$ are independently selected from the group consisting of hydrogen and alkyl; $R^7$ is alkyl, substituted alkyl, aryl, substituted aryl, heteroaryl, substituted heteroaryl, heterocycle, or substituted heterocycle; $R^8$ and $R^9$ are independently selected from the group consisting of hydrogen, alkyl, substituted alkyl and NRaRb-where Ra and Rb are alkyl; and Ar is selected from the group consisting of aryl, substituted aryl, heteroaryl, substituted heteroaryl, heterocycle, substituted heterocycle, cycloalkyl and substituted cycloalkyl; or a pharmaceutically acceptable salt thereof. The compounds find use as local anesthetics.

13 Claims, 11 Drawing Sheets

OTHER PUBLICATIONS

Database Chemcats 'Online! Chemical Abstracts, Columbus, Ohio, US. AN 2000: 927662, Aug. 23, 1999.

Debnath, A.K., et al. "Structure–Based Identification of Small Molecule Antiviral Compounds Targeted to the gp41 Core Structure of the Human Immunodeficiency Virus Type I." *J. Med. Chem.* 42: 3203–3209 (1999).

Gatto, et al. "Synthesis and Binding Properties of Bibracchial Lariat Ethers (BiBLEs): Survey of Synthetic Methods and Cation Selectivites." *J. Org. Chem.* 51: 5373–5384 (1986).

Gupta, C.M., et al. "Drugs Acting on the Central Nervous System. Syntheses of Substituted Quinazolones and Quinazolines and Triazepino– and Traizocinoquinazolones." *J. Med. Chem.* 11(2): 392–395 (1968).

Hollowood, J., et al. "Local Anesthetics with Enhanced Affinity for Proteins." *J. Med. Chem.* 10(5): 863–867 (1967).

Kuzma, P.J., et al. "Progress in the Development of Ultra–Long–Acting Local Anesthetics." *Regional Anesthesia.* 22(6): 543–551 (1997).

Padia, J.K., et al. "Design and Synthesis of Novel Nonpeptide CCK–B Receptor Antagonists." *Bioorg. & Med. Chem. Letts.* 7(7): 805–810 (1997).

Vogtle, F., et al. "Kronenether mit haptophoren bzw. pharmakophoren Gruppen." *Chem. Ber.* 111: 1434–1439 (1978). (summary in English).

Yamashita, T., et al. "Synthesis of Crown Ether Dyes." *Bull. Chem. Soc. Jpn.* 53: 1550–1554 (1980).

* cited by examiner

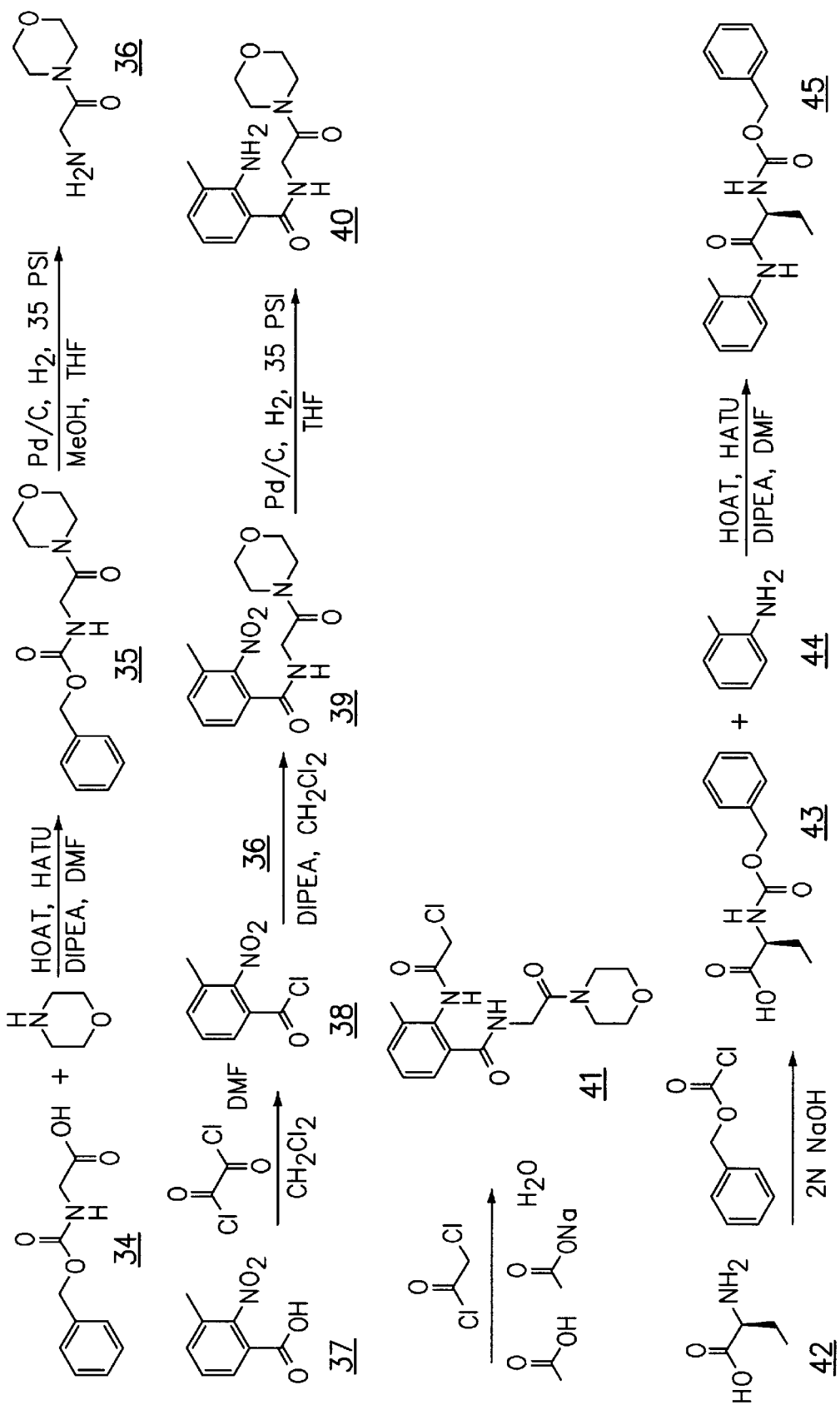
FIG. 1-A

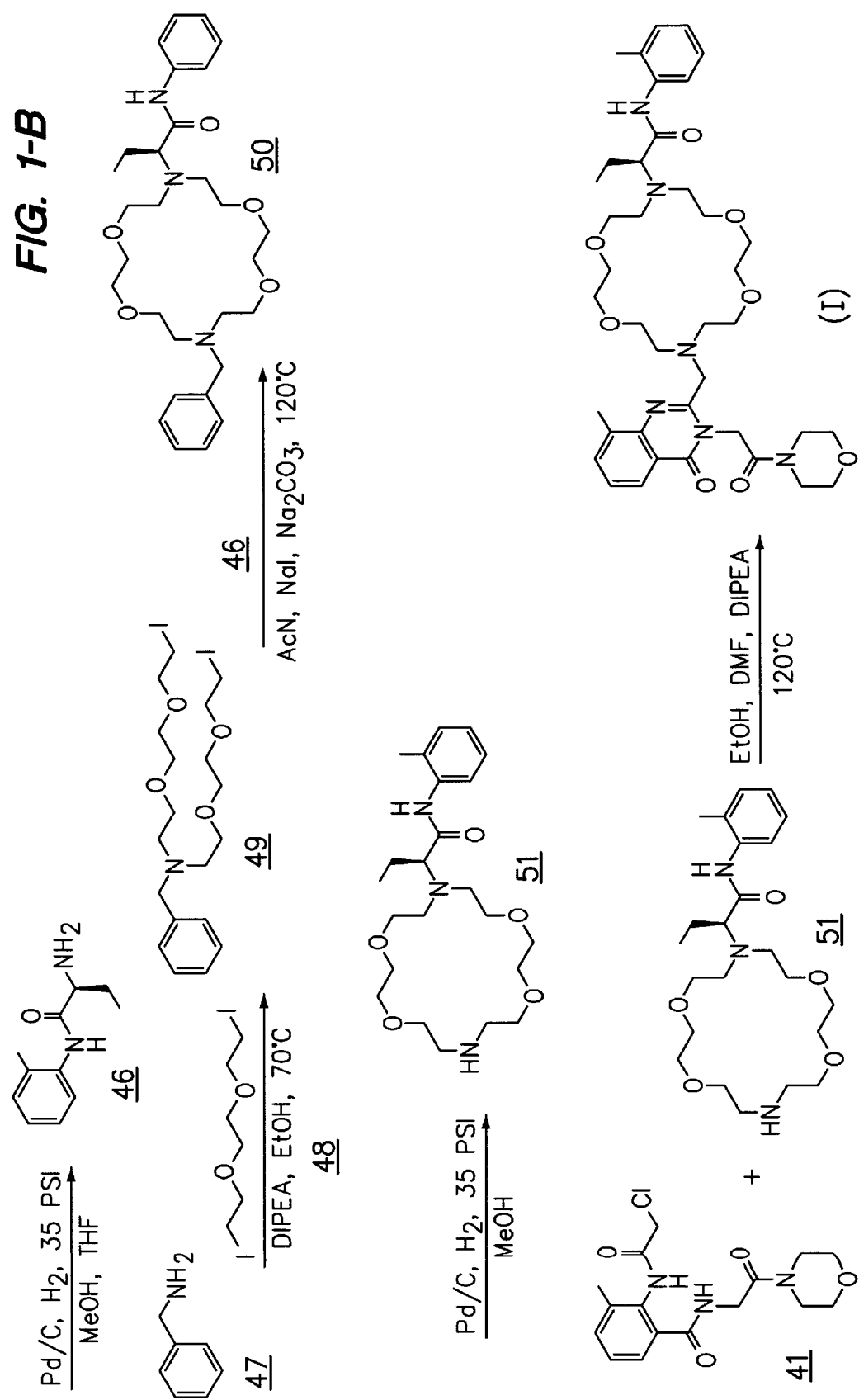
FIG. 1-B

FIG. 2
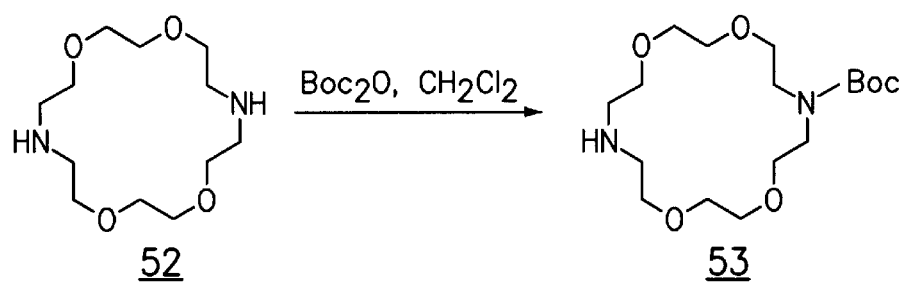
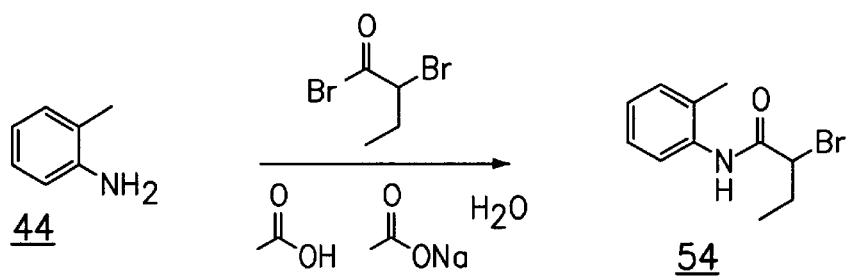
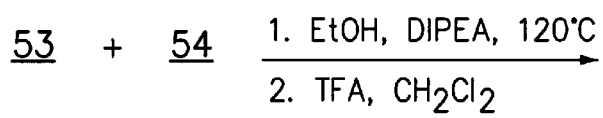
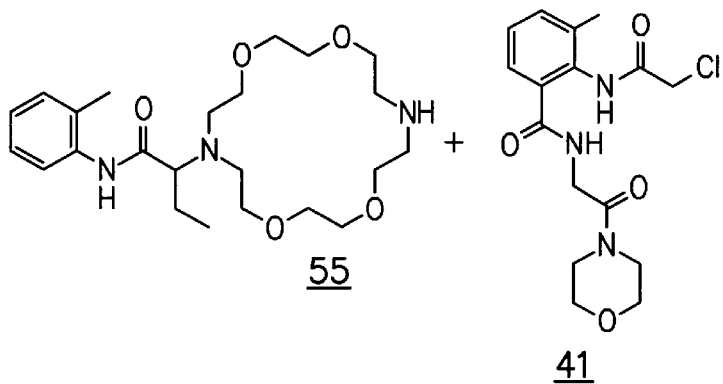
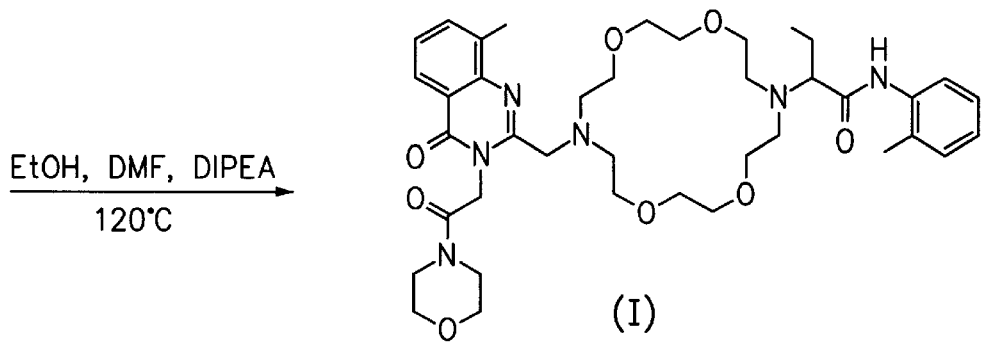

FIG. 6
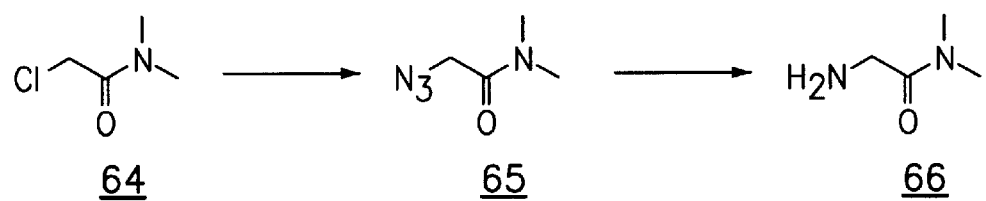
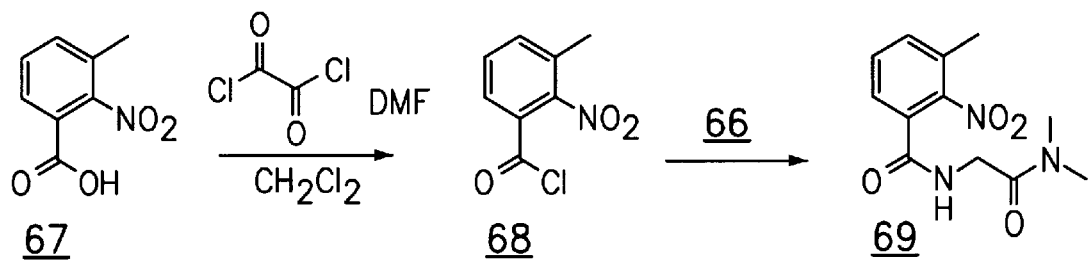
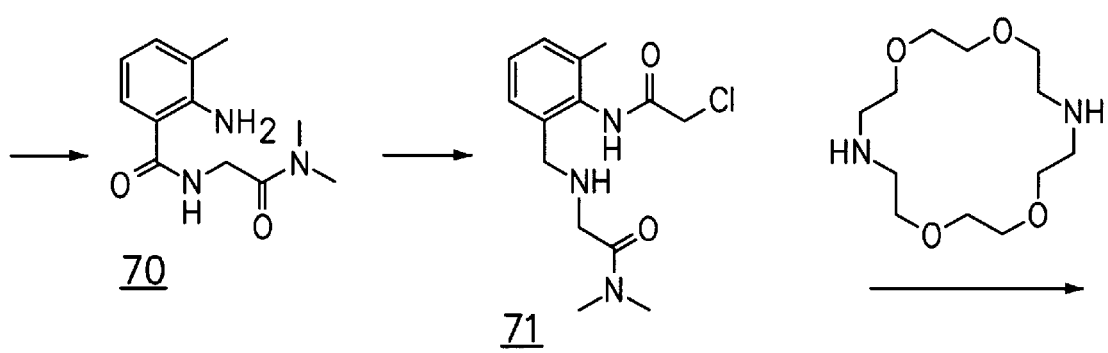
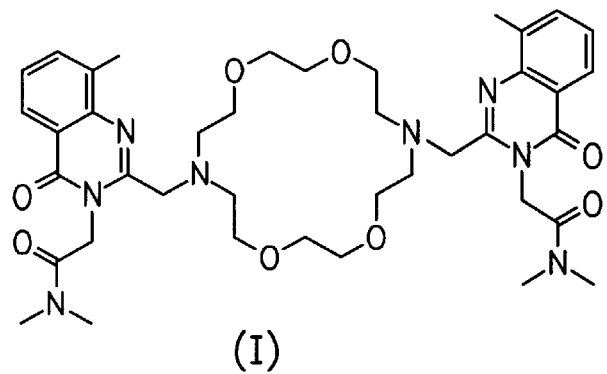
(I)

FIG. 10
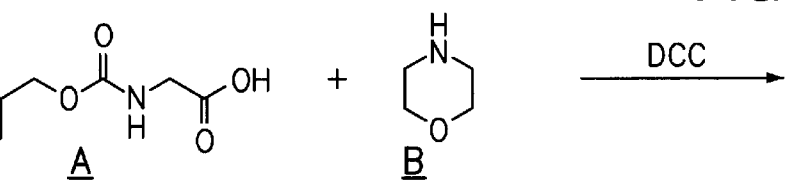
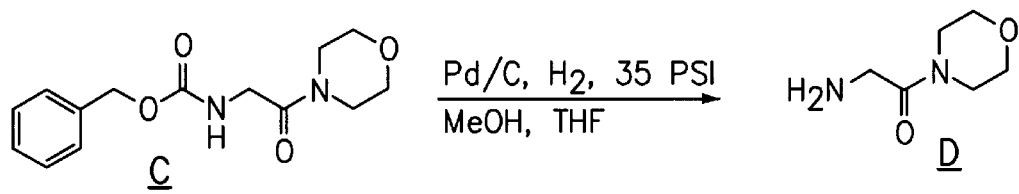
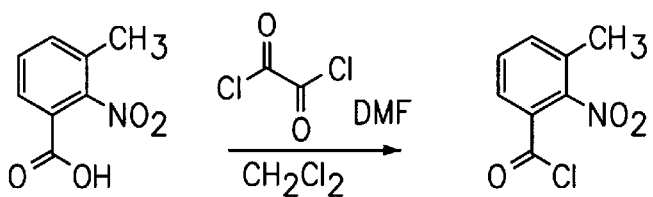
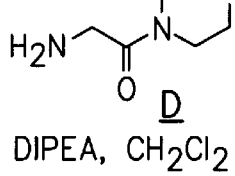
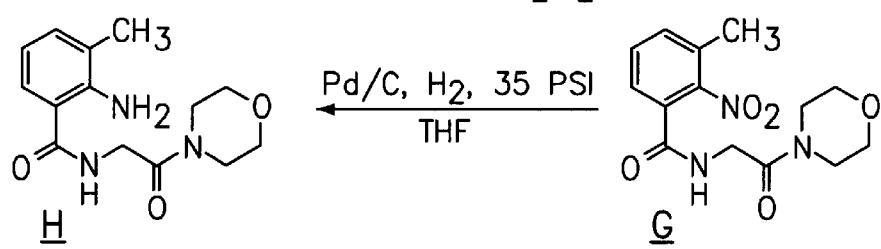
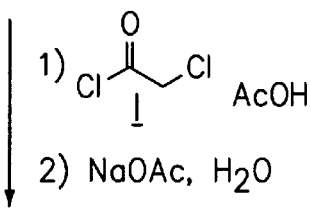
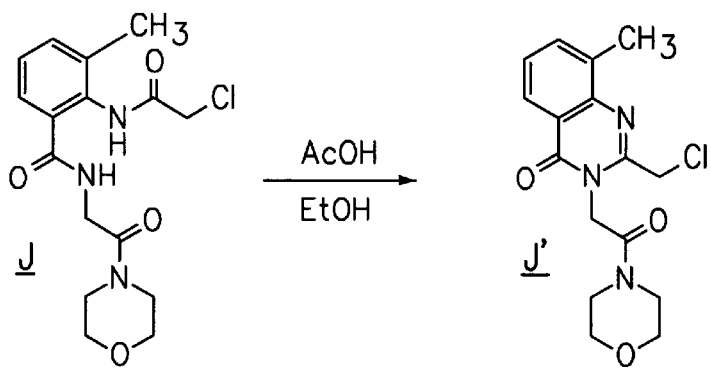

LOCAL ANESTHETIC COMPOUNDS

CROSS-REFERENCE TO RELATED APPLICATIONS

This application claims the benefit of U.S. Provisional Application 60/157,368, filed on Oct. 1, 1999, the disclosure of which is incorporated herein by reference in its entirety.

BACKGROUND OF THE INVENTION

1. Field of the Invention

This invention is directed to novel local anesthetic compounds, pharmaceutical composition containing these compounds, methods of use and methods for preparing these compounds.

2. State of the Art

Local anesthetics are believed to prevent or relieve pain by interrupting nerve conduction. More specifically, such compounds are believed to a specific receptor site within the pore of the sodium channels in the nerves and block ion movement through this pore. Currently, a number of local anesthetics such as benzocaine, bupivacaine, cocaine, lidocaine, mepivacaine are available and are being used as to prevent or relieve pain. However, these drugs have limited utility as they cause adverse side effects such as cardiotoxicity and CNS side effects and/or have short duration of action. Accordingly, there is a need for local anesthetics that have longer duration of action while reducing the undesired side effects.

The compounds of the present invention fulfill this need.

SUMMARY OF THE INVENTION

This invention provides novel compounds that are useful as inhibitors of $Na^+$ channels and are effective as local anesthetics.

Accordingly, in one aspect, this invention is directed to a compound of Formula (I):

$$L_1\text{-}X\text{-}L_2 \quad (I)$$

wherein:

$L_1$ is represented by:
(i) a group of formula (a):

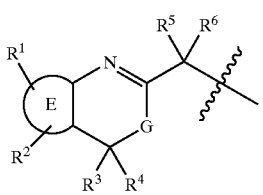

(a)

where:
E is aryl, heteroaryl, heterocycle, or cycloalkyl;
G is —$NR^7$— (where $R^7$ is hydrogen, alkyl, substituted alkyl, aryl, substituted aryl, heteroaryl, substituted heteroaryl, heterocycle, or substituted heterocycle), —O— or —S(O)n— (where n is 0, 1 or 2);
$R^1$ and $R^2$ are independently selected from the group consisting of hydrogen, alkyl, halo, cyano, hydroxy, alkoxy, amino, —$NR^cR^d$ (where $R^c$ is hydrogen or alkyl and $R^d$ is alkyl), carboxy, and carboxyalkyl; or $R^1$ and $R^2$ when adjacent to each other together form —$OCH_2O$— or —$O(CH_2)_2O$—;

$R^3$ and $R^4$ are independently selected from the group consisting of hydrogen, alkyl, halo, cyano, hydroxy, alkoxy, amino, —$NR^cR^d$ (where $R^c$ is hydrogen or alkyl and $R^d$ is alkyl), carboxy, and alkoxycarbonyl; or $R^3$ and $R^4$ together with the carbon atom to which they are attached form a carbonyl group;
$R^5$ and $R^6$ are independently selected from the group consisting of hydrogen and alkyl; or
(ii) a group of formula (b):

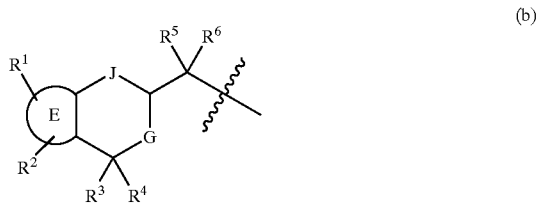

(b)

wherein:
J is —O—, or —S(O)n— (where n is 0, 1, or 2); and
E, G, $R^1$, $R^2$, $R^3$, $R^4$, $R^5$ and $R^6$ are as defined above;
X is a linker;
$L_2$ is represented by:
(iii) a group of formula (c):

(c)

wherein:
Ar is selected from the group consisting of aryl, substituted aryl, heteroaryl, substituted heteroaryl, heterocycle, substituted heterocycle, cycloalkyl and substituted cycloalkyl;
W is selected from a covalent bond, —$[CR^8R^9]_r$—, —$[CR^8R^9]_r$—C(O)—, —OC(O)—$[CR^8R^9]_r$—, —C(O)O$[CR^8R^9]_r$—, —O—$[CR^8R^9]_rC(O)$—, —C(O)—NH—$[CR^8R^9]_r$—, or —NH—C(O)$[CR^8R^9]_r$ where r is an integer of 0 to 10, and $R^8$ and $R^9$ are independently selected from the group consisting of hydrogen, alkyl, substituted alkyl and —$NR^aR^b$— where $R^a$ and $R^b$ are both alkyl; or
(iv) a group of formula (d):

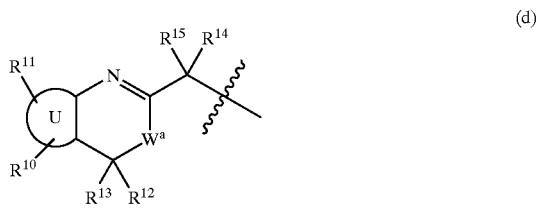

(d)

where:
U is aryl, heteroaryl, heterocycle, or cycloalkyl;
$W^a$ is —$NR^{16}$— (where $R^{16}$ is hydrogen, alkyl, substituted alkyl, aryl, substituted aryl, heteroaryl, substituted heteroaryl, heterocycle, or substituted heterocycle), —O— or —S(O)n— (where n is 0, 1 or 2);
$R^{10}$ and $R^{11}$ are independently selected from the group consisting of hydrogen, alkyl, halo, cyano, hydroxy, alkoxy, amino, monosubstituted or disubstituted amino, carboxy, and carboxyalkyl; or $R^{10}$ and $R^{11}$ when adjacent to each other together form —OCH$_2$O— or —O(CH$_2$)$_2$O—;

$R^{12}$ and $R^{13}$ are independently selected from the group consisting of hydrogen, alkyl, halo, cyano, hydroxy, alkoxy, amino, monosubstituted or disubstituted amino, carboxy, and alkoxycarbonyl; or $R^{12}$ and $R^{13}$ together with the carbon atom to which they are attached form a carbonyl group;

$R^{14}$ and $R^{15}$ are independently selected from the group consisting of hydrogen and alkyl; or (v) a group of formula (e):

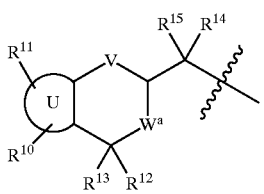

(e)

where:
V is —O—, or —S(O)n$^1$— (where n$^1$ is 0, 1, or 2); and

U, W$^a$, $R^{10}$, $R^{11}$, $R^{12}$, $R^{13}$, $R^{14}$ and $R^{15}$ are as defined above; and individual isomers, mixtures of isomers, prodrugs, and pharmaceutical acceptable salts thereof provided that:

when L$_1$ is a group of formula (a) wherein E is phenyl, R$^1$ is methyl and is at the 8-position of the quinazolone ring, R$^2$, R$^5$, R$^6$ are hydrogen, G is —NR$^7$— where R$^7$ is morpholin-1-ylcarbonylmethyl; X is 1,4,10,13-tetraoxa-7,16-diazacyclooctadec-7,16-diyl; L$_2$ is Ar—W— where W is methylene, then Ar is not phenyl and is named as 7-[8-methyl-3-(morpholin-4-ylmethyl]-4-(3H)-quinazolinon-2-yl)methyl-16-[(R)-(2-benzyl)]-1,4,10,13-tetraoxa-7,16-diazacyclooctadecane; and when L$_1$ is a group of formula (a) wherein E is phenyl, R$^1$ is methyl and is at the 8-position of the quinazolone ring, R$^2$, R$^5$, R$^6$ are hydrogen, G is —NR$^7$— where R$^7$ is tetrahydropyran-4-ylaminocarbonylmethyl; X is 1,4,10,13-tetraoxa-7,16-diazacyclooctadec-7,16-diyl; L$_2$ is Ar—W— where W is —NH—C(O)[CHCH$_2$CH$_3$]—, then Ar is not 2-methylphenyl and is named as 7-[8-methyl-3-(tetrahydropyran-4-ylaminocarbonylmethyl]-4-(3H)-quinazolinon-2-yl)methyl-16-[(R)-(2-methylphenylaminocarbonyl)prop-1-yl]-1,4,10,13-tetraoxa-7,16-diazacyclooctadecane.

Preferably, the linker X is a group of the formula:

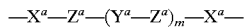

wherein:
m is an integer of from 0 to 20;
X$^a$ at each separate occurrence is selected from the group consisting of —O—, —S—, —NR—, —N$^+$RR'—, —C(O)—, —C(O)O—, —C(O)NR—, —C(S), —C(S)O—, —C(S)NR— and a covalent bond where R and R' as defined below;
Z$^a$ at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, substituted arylene, substituted heteroarylene, substituted heterocyclene, and a covalent bond;

each Y$^a$ at each separate occurrence is selected from the group consisting of —O—, —C(O)—, —OC(O)—, —C(O)O—, —NR—, —S(O)n—, —C(O)NR'—, —NR' C(O)—, —NR'—C(O)NR'—, —NR' C(S) NR'—, —C(=NR')—NR'—, —NR'—C(=NR')—, —OC(O)—NR'—, —NR'—C(O)—O—, —P(O)(OR')—O—, —O—P(O)(OR')—, —S(O)$_n$CR'R''—, —S(O)$_n$—NR'—, —NR'—S(O)$_n$—, —S—S—, and a covalent bond; where n is 0, 1 or 2; and R, R' and R'' at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, substituted aryl, heteroaryl, substituted heteroaryl, heterocyclic, and substituted heterocyclic provided that at least one of X$^a$, Z$^a$, and Y$^a$ is not a covalent bond.

In a second aspect, this invention is directed to a pharmaceutical composition comprising a pharmaceutically acceptable excipient and a therapeutically effective amount of a compound of Formula (I) or a pharmaceutically acceptable salt thereof.

In a third aspect, this invention is directed to a method for producing local anesthesia in a mammal which method comprises administering to a mammal in need of such treatment a pharmaceutical composition comprising a pharmaceutically acceptable excipient and a therapeutically effective amount of a compound of Formula (I) or a pharmaceutically acceptable salt thereof.

In a fourth aspect, this invention is directed to a method for modulating the activity of a Na$^+$ channel in a mammal, which method comprises administering to said mammal a Na$^+$ channel modulating amount of a compound of Formula (I) or a pharmaceutically acceptable salt thereof.

In a fifth aspect, this invention is directed to the use of a compound of Formula (I) or a pharmaceutically acceptable salt thereof in the preparation of a medicament. Preferably the medicament is used for producing local anesthesia in a mammal.

In a sixth aspect, this invention is directed to processes for preparing compounds of Formula (I).

In a seventh aspect, this invention is directed to novel intermediates useful or preparing compounds of Formula (I) or pharmaceutically acceptable salts hereof.

BRIEF DESCRIPTION OF THE DRAWINGS

FIGS. 1A–11 illustrate synthetic procedures for preparing the compounds of this invention.

DETAILED DESCRIPTION OF THE INVENTION

Definitions

Figure 3:
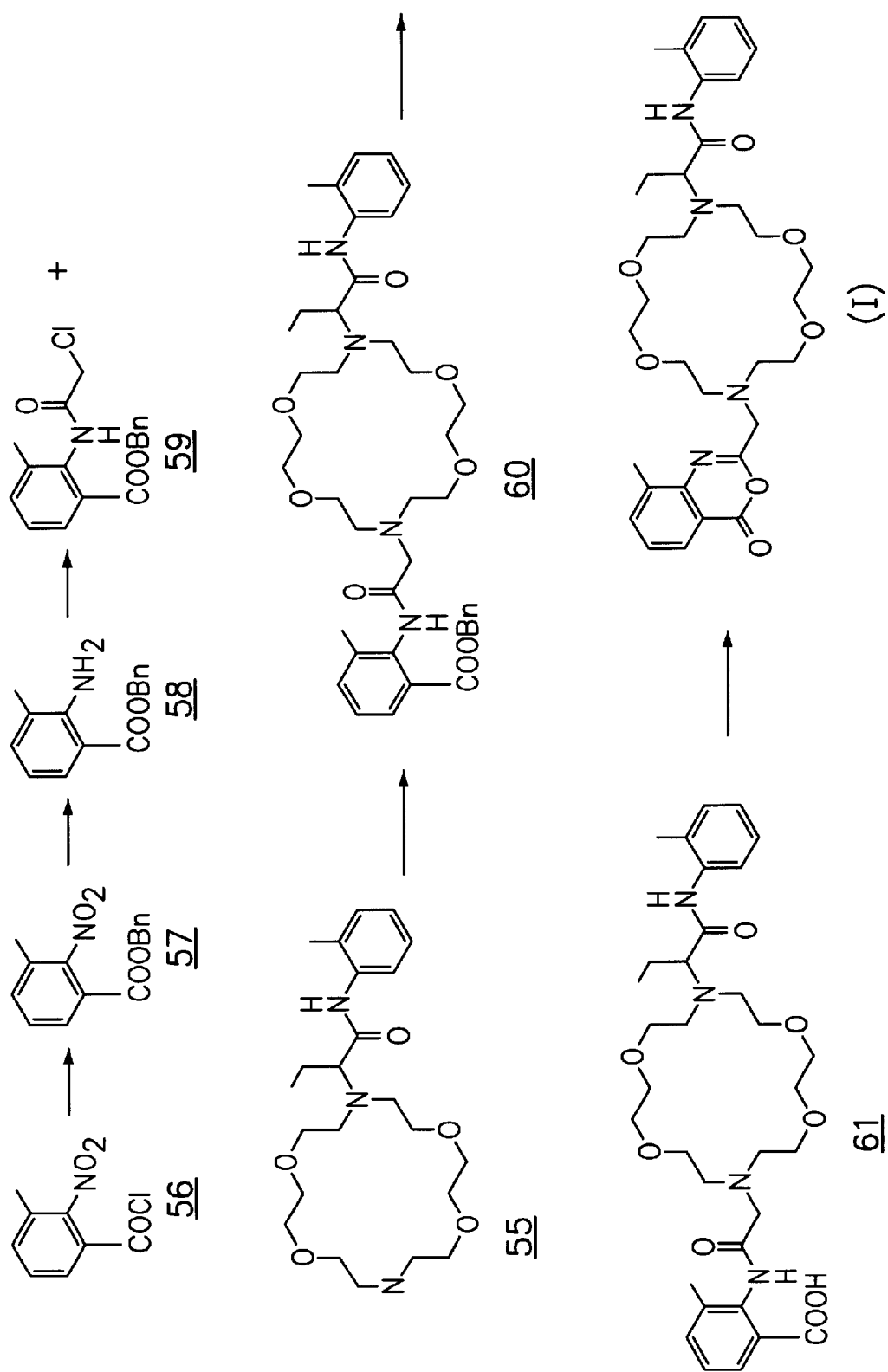

When describing the compounds, compositions and methods of this invention, the following terms have the following meanings unless otherwise indicated.

The term "alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like.

The term "substituted alkyl" refers to an alkyl group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, azido, cyano, halogen, hydroxyl, keto, thioketo, carboxyl, —COOR (where R is alkyl, aralkyl, or heteroaralkyl), thioaryloxy, thioheteroaryloxy, thioheterocyclooxy, thiol, thioalkoxy, substituted thioalkoxy, aryl, substituted aryl, aryloxy, substituted aryloxy, heteroaryl, substituted heteroaryl, heteroaryloxy, substituted heteroaryloxy, heterocyclic, substituted heterocyclic, heterocyclooxy, substituted heterocyclooxy, hydroxyamino, alkoxyamino, nitro, —SO-alkyl, —SO-aryl, —SO-substituted aryl, —SO-heteroaryl, —SO-substituted heteroaryl, —SO$_2$-alkyl, —SO$_2$-aryl, —SO$_2$-substituted aryl, —SO$_2$-heteroaryl, —SO$_2$-substituted heteroaryl, and —NR$^a$R$^b$, wherein R$^a$ and R$^b$ may be the same or different and are chosen from hydrogen, alkyl, substituted alkyl, acyl, acyloxy, cycloalkyl, alkenyl, cycloalkenyl, alkynyl, aryl, substituted aryl, heteroaryl, substituted heteroaryl, heterocyclic, and substituted heterocyclic. Preferably, this term refers to an alkyl group of 1 to 6 carbon atoms having from 1 to 5 substituents selected from the group consisting of alkoxy, aryl, substituted aryl, heteroaryl, substituted heteroaryl, heterocycle, acyl, acylamino, hydroxyl, and —NR$^a$R$^b$, wherein R$^a$ and R$^b$ may be the same or different and are chosen from hydrogen, alkyl, substituted alkyl, acyl, aryl, substituted aryl, heteroaryl, substituted heteroaryl, heterocyclic, and substituted heterocyclic. More preferably a methyl, ethyl, propyl or butyl group substituted with one or two substituents selected from hydroxy, alkoxy, —NR$^a$R$^b$, (wherein R$^a$ and R$^b$ may be the same or different and are chosen from hydrogen, alkyl, heterocycle, substituted heterocycle), aryl, heteroaryl, —COR' wherein R' is heterocyclic, substituted heterocyclic, aryl substituted aryl, —NRR' wherein R and R' are independently hydrogen, alkyl, alkoxyalkyl, hydroxyalkyl, aryl, substituted aryl, heteroaryl, dialkylaminoalkyl.

The term "hydroxyalkyl" refers to an alkyl group as defined above that is substituted with 1 to 5, preferably 1 or 2 hydroxy groups. Representative examples include, but are not limited to, groups such as 1- or 2-hydroxyethyl, hydroxymethyl, 1-, 2-, 3-hydroxypropyl, 2,3-dihydroxypropyl, and the like. The term hydroxyalkyl is a subset of substituted alkyl which is defined above.

The term "alkoxyalkyl" refers to an alkyl group as defined above that is substituted with 1 to 5, preferably 1 or 2 —OR groups (wherein R is alkyl as defined above). Representative examples include, but are not limited to, groups such as 1- or 2-methoxyethyl or ethoxyethyl, methoxymethyl, 1-, 2-, 3-methoxypropyl or ethoxypropyl, 2,3-dimethoxypropyl, and the like. The term alkoxyalkyl is a subset of substituted alkyl which is defined above.

The term "alkylene" refers to a diradical of a branched or unbranched saturated hydrocarbon chain, preferably having from 1 to 40 carbon atoms, more preferably 1 to 10 carbon atoms, even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "substituted alkylene" refers to:
(1) an alkylene group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, substituted aryl, aryloxy, substituted aryloxy, thioaryloxy, substituted thioaryloxy, heteroaryl, substituted heteroaryl, heteroaryloxy, substituted heteroaryloxy, thioheteroaryloxy, substituted thioheteroaryloxy, heterocyclic, substituted heterocyclic, heterocyclooxy, thioheterocyclooxy, nitro, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, substituted aryl, heterocyclic, substituted heterocyclic, heteroaryl or substituted heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, substituted aryl, heterocyclic, substituted heterocyclic, heteroaryl or substituted heteroaryl groups fused to the alkylene group;
(2) an alkylene group as defined above that is interrupted by 1–20 atoms independently chosen from oxygen, sulfur and —NR$^a$—, where R$^a$ is chosen from hydrogen, optionally substituted alkyl, cycloalkyl, alkenyl, cycloalkenyl, alkenyl, cycloalkenyl, alkynyl, aryl, substituted aryl, heterocyclic, substituted heterocyclic, heteroaryl or substituted heteroaryl or groups selected from carbonyl, carboxyester, carboxyamide and sulfonyl; and
(3) an alkylene group as defined above that has both from 1 to 5 substituents as defined above and is also interrupted by 1 to 20 atoms as defined above. Examples of substituted alkylenes are chloromethylene (—CH(Cl)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "alkaryl" or "aralkyl" refers to the groups -alkylene-aryl, -alkylene-substituted aryl, substituted alkylene-aryl and substituted alkylene-substituted aryl in which alkylene, substituted alkylene, aryl and substituted aryl are as defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O- alkyl and substituted alkylene-O-substituted alkyl wherein alkyl, substituted alkyl, alkylene and substituted alkylene are as defined herein. Examples of such groups are methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-tert-thiobutoxy (—CH$_2$SC(CH$_3$)$_3$) and the like.

"Alkenyl" refers to a monoradical of a branched or unbranched unsaturated hydrocarbon preferably having from 2 to 40 carbon atoms, more preferably 2 to 10 carbon atoms, even more preferably 2 to 6 carbon atoms, and preferably having 1 to 6 double bonds. This term is further exemplified by such radicals as vinyl, prop-2-enyl, pent-3-enyl, hex-5-enyl, 5-ethyldodec-3,6-dienyl, and the like.

The term "substituted alkenyl" refers to an alkenyl group as defined above having from 1 to 5 substituents selected from the group consisting of alkoxy, substituted alkoxy, acyl, acylamino, acyloxy, aminoacyl, aminoacyloxy, oxyaminoacyl, azido, cyano, halogen, hydroxyl, keto, thioketo, carboxyl, carboxylalkyl, thiol, thioalkoxy, substituted thioalkoxy, aryl, substituted aryl, aryloxy, substituted aryloxy, heteroaryl, substituted heteroaryl, heteroaryloxy, substituted heteroaryloxy, heterocyclic, substituted heterocyclic, heterocyclooxy, substituted heterocyclooxy, hydroxyamino, alkoxyamino, nitro, —SO-alkyl, —SO-aryl, substituted —SO-aryl, —SO-heteroaryl, substituted —SO-heteroaryl, —SO$_2$-alkyl, —SO$_2$-aryl, substituted —SO$_2$-aryl, —SO$_2$-heteroaryl, substituted —SO$_2$-heteroaryl, and —NR$^a$R$^b$, wherein R$^a$ and R$^b$ may be the same or different and are chosen from hydrogen, alkyl, substituted alkyl, acyl, acyloxy, cycloalkyl, alkenyl, cycloalkenyl, alkynyl, aryl, substituted aryl, heteroaryl, substituted heteroaryl, heterocyclic, and substituted heterocyclic.

"Alkenylene" refers to a diradical of an unsaturated hydrocarbon, preferably having from 2 to 40 carbon atoms, more preferably 2 to 10 carbon atoms, even more preferably 2 to 6 carbon atoms, and preferably having 1 to 6 double bonds. This term is further exemplified by such radicals as 1,2-ethenyl, 1,3-prop-2-enyl, 1,5-pent-3-enyl, 1,4-hex-5-enyl, 5-ethyl-1,12-dodec-3,6-dienyl, and the like.

The term "substituted alkenylene" refers to an alkenylene group as defined above having from 1 to 5 substituents, selected from the group consisting of alkoxy, substituted alkoxy, acyl, acylamino, acyloxy, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, substituted aryl, aryloxy, substituted aryloxy, heteroaryl, substituted heteroaryl, heteroaryloxy, substituted heteroaryloxy, heterocyclic, substituted heterocyclic, heterocyclooxy, substituted heterocyclooxy, hydroxyamino, alkoxyamino, nitro, —SO-alkyl, —SO-aryl, substituted —SO-aryl, —SO-heteroaryl, substituted —SO-heteroaryl, —SO$_2$-alkyl, —SO$_2$-aryl, substituted —SO$_2$-aryl, —SO$_2$-heteroaryl, substituted —SO$_2$-heteroaryl, and —NR$^a$R$^b$, wherein R$^a$ and R$^b$ may be the same or different and are chosen from hydrogen, alkyl, substituted alkyl, acyl, acyloxy, cycloalkyl, alkenyl, cycloalkenyl, alkynyl, aryl, substituted aryl, heteroaryl, substituted heteroaryl, heterocyclic, and substituted heterocyclic. Additionally, such substituted alkenylene groups include those where 2 substituents on the alkenylene group are fused to form one or more cycloalkyl, substituted cycloalkyl, cycloalkenyl, substituted cycloalkenyl, aryl, substituted aryl, heterocyclic, substituted heterocyclic, heteroaryl, or substituted heteroaryl groups fused to the alkenylene group.

"Alkynyl" refers to a monoradical of an unsaturated hydrocarbon, preferably having from 2 to 40 carbon atoms, more preferably 2 to 10 carbon atoms, even more preferably 2 to 6 carbon atoms, and preferably having 1 to 6 triple bonds. This term is further exemplified by such radicals as acetylenyl, prop-2-ynyl, pent-3-ynyl, hex-5-ynyl, 5-ethyldodec-3,6-diynyl, and the like.

The term "substituted alkynyl" refers to an alkynyl group as defined above having from 1 to 5 substituents, selected from the group consisting of alkoxy, substituted alkoxy, acyl, acylamino, acyloxy, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocycloxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, —SO$_2$-heterocyclic, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkynylene" refers to a diradical of an unsaturated hydrocarbon radical, preferably having from 2 to 40 carbon atoms, more preferably 2 to 10 carbon atoms, even more preferably 2 to 6 carbon atoms, and preferably having 1 to 6 triple bonds. This term is further exemplified by such radicals as 1,3-prop-2-ynyl, 1,5-pent-3-ynyl, 1,4-hex-5-ynyl, 5-ethyl-1, 12-dodec-3,6-diynyl, and the like.

The term "acyl" refers to the groups —CHO, alkyl—C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O—, heterocyclic-C(O)—, substituted heterocyclic-C(O)—, heteroaryl-C(O)—, or substituted heteroaryl-C(O)— where alkyl, substituted alkyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "acylamino" refers to the group —C(O)NRR where each R is independently hydrogen, alkyl, substituted alkyl, aryl, substituted aryl, heteroaryl, substituted heteroaryl, heterocyclic, substituted heterocyclic, or where both R groups are joined to form a heterocyclic group (e.g., morpholine) or substituted heterocyclic ring wherein alkyl, substituted alkyl, aryl, substituted aryl, heteroaryl, substituted heteroaryl, heterocyclic, and substituted heterocyclic are as defined herein.

The term "aminoacyl" refers to the group —NRC(O)R where each R is independently hydrogen, alkyl, substituted alkyl, aryl, substituted aryl, heteroaryl, substituted heteroaryl, heterocyclic, and substituted heterocyclic wherein alkyl, substituted alkyl, aryl, substituted aryl, heteroaryl, substituted heteroaryl, heterocyclic, and substituted heterocyclic are as defined herein.

The term "aminoacyloxy" refers to the group —NRC(O)OR where each R is independently hydrogen, alkyl, substituted alkyl, aryl, substituted aryl, heteroaryl, substituted heteroaryl, heterocyclic, and substituted heterocyclic wherein alkyl, substituted alkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, substituted aryl-C(O)O—, heteroaryl-C(O)O—, substituted heteroaryl-C(O)O—, heterocyclic-C(O)O— and substituted heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl).

The term "substituted aryl" refers to an aryl group as defined above which is substituted with from 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, aminoacyl, acylamino, alkaryl, aryl, aryloxy, azido, carboxyl, carboxylalkyl, cyano, halo, nitro, heteroaryl, substituted heteroaryl, heteroaryloxy, substituted heteroaryloxy, heterocyclic, substituted heterocyclic, heterocyclooxy, substituted heterocyclooxy, aminoacyloxy, oxyacylamino, thioalkoxy, substituted thioalkoxy, thioaryloxy, substituted thioaryloxy, thioheteroaryloxy, substituted thioheteroaryloxy, —SO-alkyl, —SO-substituted alkyl, —SO-aryl, —SO-substituted aryl, —SO-heteroaryl, —SO-substituted heteroaryl, —SO$_2$-alkyl, —SO$_2$-substituted alkyl, —SO$_2$-aryl, substituted —SO$_2$-aryl, —SO$_2$-heteroaryl, substituted —SO$_2$-heteroaryl, trihalomethyl, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, substituted aryl, heteroaryl, substituted heteroaryl, and heterocyclic, substituted heterocyclic. Preferred aryl substituents include alkyl, alkoxy, halo, cyano, nitro, trihalomethyl, and thioalkoxy.

The term "aryloxy" refers to the group aryl-O— wherein the aryl group is as defined above.

The term "substituted aryloxy" refers to the group substituted aryl-O— wherein the substituted aryl group is as defined above.

The term "arylene" refers to a diradical derived from aryl or substituted aryl as defined above, and is exemplified by 1,2-phenylene, 1,3-phenylene, 1,4-phenylene, 1,2-naphthylene and the like.

The term "substituted arylene" refers to a diradical derived from aryl as defined above having from 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, aminoacyl, acylamino, alkaryl, aryl, substituted aryl, aryloxy, substituted aryloxy, azido, carboxyl, carboxylalkyl, cyano, halo, nitro, heteroaryl, substituted heteroaryl, heteroaryloxy, substituted heteroaryloxy, heterocyclic, substituted heterocyclic, heterocyclooxy, substituted heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-substituted aryl, —SO-heteroaryl, —SO-substituted heteroaryl, —SO$_2$-alkyl, —SO$_2$-substituted alkyl, —SO$_2$-aryl, —SO$_2$-substituted aryl, —SO$_2$-heteroaryl, —SO$_2$-substituted heteroaryl, trihalomethyl, —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, substituted aryl, heteroaryl, substituted heteroaryl, heterocyclic, and substituted heterocyclic. Preferred arylene substituents include alkyl, alkoxy, halo, cyano, nitro, trihalomethyl, and thioalkoxy.

The term "carboxyalkyl" refers to the group "—C(O)Oalkyl" where alkyl is as defined above.

The term "alkoxycarbonyl" refers to the group "alkylC(O)O—" where alkyl is as defined above.

The term "cycloalkyl" refers to cyclic alkyl groups of from 3 to 20 carbon atoms having a single cyclic ring or multiple condensed rings. The cycloalkyl ring is optionally be fused to one or more, preferably 1 or 2 an aryl or heteroaryl ring. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents selected from the group consisting of alkyl, substituted alkyl, alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, substituted aryl, aryloxy, substituted aryloxy, heteroaryl, substituted heteroaryl, heteroaryloxy, heterocyclic, substituted heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "cycloalkylene" refers to a diradical derived from cycloalkyl or substituted cycloalkyl as defined above.

The term "substituted cycloalkylene" refers to a diradical derived from cycloalkyl as defined above having from 1 to 5 substituents selected from the group consisting of alkyl, substituted alkyl, alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, substituted aryl, aryloxy, substituted aryloxy, heteroaryl, substituted heteroaryl, heteroaryloxy, heterocyclic, substituted heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, -SO$_2$-heteroaryl, and —NR$^a$R$^b$, wherein R$^a$ and R$^b$ may be the same or different and are chosen from hydrogen, alkyl, substituted alkyl, cycloalkyl, alkenyl, cycloalkenyl, alkynyl, aryl, substituted aryl, heteroaryl, substituted heteroaryl, heterocyclic and substituted heterocyclic.

The term "cycloalkenyl" refers to cyclic alkenyl groups of from 4 to 20 carbon atoms having a single cyclic ring or fused rings and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents selected from the group consisting of alkyl, substituted alkyl, alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, substituted aryl, aryloxy, heteroaryl, substituted heteroaryl, heteroaryloxy, heterocyclic, substituted heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, substituted aryl, heteroaryl, substituted heteroaryl, heterocyclic and substituted heterocyclic.

The term "cycloalkenylene" refers to a diradical derived from cycloalkenyl or substituted cycloalkenyl as defined above.

The term "substituted cycloalkenylene" refers to a diradical derived from cycloalkenyl as defined above having from 1 to 5 substituents selected from the group consisting of alkyl, substituted alkyl, alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, substituted aryl, aryloxy, heteroaryl, substituted heteroaryl, heteroaryloxy, heterocyclic, substituted heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, substituted aryl, heteroaryl, substituted heteroaryl, heterocyclic and substituted heterocyclic.

The term "halo" or "halogen" refers to fluoro, chloro, bromo or iodo.

The term "haloalkyl" refers to alkyl as defined above substituted by 1 to 4 halo groups as defined above, which may be the same or different, such as trifluoromethyl, 3-fluorododecyl, 12,12,12-trifluorododecyl, 2-bromooctyl, -3-bromo-6-chloroheptyl, and the like.

The term "monosubstituted amino" refers to the group —NHR' where R' is alkyl.

The term "disubstituted amino" refers to the group —NR'R" where R' and R" are alkyl.

The term "heteroaryl" refers to an aromatic group of from 1 to 15 carbon atoms and 1 to 4 heteroatoms selected from oxygen, nitrogen and sulfur within at least one ring (if there is more than one ring).

The term "substituted heteroaryl" refers to a heteroaryl group as defined above which is substituted with 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, aminoacyl, acylamino, alkaryl, aryl, substituted aryl, aryloxy, azido, carboxyl, carboxylalkyl, cyano, halo, nitro, heteroaryl, substituted heteroaryl, heteroaryloxy, heterocyclic, substituted heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, mono-and di-alkylamino, mono- and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, substituted aryl, heteroaryl, substituted heteroaryl, heterocyclic and substituted heterocyclic. Preferred heteroaryls include pyridyl, pyrrolyl and furyl.

The term "heteroaryloxy" refers to the group heteroaryl-O— where heteroaryl is as defined above.

The term "substituted heteroaryloxy" refers to the group substituted heteroaryl-O— where substituted heteroaryl is as defined above.

The term "heteroarylene" refers to the diradical group derived from heteroaryl or substituted heteroaryl as defined above, and is exemplified by the groups 2,6-pyridylene, 2,4-pyridiylene, 1,2-quinolinylene, 1,8-quinolinylene, 1,4-benzofuranylene, 2,5-pyridinylene, 1,3-morpholinylene, 2,5-indolenyl, and the like.

The term "heterocycle" or "heterocyclic" refers to a saturated or unsaturated group having a single ring, multiple condensed rings or multiple covalently joined rings, from 1 to 40 carbon atoms and from 1 to 10 hetero ring atoms, preferably 1 to 4 hetero ring atoms, selected from nitrogen, sulfur, phosphorus, and/or oxygen. The heterocyclic ring is optionally fused to 1 or 2 aryl or heteroaryl ring(s).

The term "substituted heterocycle" or "substituted heterocyclic" refers to heterocycle" or "heterocyclic group as defined above which is substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, substituted aryl, aryloxy, substituted aryloxy, heteroaryl, substituted heteroaryl, heteroaryloxy, substituted heteroaryloxy, heterocyclic, substituted heterocyclic, heterocyclooxy, hydroxyamino, alkoxyamino, nitro, —SO-alkyl, —SO-substituted alkyl, —SO-aryl, —SO-substituted aryl, —SO-heteroaryl, —SO-substituted heteroaryl, —SO$_2$-alkyl, —SO$_2$-substituted alkyl, —SO$_2$-aryl, —SO$_2$-substituted aryl, —SO$_2$-heteroaryl, —SO$_2$-substituted heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, substituted aryl, heteroaryl, substituted heteroaryl, heterocyclic and substituted heterocyclic. Such heterocyclic groups can have a single ring or multiple condensed rings.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, pyrrolidine, piperazine, indoline, morpholino, piperidinyl, tetrahydrofuranyl, and the like as well as N-alkoxy-nitrogen containing heterocycles.

A preferred class of heterocyclics include "crown compounds" which refers to a specific class of heterocyclic compounds having one or more repeating units of the formula [—(CH$_2$—)$_m$Y—] where m is equal to or greater than 2, and Y at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 3 to 10 heteroatoms and 8 to 40 carbon atoms.

The term "heterocyclooxy" refers to the group heterocyclic-O— and substituted heterocyclic-O— wherein heterocyclic and substituted heterocyclic groups are as defined above.

The term "thioheterocyclooxy" refers to the group heterocyclic-S—.

The term "heterocyclene" refers to the diradical group derived from a heterocycle as defined herein, and is exemplified by the groups 2,6-morpholino, 2,5-morpholino,

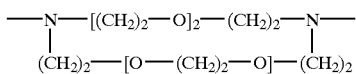

and the like.

The term "substituted heterocyclene" refers to a diradical group derived from a heterocycle as defined herein having 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, substituted aryl, aryloxy, heteroaryl, substituted heteroaryl, heteroaryloxy, heterocyclic, substituted heterocyclic, heterocyclooxy, hydroxyamino, alkoxyamino, nitro, —SO-alkyl, —SO-substituted alkyl, —SO-aryl, —SO-substituted aryl, —SO-heteroaryl, —SO-substituted heteroaryl, —SO$_2$-alkyl, —SO$_2$-substituted alkyl, —SO$_2$-aryl, —SO$_2$-heteroaryl, —SO$_2$-substituted aryl, —SO$_2$-substituted heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, substituted aryl, heteroaryl, substituted heteroaryl, heterocyclic and substituted heterocyclic. Such heterocyclic groups can have a single ring or multiple condensed rings.

The term "oxyacylamino" refers to the group —OC(O)NRR where each R is independently hydrogen, alkyl, substituted alkyl, aryl, substituted aryl, heteroaryl, substituted heteroaryl, heterocyclic and substituted heterocyclic wherein alkyl, substituted alkyl, aryl, substituted aryl, heteroaryl, substituted heteroaryl, heterocyclic and substituted heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including substituted aryl groups also defined above.

The term "thioheteroaryloxy" refers to the group heteroaryl-S— wherein the heteroaryl group is as defined above including substituted heteroaryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "heteroarylalkyl" refers to heteroaryl and substituted heteroaryl as defined above linked to alkyl as defined above, for example pyrid-2-ylmethyl, 8-quinolinylpropyl, and the like.

The term "optional" or "optionally" means that the subsequently described event or circumstance may or may not occur, and that the description includes instances where said event or circumstance occurs and instances in which it does not. For example, optionally substituted alkyl means that alkyl may or may not be substituted by those groups enumerated in the definition of substituted alkyl.

The term "pharmaceutically acceptable salt" refers to salts which retain the biological effectiveness and properties of the multi-binding compounds of this invention and which are not biologically or otherwise undesirable. In many cases, the multi-binding compounds of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to reestablish the hydroxyl, thiol, amino or carboxyl group. See, generally, T. W. Greene & P. G. M. Wuts "Protective Groups in Organic Synthesis," $2^{nd}$ Ed, 1991, John Wiley and Sons, N.Y.

The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product. Preferred carboxyl protecting groups include esters such as methyl, ethyl, propyl, t-butyl etc. which can be removed by hydrolysis conditions compatible with the nature of the product.

As used herein, the terms "inert organic solvent" or "inert solvent" mean a solvent inert under the conditions of the reaction being described in conjunction therewith including, for example, benzene, toluene, acetonitrile, tetrahydrofuran ("THF"), dimethylformamide ("DMF"), chloroform ("$CHCl_3$"), methylene chloride (or dichloromethane or "$CH_2Cl_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The term "$Na^+$ channel" or "sodium ion channel" refers to a biomembrane-associated structure that is capable of transporting sodium ions across a lipid membrane. The sodium channels pertinent to this invention are voltage-gated channels that mediate action potentials in mediate action potentials in excitable tissues (e.g., nerve and muscle).

"Potency" as used herein refers to the minimum concentration at which a compound of formula (I) is able to achieve a desirable biological or therapeutic effect.

The term "treatment" refers to any treatment of a disease or condition in a mammal, particularly a human, and includes:

(i) preventing the disease or condition from occurring in a subject which may be predisposed to the condition but has not yet been diagnosed with the condition and, accordingly, the treatment constitutes prophylactic treatment for the pathologic condition;

(ii) inhibiting the disease or condition, i.e., arresting its development;

(iii) relieving the disease or condition, i.e., causing regression of the disease or condition; or (iv) relieving the symptoms resulting from the disease or condition, e.g., relieving pain without addressing the underlying disease or condition.

The term "disease or condition which is modulated by treatment with a local anesthetic " covers all disease states and/or conditions associated with pain sensation that are generally acknowledged in the art to be usefully treated with a local anesthetic compound and those disease states and/or conditions that have been found to be usefully treated by a specific local anesthetic compound of our invention, i.e., the compounds of Formula I. Such disease states and conditions include, by way of example only, surgical anesthesia, post operative pain relief, post-arthroscopic pain management, chronic inflammatory pain, neurogenic pain, long-duration surgical block, proctitis and active distal ulcerative colitis, and the like.

The term "therapeutically effective amount" refers to that amount of multi-binding compound that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable excipient" is intended to include vehicles and carriers capable of being co-administered with a multi-binding compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present invention.

The term "linker", identified where appropriate by the symbol X, refers to a group that covalently links $L_1$ and $L_2$ (as defined in the Summary of the Invention above). In some cases, the linker may itself be biologically active. The term linker embraces everything that is not considered to be part of the $L_1$ and $L_2$, e.g., ancillary groups such as solubilizing groups, lipophilic groups, groups that alter pharmacodynamics or pharmacokinetics, groups that modify the diffusability of a compound of Formula (I), groups that attach $L_1$ and $L_2$ to the linker. The term "linker" does not, however, cover solid inert supports such as beads, glass particles, rods, and the like, but it is to be understood that the multi-binding compounds of this invention can be attached to a solid support if desired, for example, for use in separation and purification processes and for similar applications.

"Multibinding agent" or "multibinding compound" refers to a compound of Formula (I) that is capable of multivalency as defined below. The extent to which multivalent binding is realized depends upon the efficiency with which the linker that joins $L_1$ and $L_2$ presents them to their binding sites on the sodium channel.

The term "multivalency" as used herein refers to the concurrent binding of $L_1$ and $L_2$ (which may be the same or different) and two or more corresponding receptors (ligand binding sites) which may be the same or different.

Nomenclature

In general, the compounds of Formula (I) are numbered based on the IUPAC nomenclature.

For example, a group of formula (a) where E is phenyl, G is —$NR^7$— and $R^3$ and $R^4$ form C=O group is numbered as follow:

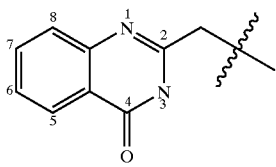

For a group of formula (c) the aryl ring substituents are numbered such that the ring atom that connects the ring to W is position 1.

PREFERRED EMBODIMENTS

While the broadest definition of this invention is set forth in the Summary of the Invention, the following are the preferred embodiments of this invention:

Preferably E is aryl, more preferably phenyl.

Preferably G is —O— or —NR$^7$— where R$^7$ is alkyl, substituted alkyl, aryl, substituted aryl, heteroaryl, substituted heteroaryl, heterocycle or substituted heterocycle. More preferably, G is —NR$^7$— where R$^7$ is aryl, substituted aryl or substituted alkyl, preferably methyl, ethyl, propyl, phenyl, or an alkyl group of 1 to 6 carbon atoms substituted with 1 to 3 substituents selected from the group consisting of alkoxy, aryl, substituted aryl, heteroaryl, substituted heteroaryl, heterocycle, acyl, acylamino, hydroxyl, and —N$^a$R$^b$ (wherein R$^a$ and R$^b$ may be the same or different and are chosen from the group consisting of hydrogen, alkyl, substituted alkyl, acyl, aryl, substituted aryl, heteroaryl, substituted heteroaryl, heterocyclic, and substituted heterocyclic). Even more preferably, R$^7$ is methyl, ethyl, propyl or butyl group which is substituted with 1 or 2 substituents selected from the group consisting of hydroxy, alkoxy, aryl, heteroaryl, heteroaryl substituted with one or two substituents selected from the group consisting of methyl and —OR (where R is hydrogen or alkyl); heterocyclic, heterocyclic substituted with one or two methyl groups; —NR$^a$R$^b$, (wherein R$^a$ and R$^b$ may be the same or different and are chosen from hydrogen, alkyl, heterocycle, substituted heterocycle or —COR$^x$ where R$^x$ is alkyl), and —COR' [wherein R' is heterocyclic, substituted heterocyclic, aryl, substituted aryl, —NR$^c$R$^d$ (where R$^c$ and R$^d$ are independently hydrogen, alkyl, alkoxyalkyl, hydroxyalkyl, aryl, substituted aryl, heteroaryl, dialkylaminoalkyl, heterocycle, or —COR$^x$ where R' is alkyl or —OCOR$^y$ where R$^y$ is alkyl) or —OR$^e$ wherein R$^e$ is alkyl or substituted alkyl]. Most preferably, R$^7$ is methyl, 2-methylpropyl, 2-methoxyethyl, 2-morpholin-4-ylethyl, 2-N,N-dimethylaminoethyl, 2-N,N-diethylaminoethyl, 3-N,N-dimethylaminopropyl, 2-acetylaminoethyl, 2-[N,N-(2-acetyloxyethyl)amino]ethyl, 3-acetyloxy-2-hydroxypropyl, 2-hydroxyethyl, 3-hydroxypropyl, 2,3-dihydroxypropyl, 2-(imidazol-4-yl)ethyl, 2-(pyridin-3-yl)ethyl, 2-(indol-3-yl)ethyl, 2-(5-methoxyindol-3-yl)ethyl, 3-(imidazol-1-yl)ethyl, 3-(2-oxo-pyrrolidin-1-yl)propyl, 2-(2-oxoimidazolidin-1-yl)-ethyl, phenyl, morpholin-4-ylcarbonylmethyl, N,N-dimethylaminocarbonylmethyl, 2-(N,N-dimethylaminoethyl)carbonylmethyl, 2-N,N-(2-hydroxyethyl)aminoethyl, N,N-diethylaminocarbonylmethyl, piperidin-1-ylcarbonylmethyl, N,N-(2-methoxyethyl)-aminocarbonylmethyl, N-ethylamino-carbonylmethyl, N-(2-dimethylaminoethyl)aminocarbonylmethyl, N-pyridin-3-ylamino-carbonylmethyl, 1-methylpiperazin-4-ylcarbonylmethyl, 4-oxopiperidin-1-yl-carbonylmethyl, 2-piperidin-1-ylethyl, 3-(4-methylpiperazin-1-yl)propyl, 2-pyrrolidin-1-ylethyl, 3-pyrrolidin-1-ylpropyl, 2-N,N-dimethylaminoethyl, N-tetrahydropyran-4-ylaminocarbonylmethyl, N-pyridin-3-ylamino-carbonylmethyl, benzoylmethyl, 4-methoxybenzoylmethyl, benzyloxycarbonyl-methyl, benzyl, pyridin-2-ylmethyl, pyridin-3-ylmethyl, pyridin-4-ylmethyl, 5-methylpyrazin-2-ylmethyl, furan-2-ylmethyl; even more preferably morpholin-4-ylcarbonylmethyl, phenyl, pyridin-3-ylmethyl, pyridin-4-ylmethyl, N-ethylaminocarbonylmethyl, 2-(imidazol-4-yl)ethyl, furan-2-ylmethyl, or 2-(indol-3-yl)ethyl. Particularly preferably R$^7$ is morpholin-4-ylcarbonylmethyl.

Preferably R$^3$ and R$^4$ together with the carbon atom to which they are attached form a carbonyl group.

Preferably R$^1$ is hydrogen, alkyl, more preferably hydrogen, methyl, or ethyl, even more preferably R$^1$ is methyl.

Preferably R$^2$ is hydrogen, alkyl, more preferably hydrogen, methyl, or ethyl, even more preferably R$^2$ is hydrogen.

Preferably R$^5$ is hydrogen, alkyl, more preferably hydrogen, methyl, or ethyl, even more preferably R$^5$ is hydrogen.

Preferably R$^6$ is hydrogen, alkyl, more preferably hydrogen, methyl, or ethyl, even more preferably R$^6$ are hydrogen.

Preferably X is alkylene, substituted alkylene, or heterocyclene, more preferably heterocyclene containing at least two nitrogen atoms, even more preferably

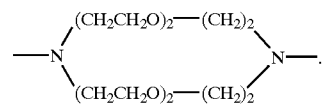

Preferably W is —NH—C(O)[CR$^8$R$^9$]$_r$— where r is 1 and R$^8$ and R$^9$ are independently selected from the group consisting of hydrogen or alkyl, preferably hydrogen, methyl, or ethyl. More preferably, W is —NH—C(O)*CR$^8$R$^9$— wherein R$^8$ is hydrogen and R$^9$ is ethyl and the stereochemistry at the *C is (RS), (R) or (S), more preferably (R).

Preferably Ar is aryl or substituted aryl, more preferably Ar is phenyl optionally substituted with one, two or three substituents selected from the group consisting of alkyl, acyl, or alkoxy, even more preferably Ar is 2-methylphenyl, 2,3-, 2,4-, 2,5-, 2,6-, 3,4-, or 3,5-dimethylphenyl; most preferably 2-methylphenyl.

Preferably, L$_1$ is represented by a group of formula (a):

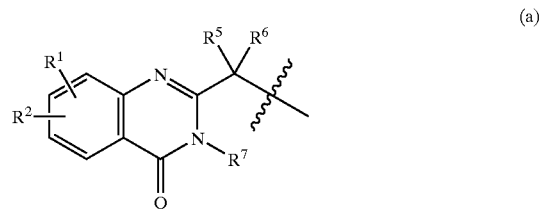

(a)

wherein R$^1$, R$^2$, R$^3$ and R$^4$, R$^5$, R$^6$ and R$^7$ are as defined herein including their preferred embodiments.

Preferably L₂ is a group of formula:

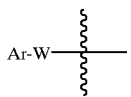
(c)

wherein:
Ar is selected from the group consisting of aryl, substituted aryl, heteroaryl, substituted heteroaryl, heterocycle, substituted heterocycle, cycloalkyl and substituted cycloalkyl;
W is a covalent bond, —[CR⁸R⁹]ᵣ—, —[CR⁸R⁹]ᵣC(O)—, —C(O)O[CR⁸R⁹]ᵣ—, —OC(O)[CR⁸R⁹]ᵣ—, —O—[CR⁸R⁹]ᵣC(O)—, —C(O)—NH—[CR⁸R⁹]ᵣ—, or —NH—C(O)[CR⁸R⁹]ᵣ where r is an integer of 0 to 10, and R⁸ and R⁹ are independently selected from the group consisting of hydrogen, alkyl, substituted alkyl and —NRᵃRᵇ— where Rᵃ and Rᵇ are both alkyl.

Within this group, a more preferred group of compounds is that wherein Ar is aryl or substituted aryl, preferably Ar is phenyl optionally substituted with one, two or three substituents selected from the group consisting of alkyl, alkoxy or acyl, more preferably Ar is 2-methylphenyl, 2,3-, 2,4-, 2,5-, 2,6-, 3,4-, or 3,5-dimethylphenyl; most preferably 2-methylphenyl.

Within this group another more preferred group of compounds is that wherein W is —NH—C(O)[CR⁸R⁹]ᵣ— where r is 1 and R⁸ and R⁹ are independently selected from the group consisting of hydrogen or alkyl, preferably hydrogen, methyl, or ethyl. More preferably W is —NH—C(O)*CR⁸R⁹— wherein R⁸ is hydrogen and R⁹ is ethyl and the stereochemistry at the *C is (RS), (R) or (S), more preferably (R).

Within this group another more preferred group of compounds is that wherein Ar—W— is:
2,6-dimethylphenyl-NH—C(O)—CH₂—;
2,6-dimethylphenyl-NH—C(O)—CH((CH₂)₂CH₃)—;
2,6-dimethylphenyl-NH—C(O)—;
(S)-2,6-dimethylphenyl-NH—C(O)—CH(CH₂CH₃)—;
(R)-2,6-dimethylphenyl-NH—C(O)—CH(CH₂CH₃)—;
o-tolyl-N—C(O)—CH(CH₂CH₃)—;
o-tolyl-NH—C(O)—CH(CH₃)—;
o-tolyl-NH—C(O)—CH₂—;
4-[(CH₃CH₂)₂N—(CH₂)₂—O—C(O)—]-phenyl-;
4-[(CH₃CH₂)₂N—(CH₂)₂—NH—C(O)—]-phenyl-;
4-[(CH₃)—NH—C(O)—]-phenyl-;
4-[(CH₃)₂N—(CH₂)₂—O—C(O)—]-phenyl-;
4-[CH₃—CH₂—O—C(O)—]-2,6-dimethylphenyl-NH—C(O)—CH₂—;
4-[CH₃—O—C(O)—]-2,6-dimethylphenyl-NH—C(O)—CH(CH₂CH₃)—;
4-[CH₃—O—C(O)—]-2-methylphenyl-NH—C(O)—CH(CH₂CH₃)—;
4-aminophenyl-C(O)—;
4-butylaminophenyl-C(O)—;
2,6-dimethylphenyl-O—C(O)—CH₂—;
phenyl-(CH₂)₃—;
phenyl-C(O)—(CH₂)₂—;
4-[(CH₃CH₂)₂N—CH₂—C(O)—NH—]-3,5-dimethylphenyl-O—CH₂—C(O)—;
4-aminophenyl-C(O)—O—(CH₂)₂—;
4-methoxyphenyl-NH—C(O)—CH₂—;
phenyl-NH—C(O)—CH₂—;
4-chlorophenyl-NH—C(O)—CH₂—;
2-methyl-4-methoxyphenyl-NH—C(O)—CH₂—;
2-methyl-4-chlorophenyl-NH—C(O)—CH₂—;
(R)-2-methylphenyl-NH—C(O)—*CH(CH₂CH₃)—;
(S)-2-methylphenyl-NH—C(O)—*CH(CH₂CH₃)—;
phenyl-(CH₂)₂—C(O)—;
4-nitrophenyl-C(O)—O—(CH₂)₂—;
2-chloro-4-nitrophenyl-C(O—O—(CH₂)₂—;
(S)-2,6-dimethylphenyl-NH—C(O)—CH(N(CH₃)₂)—;
(R)-2,6-dimethylphenyl-NH—C(O)—CH(N(CH₃)₂)—;
(S)-2,6-dimethylphenyl-NH—C(O)—CH(N(CH₂CH₃)₂)—;
(R)-2,6-dimethylphenyl-NH—C(O)—CH(N(CH₂CH₃)₂)—;
4-{[R—[O—C(O)—(CH₂)ₙ]ₘ—O}-2,6-dimethylphenyl-NH—C(O)-CHR'—, where n is an integer equal to 1 to 6, m is 0 or 1, R is C₁-C₆ alkyl, and R' is H or alkyl;
2-ethyl-6-methylphenyl-NH—C(O)—CH(CH₂CH₃)—;
2,4,6-trimethylphenyl-CH(CH₂CH₃)—C(O)—NH—; or
2-ethyl-6-methylphenyl-NH—C(O)—CH₂—;
2-isopropylphenyl-NH—C(O)—CH₂—; or
2,4,6-trimethylphenyl-NH—C(O)—CH₂—.

Most preferably, Ar—W— is (R)-2-methylphenyl-NH—C(O)—*CH(CH₂CH₃)—; or (S)-2-methylphenyl-NH—C(O)—*CH(CH₂CH₃)— wherein *C denotes the chiral carbon.

Preferably X is a group of the formula:

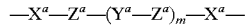
—Xᵃ—Zᵃ—(Yᵃ—Zᵃ)ₘ—Xᵃ— wherein:
m is an integer of from 0 to 20;
Xᵃ at separate occurrence is either a covalent bond or —NR wherein R is selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, substituted aryl, heteroaryl, substituted heteroaryl, heterocyclic, and substituted heterocyclic;
Zᵃ at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, substituted arylene, substituted heteroarylene, substituted heterocyclene, and a covalent bond;
each Yᵃ at each separate occurrence is selected from the group consisting of —O—, —C(O)—, —OC(O)—, —C(O)O—, —NR—, —S(O)n—, —C(O)NR'—, —NR' C(O)—, —NR'—C(O)NR'—, —NR'C(S)NR'—, —C(=NR')—NR'—, —NR'—C(=NR')—, —OC(O)—NR'—, —NR'—C(O)—O—, —P(O)(OR')—O—, —O—P(O)(OR')—, —S(O)ₙCR'R"—, —S(O)ₙ—NR'—, —NR'—S(O)ₙ—, —S—S—, and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, substituted aryl, heteroaryl, substituted heteroaryl, heterocyclic, and substituted heterocyclic provided that at least one of $Z^a$, and $Y^a$ is not a covalent bond.

More preferably, X is either:

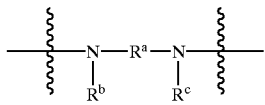

wherein:
$R^a$ is alkylene, substituted alkylene, alkenylene or substituted alkenylene; and
$R^b$ and $R^c$ are, independently of each other, hydrogen, alkyl, substituted alkyl; or
a heterocyclene group, preferably a heterocyclene containing from 6 to 18 ring atoms of which two ring atoms are nitrogen and the rest are selected from carbon and oxygen provided that each of the heteroatoms in the heterocyclene ring is separated form each other by at least 2 carbon atoms; more preferably

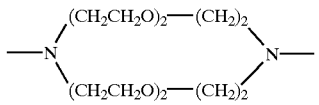

Yet another preferred group of compound of Formula (I) is wherein $L_1$ is represented by a group of formula (b):

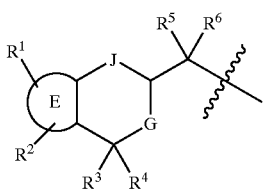

wherein J, E, G, $R^1$, $R^2$, $R^3$, $R^4$, $R^5$ and $R^6$ are as defined herein.

Within this group a more preferred group of compounds is that wherein:
J is —O—; and
E, G, $R^1$, $R^2$, $R^3$, $R^4$, $R^5$ and $R^6$ are as defined in the preferred embodiments above.

Yet another preferred group of compounds is that wherein $L_2$ is a group of formula (d):

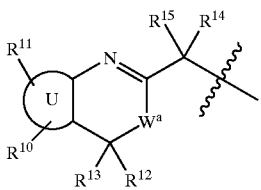

wherein:
E is aryl, preferably phenyl.

Within this group, a more preferred group of compounds is that wherein:
$W^a$ is —O— or —$NR^{16}$— where $R^{16}$ is alkyl, substituted alkyl, aryl, substituted aryl, heteroaryl, substituted heteroaryl, heterocycle or substituted heterocycle; and $R^{12}$ and $R^{13}$ together with the carbon atom to which they are attached form a carbonyl group.

Within this more preferred group, an even more preferred group of compounds is that wherein $R^{10}$ and $R^{11}$ are independently of each other hydrogen, alkyl, halo or alkoxy, $R^{14}$ and $R^{15}$ are independently hydrogen or alkyl, preferably hydrogen or alkyl, more preferably hydrogen, methyl, or ethyl, even more preferably $R^{10}$ is methyl and $R^{11}$, $R^{14}$ and $R^{15}$ are hydrogen.

Within these more preferred and an even more preferred groups, a particularly preferred group of compounds is that wherein W is —$NR^{16}$— where $R^{16}$ is methyl, ethyl, propyl, phenyl, or an alkyl group of 1 to 6 carbon atoms substituted with 1 to 3 substituents selected from the group consisting of alkoxy, aryl, substituted aryl, heteroaryl, substituted heteroaryl, heterocycle, acyl, acylamino, hydroxyl, and —$NR^aR^b$ (wherein $R^a$ and $R^b$ may be the same or different and are chosen from hydrogen, alkyl, substituted alkyl, acyl, aryl, substituted aryl, heteroaryl, substituted heteroaryl, heterocyclic, and substituted heterocyclic). More preferably, $R^{16}$ is methyl, ethyl, propyl or butyl group which is substituted with 1 or 2 substituents selected from the group consisting of hydroxy, alkoxy, aryl, heteroaryl, heteroaryl substituted with one or two substituents selected from the group consisting of methyl and —OR (where R is hydrogen or alkyl), heterocyclic, heterocyclic substituted with one or two methyl; —$NR^aR^b$ (wherein $R^a$ and $R^b$ may be the same or different and are chosen from hydrogen, alkyl, heterocycle, substituted heterocycle or —$COR^x$ where $R^x$ is alkyl), and —COR' [wherein R' is heterocyclic, substituted heterocyclic, aryl, substituted aryl, —$NR^cR^d$ (where $R^c$ and $R^d$ are independently hydrogen, alkyl, alkoxyalkyl, hydroxyalkyl, aryl, substituted aryl, heteroaryl, dialkylaminoalkyl, heterocycle, or —$COR^x$ where $R^x$ is alkyl or —$OCOR^y$ where $R^y$ is alkyl) or —$OR^e$ wherein $R^e$ is alkyl or substituted alkyl]. Even more preferably $R^{16}$ is methyl, 2-methylpropyl, 2-methoxyethyl, 2-morpholin-4-ylethyl, 2-N,N-dimethylaminoethyl, 2-N,N-diethylaminoethyl, 3-N,N-dimethylaminopropyl, 2-acetylaminoethyl, 2-[N,N-(2-acetyloxyethyl)amino]ethyl, 3-acetyloxy-2-hydroxypropyl, 2-hydroxyethyl, 3-hydroxypropyl, 2,3-dihydroxypropyl, 2-(imidazol-4-yl) ethyl, 2-(pyridin-3-yl)ethyl, 2-(indol-3-yl)ethyl, 2-(5-methoxyindol-3-yl)ethyl, 3-(imidazol-1-yl)ethyl, 3-(2-oxo-pyrrolidin-1-yl)propyl, 2-(2-oxoimidazolidin-1-yl)ethyl, phenyl, morpholin-4-ylcarbonylmethyl, N,N-dimethylaminocarbonylmethyl, 2-(N,N-dimethylaminoethyl)carbonylmethyl, 2-N,N-(2-hydroxyethyl)aminoethyl, N,N-diethylaminocarbonylmethyl, piperidin-1-ylcarbonylmethyl, N,N-(2-methoxyethyl)-aminocarbonylmethyl, N-ethylaminocarbonylmethyl, N-(2-dimethyl-aminoethyl)aminocarbonylmethyl, N-pyridin-3-ylaminocarbonylmethyl, 1-methylpiperazin-4-ylcarbonylmethyl, 4-oxopiperidin-1-ylcarbonylmethyl, 2-piperidin-1-ylethyl, 3-(4-methylpiperazin-1-yl)propyl, 2-pyrrolidin-1-ylethyl, 3-pyrrolidin-1-ylpropyl, 2-N,N-dimethylaminoethyl, N-tetrahydropyran-4-ylaminocarbonylmethyl, N-pyridin-3-ylaminocarbonylmethyl, benzoylmethyl, 4-methoxybenzoylmethyl, benzyloxycarbonyl-methyl, benzyl, pyridin-2-ylmethyl, pyridin-3-ylmethyl, pyridin-4-ylmethyl, 5-methylpyrazin-2-ylmethyl, furan-2-ylmethyl; even more preferably morpholin-4-ylcarbonylmethyl, phenyl, pyridin-3-ylmethyl, pyridin-4-ylmethyl, N-ethylaminocarbonylmethyl, 2-(imidazol-4-yl)ethyl, furan-2-ylmethyl, or 2-(indol-3-yl) ethyl; most preferably morpholin-4-ylcarbonylmethyl.

In a preferred embodiment the compounds of Formula (I) have the formula (Ia) shown below:

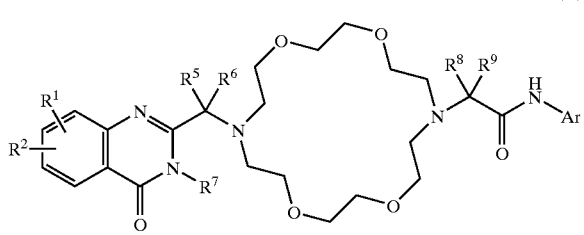

(Ia)

wherein:
R¹ and R² are independently selected from the group consisting of hydrogen, alkyl, halo, cyano, hydroxy, alkoxy, amino, monosubstituted or disubstituted amino, carboxy, and alkoxycarbonyl;
R⁵ and R⁶ are independently selected from the group consisting of hydrogen and alkyl;
R⁷ is alkyl, substituted alkyl, aryl, substituted aryl, heteroaryl, substituted heteroaryl, heterocycle or substituted heterocycle;
R⁸ and R⁹ are independently selected from the group consisting of hydrogen, alkyl, substituted alkyl and —NRᵃRᵇ— where Rᵃ and Rᵇ are both alkyl; and
Ar is selected from the group consisting of aryl, substituted aryl, heteroaryl, substituted heteroaryl, heterocycle, substituted heterocycle, cycloalkyl or substituted cycloalkyl; or
a pharmaceutically acceptable salt thereof.

Within this group, a preferred group of compounds is that wherein:
R¹ and R² are independently selected from the group consisting of hydrogen, methyl, ethyl, n-propyl, 2-propyl, chloro, fluoro, cyano, hydroxy, methoxy, ethoxy, n-propoxy, 2-propoxy, amino, methylamino, and dimethylamino; more preferably hydrogen or methyl; even more preferably R¹ is hydrogen and R² is methyl and is at the C-8 position of the quinazolone ring; and
R⁵ and R⁶ are independently selected from the group consisting of hydrogen, methyl, and ethyl, preferably hydrogen.

Another more preferred group of compounds in the compounds of formula (Ia) is that wherein R⁷ is methyl, ethyl, propyl, phenyl, or an alkyl group of 1 to 6 carbon atoms substituted with 1 to 3 substituents selected from the group consisting of alkoxy, aryl, substituted aryl, heteroaryl, substituted heteroaryl, heterocycle, acyl, acylamino, hydroxyl, and —NRᵃRᵇ (wherein Rᵃ and Rᵇ may be the same or different and are chosen from hydrogen, alkyl, substituted alkyl, acyl, aryl, substituted aryl, heteroaryl, substituted heteroaryl, heterocyclic, and substituted heterocyclic). More preferably R⁷ is methyl, ethyl, propyl or butyl group which is substituted with 1 or 2 substituents selected from the group consisting of hydroxy, alkoxy, aryl, heteroaryl, heteroaryl substituted with one or two substituents selected from the group consisting of methyl and —OR (where R is hydrogen or alkyl), heterocyclic, heterocyclic substituted with one or two methyl; —NRᵃRᵇ, (wherein Rᵃ and Rᵇ may be the same or different and are chosen from hydrogen, alkyl, heterocycle, substituted heterocycle or —CORˣ where Rˣ is alkyl), and —COR' [wherein R' is heterocyclic, substituted heterocyclic, aryl, substituted aryl, —NRᶜRᵈ (where Rᶜ and Rᵈ are independently hydrogen, alkyl, alkoxyalkyl, hydroxyalkyl, aryl, substituted aryl, heteroaryl, dialkylaminoalkyl, heterocycle, or —CORˣ where Rˣ is alkyl or —OCORʸ where Rʸ is alkyl) or —ORᵉ wherein Rᵉ is alkyl or substituted alkyl]. Even more preferably R⁷ is methyl, 2-methylpropyl, 2-methoxyethyl, 2-morpholin-4-ylethyl, 2-N,N-dimethylaminoethyl, 2-N,N-diethylaminoethyl, 3-N,N-dimethylaminopropyl, 2-acetylaminoethyl, 2-[N,N-(2-acetyloxyethyl)amino]ethyl, 3-acetyloxy-2-hydroxypropyl, 2-hydroxyethyl, 3-hydroxypropyl, 2,3-dihydroxypropyl, 2-(imidazol-4-yl)ethyl, 2-(pyridin-3-yl)ethyl, 2-(indol-3-yl)ethyl, 2-(5-methoxyindol-3-yl)ethyl, 3-(imidazol-1-yl)ethyl, 3-(2-oxopyrrolidin-1-yl)propyl, 2-(2-oxoimidazolidin-1-yl)ethyl, phenyl, morpholin-4-ylcarbonylmethyl, N,N-dimethylaminocarbonylmethyl, 2-(N,N-dimethylaminoethyl)carbonylmethyl, 2-N,N-(2-hydroxyethyl)aminoethyl, N,N-diethylaminocarbonylmethyl, piperidin-1-ylcarbonylmethyl, N,N-(2-methoxyethyl)-aminocarbonylmethyl, N-ethylaminocarbonylmethyl, N-(2-dimethyl-aminoethyl)aminocarbonylmethyl, N-pyridin-3-ylaminocarbonylmethyl, 1-methylpiperazin-4-ylcarbonylmethyl, 4-oxopiperidin-1-ylcarbonylmethyl, 2-piperidin-1-ylethyl, 3-(4-methylpiperazin-1-yl)propyl, 2-pyrrolidin-1-ylethyl, 3-pyrrolidin-1-ylpropyl, 2-N,N-dimethylaminoethyl, N-tetrahydropyran-4-ylaminocarbonylmethyl, N-pyridin-3-ylaminocarbonylmethyl, benzoylmethyl, 4-methoxybenzoylmethyl, benzyloxycarbonyl-methyl, benzyl, pyridin-2-ylmethyl, pyridin-3-ylmethyl, pyridin-4-ylmethyl, 5-methylpyrazin-2-ylmethyl, furan-2-ylmethyl; even more preferably morpholin4-ylcarbonylmethyl, phenyl, pyridin-3-ylmethyl, pyridin-4-ylmethyl, N-ethylaminocarbonylmethyl, 2-(imidazol-4-yl)ethyl, furan-2-ylmethyl, or 2-(indol-3-yl)ethyl; most preferably morpholin-4-ylcarbonylmethyl.

Within the more preferred group, an even more preferred group of compounds of formula (Ia) is that wherein:
R⁸ is hydrogen;
R⁹ is hydrogen or alkyl, more preferably hydrogen, methyl or ethyl, most preferably ethyl wherein the stereochemistry at the carbon to which R⁸ and R⁹ are attached is(RS), (S), or (R), preferably (R); and
Ar— is substituted phenyl, preferably, 2-methylphenyl, 2-isopropylphenyl, 2,6-dimethylphenyl, or 2,4,6-trimethylphenyl.

In yet another preferred embodiment the compounds of Formula (I) have the formula (Ib) shown below:

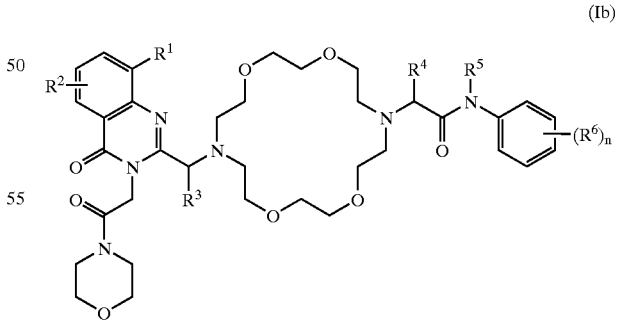

(Ib)

wherein:
R¹ is selected from the group consisting of hydrogen, C₁₋₆ alkyl and C₁₋₆ alkoxy;
R² is selected from the group consisting of hydrogen, C₁₋₆ alkyl and C₁₋₆ alkoxy;
R³ is hydrogen or C₁₋₆ alkyl;

$R^4$ is hydrogen or $C_{1-6}$ alkyl;
$R^5$ is hydrogen or $C_{1-6}$ alkyl;
each $R^6$ is independently selected from the group consisting of $C_{1-6}$ alkyl and $C_{1-6}$ alkoxy;
n is an integer from 0 to 3;

and pharmaceutically acceptable salts and stereoisomers thereof.

Preferably the compound of Formula (I) as defined in the Summary of the Invention and in the preferred embodiments above is multibinding.

(I) Representative compounds of this invention are as follows:

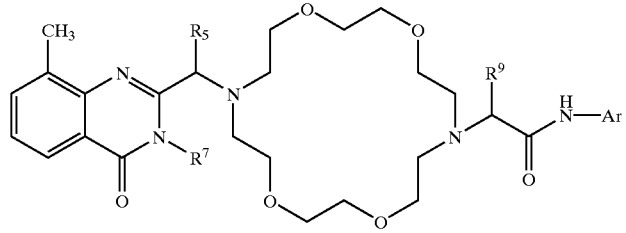

| Cpd. # | Stereochem | $R^7$ | $R^5$ | $R^9$ | Ar— | Mass Spec. M + H |
|---|---|---|---|---|---|---|
| 1 | RS | morpholin-4-ylCOCH$_2$— | H | CH$_3$CH$_2$— | 2-methylphenyl | 737.7 |
| 2 | S | morpholin-4-ylCOCH$_2$— | H | CH$_3$CH$_2$— | 2-methylphenyl | 737.7 |
| 3 | R | morpholin-4-ylCOCH$_2$— | H | CH$_3$CH$_2$— | 2-methylphenyl | 737.7 |
| 4 | RS | morpholin-4-ylCOCH$_2$— | H | CH$_3$— | 2-methylphenyl | 723.5 |
| 5 | RS | morpholin-4-ylCOCH$_2$— | H | CH$_3$CH$_2$— | 2,6-dimethylphenyl | 751.4 |
| 6 | RS | morpholin-4-ylCOCH$_2$— | H | CH$_3$CH$_2$— | 2-ethylphenyl | 751.4 |
| 7 | RS | morpholin-4-ylCOCH$_2$— | H | CH$_3$(CH$_2$)$_2$— | 2-methylphenyl | 751.5 |
| 8 | | morpholin-4-ylCOCH$_2$— | H | H | 2,6-dimethylphenyl | 723.5 |
| 9 | | morpholin-4-ylCOCH$_2$— | H | H | 2-isopropylphenyl | 737.3 |
| 10 | | morpholin-4-ylCOCH$_2$— | H | H | 2-ethylphenyl | 723.5 |
| 11 | | morpholin-4-ylCOCH$_2$— | H | H | 2-methylphenyl | 709.4 |
| 12 | | morpholin-4-ylCOCH$_2$— | H | H | 2,4,6-trimethylphenyl | 737.3 |
| 13 | | morpholin-4-ylCOCH$_2$— | H | H | 2-methyl-6-ethylphenyl | 737.3 |
| 14 | RS, RS | morpholin-4-ylCOCH$_2$— | CH$_3$CH$_2$— | CH$_3$CH$_2$— | 2-methylphenyl | 765.3 |
| 15 | | (CH$_3$)$_2$NCOCH$_2$— | H | CH$_3$CH$_2$— | 2-methylphenyl | 695.4 |
| 16 | RS | (CH$_3$CH$_2$)$_2$NCOCH$_2$— | H | CH$_3$CH$_2$— | 2-methylphenyl | 723.5 |
| 17 | RS | piperdin-1-ylCOCH$_2$— | H | CH$_3$CH$_2$— | 2-methylphenyl | 735.5 |
| 18 | RS | [CH$_3$O(CH$_2$)$_2$]$_2$NCOCH$_2$— | H | CH$_3$CH$_2$— | 2-methylphenyl | 783.6 |
| 19 | RS | (CH$_3$CH$_2$)NHCOCH$_2$— | H | CH$_3$CH$_2$— | 2-methylphenyl | 695.7 |
| 20 | RS | (CH$_3$)$_2$N(CH$_2$)$_2$NHCOCH$_2$— | H | CH$_3$CH$_2$— | 2-methylphenyl | |
| 21 | RS | 4-CH$_3$-piperzin-1-yl-COCH$_2$— | H | CH$_3$CH$_2$— | 2-methylphenyl | |
| 22 | RS | 4-oxopiperdin-1-yl-COCH$_2$— | H | CH$_3$CH$_2$— | 2-methylphenyl | |
| 23 | RS | tetrahydropyran-4-yl-NH—COCH$_2$— | H | CH$_3$CH$_2$— | 2-methylphenyl | |
| 24 | RS | pyridin-3-yl-NHCO—CH$_2$— | H | CH$_3$CH$_2$— | 2-methylphenyl | |
| 25 | RS | phenylCOCH$_2$— | H | CH$_3$CH$_2$— | 2-methylphenyl | 728.4 |
| 26 | RS | 4-methoxyphenylCO—CH$_2$— | H | CH$_3$CH$_2$— | 2-methylphenyl | 758.6 |
| 27 | RS | benzyloxy-COCH$_2$— | H | CH$_3$CH$_2$— | 2-methylphenyl | 758.8 |
| 28 | RS | benzyl | H | CH$_3$CH$_2$— | 2-methylphenyl | 700.4 |
| 29 | RS | pyridin-2-ylCH$_2$— | H | CH$_3$CH$_2$— | 2-methylphenyl | 701.6 |
| 30 | RS | pyridin-3-ylCH$_2$— | H | CH$_3$CH$_2$— | 2-methylphenyl | 701.6 |
| 31 | RS | pyridin-4-ylCH$_2$— | H | CH$_3$CH$_2$— | 2-methylphenyl | 701.6 |
| 32 | RS | 5-CH$_3$-pyrazin-2-yl-CH$_2$— | H | CH$_3$CH$_2$— | 2-methylphenyl | 716.3 |
| 33 | RS | furan-2-ylCH$_2$— | H | CH$_3$CH$_2$— | 2-methylphenyl | 690.5 |
| 34 | RS | CH$_3$— | H | CH$_3$CH$_2$— | 2-methylphenyl | 624.6 |
| 35 | RS | phenyl | H | CH$_3$CH$_2$— | 2-methylphenyl | 686.3 |
| 36 | RS | (CH$_3$)$_2$CHCH$_2$— | H | CH$_3$CH$_2$— | 2-methylphenyl | |
| 37 | RS | CH$_3$OCH$_2$CH$_2$— | H | CH$_3$CH$_2$— | 2-methylphenyl | 668.4 |
| 38 | RS | morpholin-4-ylCH$_2$.CH$_2$— | H | CH$_3$CH$_2$— | 2-methylphenyl | 723.5 |
| 39 | RS | (CH$_3$)$_2$NCH$_2$CH$_2$— | H | CH$_3$CH$_2$— | 2-methylphenyl | 681.5 |
| 40 | RS | CH$_3$CONHCH$_2$CH$_2$— | H | CH$_3$CH$_2$— | 2-methylphenyl | 695.3 |
| 41 | RS | (AcOCH$_2$CH$_2$)$_2$N—CH$_2$CH$_2$— | H | CH$_3$CH$_2$— | 2-methylphenyl | |
| 42 | RS | AcOCH$_2$CH(OH)CH$_2$— | H | CH$_3$CH$_2$— | 2-methylphenyl | |
| 43 | RS | HOCH$_2$CH(OH)CH$_2$— | H | CH$_3$CH$_2$— | 2-methylphenyl | 684.5 |
| 44 | RS | imidazol-4-ylCH$_2$CH$_2$— | H | CH$_3$CH$_2$— | 2-methylphenyl | 704.6 |
| 45 | RS | pyridin-3-ylCH$_2$CH$_2$— | H | CH$_3$CH$_2$— | 2-methylphenyl | 715.4 |
| 46 | RS | indol-3-ylCH$_2$CH$_2$— | H | CH$_3$CH$_2$— | 2-methylphenyl | 753.5 |
| 47 | RS | 5-CH$_3$Oindol-3-ylCH$_2$.CH$_2$— | H | CH$_3$CH$_2$— | 2-methylphenyl | 783.5 |
| 48 | RS | imidazol-1-yl(CH$_2$)$_3$— | H | CH$_3$CH$_2$— | 2-methylphenyl | |
| 49 | RS | 2-oxopyrrolidin-1-yl-(CH$_2$)$_3$— | H | CH$_3$CH$_2$— | 2-methylphenyl | 735.5 |
| 50 | RS | 2-(piperidin-1-yl)ethyl | H | CH$_3$CH$_2$— | 2-methylphenyl | 707.6 |
| 51 | RS | 2-(pyrrolidin-1-yl)ethyl | H | CH$_3$CH$_2$— | 2-methylphenyl | 721.7 |
| 52 | RS | 2-ethylaminoethyl | H | CH$_3$CH$_2$— | 2-methylphenyl | 709.4 |
| 53 | RS | 3-(4-methylpiperazin-1-yl)propyl | H | CH$_3$CH$_2$— | 2-methylphenyl | 750.6 |
| 54 | RS | 3-(piperidin-1-yl)propyl | H | CH$_3$CH$_2$— | 2-methylphenyl | 721.4 |
| 55 | RS | 3-(pyrrolidin-1-yl)propyl | H | CH$_3$CH$_2$— | 2-methylphenyl | |

-continued (I) Representative compounds of this invention are as follows:

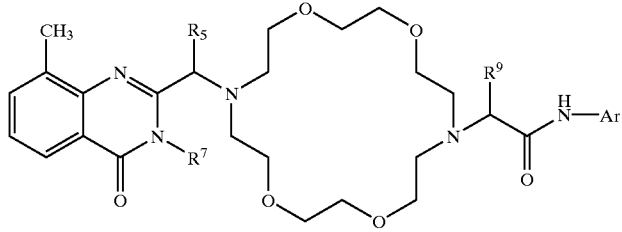

| Cpd. # | Stereo-chem | R[7] | R[5] | R[9] | Ar— | Mass Spec. M + H |
|---|---|---|---|---|---|---|
| 56 | RS | 2-diethylaminoethyl | H | $CH_3CH_2$— | 2-methylphenyl | |
| 57 | RS | 3-dimethylaminopropyl | H | $CH_3CH_2$— | 2-methylphenyl | |
| 58 | RS | 2-(2-oxoimidazolidin-1-yl)propyl | H | $CH_3CH_2$— | 2-methylphenyl | |
| 59 | RS | 3-hydroxypropyl | H | $CH_3CH_2$— | 2-methylphenyl | |
| 60 | RS | 2-[bis(2-hydroxyethyl)amino]ethyl | H | $CH_3CH_2$— | 2-methylphenyl | |
| 61 | RS | 2-hydroxyethyl | H | $CH_3CH_2$— | 2-methylphenyl | |
| 62 | RS | 3-(dimethylaminoethyl)-aminocarbonylmethyl | H | $CH_3CH_2$— | 2-methylphenyl | |
| 63 | RS | (4-methylpiperazin-1-yl)carbonylmethyl | H | $CH_3CH_2$— | 2-methylphenyl | |
| 64 | RS | (tetrahydropyran-4-ylamino)-carbonylmethyl | H | $CH_3CH_2$— | 2-methylphenyl | |
| 65 | RS | (pyridin-3-ylamino)carbonylmethyl | H | $CH_3CH_2$— | 2-methylphenyl | |
| 66 | | (morpholin-4-yl)carbonylmethyl | H | H | 2,3-dimethylphenyl | |
| 67 | | (morpholin-4-yl)-carbonylmethyl | H | H | 2,4-dimethylphenyl | |
| 66 | | (morpholin-4-yl)-carbonylmethyl | H | H | 2,5-dimethylphenyl | |
| 67 | | (morpholin-4-yl)-carbonylmethyl | H | H | 3,4-dimethylphenyl | |
| 68 | | (morpholin-4-yl)-carbonylmethyl | H | H | 3,5-dimethylphenyl | |

(II) Other representative compounds of the Invention are:

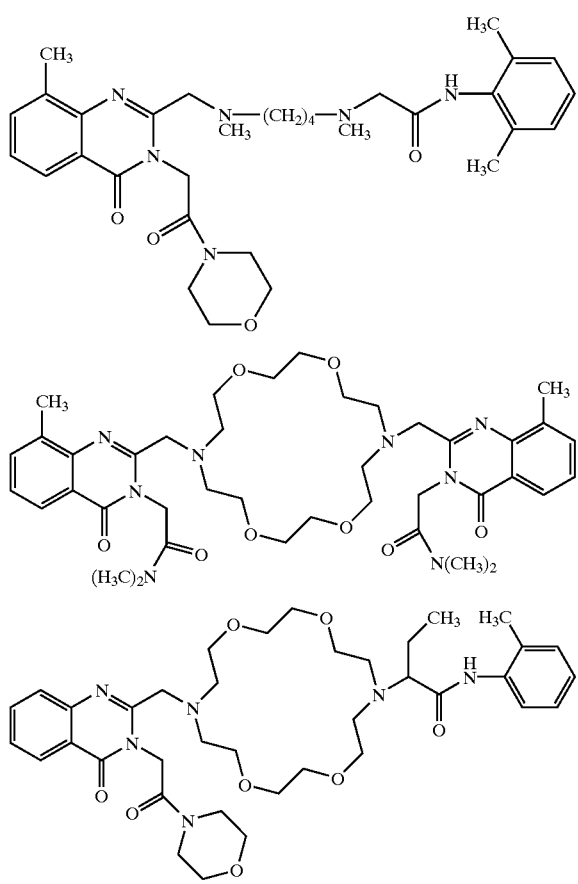

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989).

The starting materials and the intermediates of the reaction may be isolated and purified if desired using conventional techniques well known in the art, including but not limited to filtration, distillation, crystallization, chromatography, and the like. Such materials may be characterized using conventional means, including physical constants and spectral data.

Furthermore, it will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis,* Third Edition, Wiley, New York, 1999, and references cited therein.

These schemes are merely illustrative of some methods by which the compounds of this invention can be synthesized, and various modifications to these schemes can be made and will be suggested to one skilled in the art having referred to this disclosure.

Preparation of a Compound of Formula (I)

In general, compounds of Formula (I) can be prepared as illustrated and described in Schemes A–D below.

A compound of Formula (I) can be prepared as shown in Scheme A below.

Scheme A

Method (a)

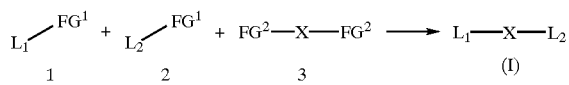

Method (b)

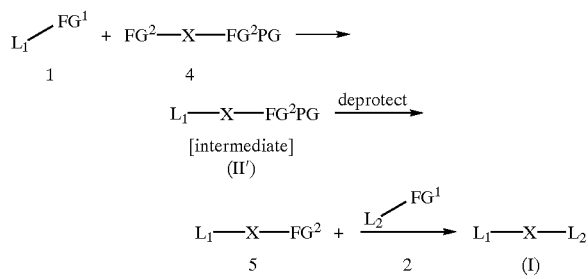

Method A

In method (a), a compound of Formula (I) is prepared in one step by reacting compounds of formula 1 and 2 (where $L_1$ and $L_2$ are as defined in the Summary of the Invention and $FG^1$ represents a functional group) with a compound of formula 3 (where X represents a linker as defined in the Summary of the Invention and $FG^2$ represents a functional group).

The reaction conditions used to link compounds 1 and 2 to compound 3 depend on the nature of the functional groups on compounds 1, 2, and 3 which in turn depend on the type of linkage desired. Examples of the functional groups and the reaction conditions that can be used to generate a specific linkage is described below.

TABLE I

Representative Complementary Binding Chemistries

| First Reactive Group | Second Reactive Group | Linkage |
|---|---|---|
| carboxyl | amine | amide |
| sulfonyl halide | amine | sulfonamide |
| hydroxyl | alkyl/aryl halide | ether |
| hydroxyl | isocyanate | urethane |
| amine | epoxide | β-hydroxyamine |
| amine | halide | amine |
| hydroxyl | carboxyl | ester |
| amine | aldehyde | amine |

Reaction between a carboxylic acid group on 1 and 2 and a primary or secondary amine group on 3 or vice versa in the presence of suitable, well-known activating agents such as dicyclohexylcarbodiimide provides a compound of Formula (I) wherein $L_1$ and $L_2$ and the linker are linked via an amido bond; reaction between an amine group on 1 and 2 and a sulfonyl halide group on 3, in the presence of a base such as triethylamine, pyridine, an the like provides a compound of Formula (I) wherein $L_1$ and $L_2$ and the linker are linked via a sulfonamido group; and reaction between an amino group on 1 and 2 and a halo group on 3 or vice versa in the presence of a base such as triethylamine, pyridine, and the like, provides a compound of Formula (I) wherein the $L_1$ and $L_2$ and the linker are linked via an amino group.

Method (a) is preferred when $L_1$ and $L_2$ are the same.

Method B

In method (b), a compound of Formula (I) is prepared in a stepwise manner by covalently attaching one equivalent of a compound of formula 1 with a compound of formula 4 where X is a linker as defined in the Summary of the Invention is pre and $FG^2PG$ is a protected function group to give an intermediate of formula (II'). Deprotection of the second functional group on the linker, followed by reaction of resulting compound 5 with one equivalent of compound 2, which may be same or different than compound 1, then provides a compound of Formula (I). The coupling of compounds 1 and 2 to compound compounds 4 and 5 respectively, is carried out under the reaction conditions described above. This method is preferred when $L_1$ and $L_2$ are different.

Compounds of formula 1 can be prepared by methods well known in the art. For example, synthesis of 2-bromomethyl-3-(2-hydroxyethyl)quinazolin-4-one and 2-bromoethyl-3-(2-hydroxyethyl)quinazolin-4-one is described in *J. Heterocyclic Chem.,* 30, 1413, 1993. Other quinazolin-4-ones where the functional group is bromo can be prepared by first preparing 2-methylquinazol-4-ones following the procedures described in *J. Med. Chem.,* Vol 15, No. 5. pages 518–523; *J. Indian Chem. Soc.,* Vol. LV, pages 465–467, 1978; and *J. Indian Chem. Soc.,* Vol. 67, pages 46–47, 1990; followed by carrying out alpha-bromination reaction as described in *Heterocyclic Chem.,* 30, 1413, 1993. It will be recognized by one skilled in the art that compounds of formula 1 where the functional group is other than bromo can be prepared from corresponding compounds of formula 1 where the function group is bromo by methods well known in the art.

Synthesis of compounds of formula 2 where $L_2$ is a compound of formula (c) is described in Applicants' PCT Application Publication No. WO 99/51565, filed Apr. 2, 1999 the disclosure of which is incorporated herein by reference.

Compounds of formula 3 are commercially available or they can be prepared by methods well known in the art.

A compound of Formula (I) where $L_1$ is a group of formula (a) where G is —$NR^7$— and $R^3$ and $R^4$ together with the carbon atom to which they are attached form —C=O and $L_2$ is a group of formula Ar—W— where W is —NH—C(O)[$CR^8R^9$]— wherein both the $L_1$ and $L_2$ are attached to the linker, X, via an amino group can also be prepared as described in Scheme B below.

Scheme B

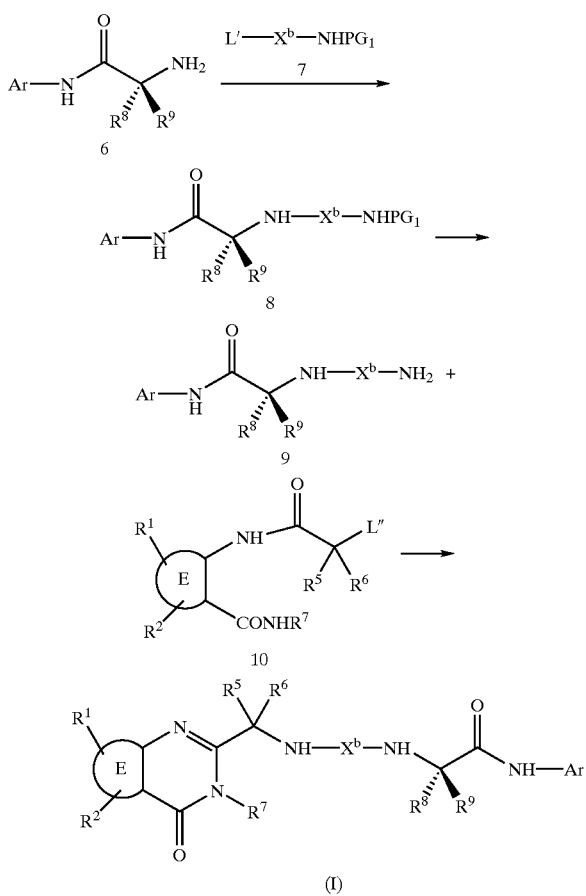

(I)

Reaction of an amine of formula 6 with a compound of formula 7 (where L' is a leaving e.g., halo, mesylate, tosylate and the like, preferably halo, $X^b$ is $-Z^a-(Y^a-Z^a)_m-$ where $Z^a$, $Y^a$, and m are as defined in the Summary of the Invention, and $PG_1$ is a suitable protecting group e.g., Cbz, tert-butoxycarbonyl, benzyl, and the like) under nucleophilic displacement reaction conditions, followed by removal of the amino protecting group in the resulting compound of formula 8 provides a compound of formula 9. The nucleophilic displacement reaction is carried out in the presence of a base and in an inert organic solvent such as acetonitrile, dimethylformamide, and the like. The reaction conditions employed for the removal of $PG_1$ group depend on the type of the protecting group. For example, if $PG_1$ is benzyloxycarbonyl or benzyl then it is removed under catalytic hydrogenation reaction conditions well known in the art. If it is tert-butoxycarbonyl, it is removed under acidic reaction conditions.

Compounds of formula 6 can be prepared from alpha amino acid as illustrated and described below:

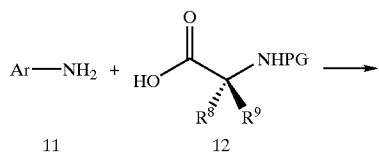

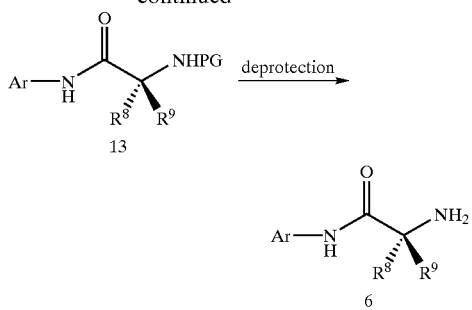

Reaction of an amine of formula 11 with an alpha amino acid of formula 12 where PG is a suitable amino protecting group (e.g., benzyloxycarbonyl (Cbz group) and the like) provides a compound of formula 13. The reaction is carried out in the presence of a coupling agent (e.g., dicyclohexylcarbodiimide, N-[(dimethylamino)-1H-1,2,3-triazolo[4,5-b]pyridin-1-ylmethylene]-N-methylmethanaminium hexafluorophosphate N-oxide (HATU) and the like) and an organic base (e.g., diisopropylamine, dimethylaminopyridine, and the like). When N-[(dimethylamino)-1H-1,2,3-triazolo[4,5-b]pyridin-1-ylmethylene]-N-methylmethanaminium hexafluorophosphate N-oxide is used, the reaction is carried out in the presence of a catalyst such as 1-hydroxy-7-azabenzotriazole. Suitable solvents are inert organic solvents such as dimethylformamide, methylene chloride, and the like.

Removal of the amino protecting group provides a compound of formula 6. The reaction conditions employed for the removal of the amino protecting group depend on the kind of group used. For example, if benzyl is used as the protecting group then it is removed under catalytic hydrogenation reaction conditions. If tert-butoxycarbonyl is used, then it is removed under acidic reaction conditions.

Compounds of formula 11 are commercially available or they can be prepared by methods well known in the art. For example, aniline, 2,6-dimethylaniline, cyclohexylamine, 4-aminopyridine, and 2-aminopyrimidine are commerically available. Others can be prepared from compounds carrying a nitro group such as nitrophenol, 5-nitro-1,10,-phenanthroline by reduction of the nitro group to give the corresponding amino compound which can then be coupled with a compound of formula 12 as described above.

N-Protected alpha amino acids of formula 12 are commercially available or they can be prepared by methods well known in the art. For example, N-protected alpha amino acids such as Cbz-glycine, Cbz-alanine, Cbz-arginine, Cbz-glutamic acid, and Cbz-lysine are commercially available. It will be recognized by one skilled in the art that the carboxy and the amino functional groups on the side chains of Cbz-glutamic acid, and Cbz-lysine have to be suitably protected prior to carrying out the coupling reaction.

Compounds of formula 7 can be prepared by methods well known in the art. For example, compounds such as N-3,6-dioxa-8-iodooctylbenzylamine can be prepared by reacting benzylamine with 3,6-dioxa-1,8-diiodooctane in the presence of a non-nucleophilic organic base such as diisopropylethylamine and the like. Suitable organic solvents are polar solvents such as ethanol.

It will be readily recognized by one skilled in the art that if a compound of formula 8 where the $ArNHC(O)CR^8R^9-$ is attached to a cyclic linker such as 1,4,10,15-tetraoxa-7,16-diazacyclooctadecane is desired, then it can be prepared by reacting 2 equivalents of 3,6-dioxa-1,8-diiodooctane with benzylamine to provide bis-N,N-3,6-dioxa-8-iododctylbenzylamine which upon reaction with compound 6 provides a compound of formula 8 wherein the ArNHCOCR$^8$R$^9$— group is attached to an N-protected cyclic diamine linker.

Removal of the amino protecting group, PG$_1$, in 8 followed by coupling of the resulting compound of formula 9 with a compound of formula 10 (where L" is a leaving group such as halo, preferably chloro or bromo) in the presence of an organic base such as diisopropylethyl amine, and in an inert organic solvent such as dimethylformamide, ethanol or mixtures thereof provides a compound of Formula (I) wherein L$_1$ and L$_2$ are linked to the linker via an amino group. The reaction occurs upon heating.

It is contemplated that isolation of the intermediate:

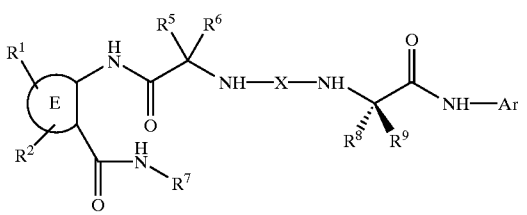

can be facilitate by use of basic conditions.

Compounds of formula 10 are prepared as illustrated and described below:

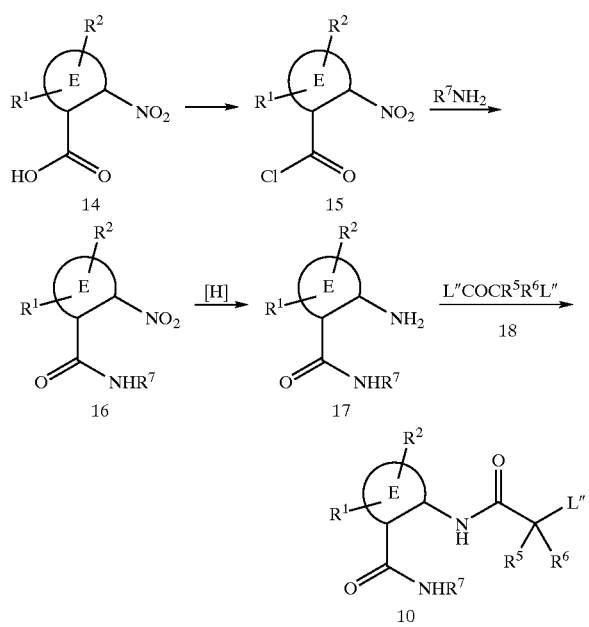

Treatment of a 2-nitro-carboxylic acid compound of formula 14 with a chlorinating agent such as oxalyl chloride, thionyl chloride, preferably oxalyl chloride in an inert organic solvent such as dichloromethane with catalytic amount of dimethylformamide provides an acyl chloride of formula 15.

Compounds of formula 14 are commercially available. For example, 2-nitrobenzoic acid, 3-methyl-2-nitrobenzoic acid, 3-chloro-2-nitrobenzoic acid, 3-hydroxy-4-methyl-2-nitrobenzoic acid, 6-nitro-IH-benzoimidazole-5-carboxylic acid are commercially available.

Reaction of 15 with an amine of formula R$^7$NH$_2$ where R$^7$ is as defined in the Summary of the Invention provides a 2-amido-nitro compound of formula 16. The reaction is carried out in the presence of a base and in an organic solvent such as dichloromethane, and the like.

Amines of formula R$^7$NH$_2$ are commercially available or they can be prepared by methods well known in the art. For example, ethylamine, propylamine, benzylamine, 11-aminoundecanoic acid, aminopropanol, 1-(3-aminopropyl)imidazole, 4-(3-aminopropyl)morpholine are commercially available. Others can be prepared by methods well known in the art. For example, an amine of formula NH$_2$CHR'CONR"$_2$ where R' is hydrogen, alkyl, aryl, substituted alkyl and R" is alkyl or both together with the nitrogen atom to which they are attached form a heterocyclic ring can be prepared by reacting an N-protected alpha amino acid with an amine such as ethylamine, piperidine, piperazine, morpholine, and the like in the presence of a coupling agent such as HATU or dicyclohexylcarbodiimide and the like, followed by deprotection of the amino group.

Detailed description of synthesis of an amine NH$_2$CHR'CONR"$_2$ where R' is hydrogen and NR"$_2$ is a morpholino group by this procedure is provided in Examples 1 and 6 below.

Reduction of the nitro group in compound 16 followed by coupling of the resulting amine 17 with a compound of formula 18 where L" is a halo group such as chloro or bromo provides a compound of formula 10.

Alternatively, a compound of formula 17 can be prepared as described in Example 10 below.

Compounds of formula 18 such as chloroacetyl chloride, 2-bromobutyryl bromde, (R) and (S)-2-bromobutyryl bromide are commercially available. Others can be prepared by methods well known in the art.

Alternatively, a compound of formula 10 can be prepared from 14 by first reducing the nitro group and then carrying out the chlorination, amination, and acylation reactions as described above.

Preparation of a compound of Formula (I) by the method described above is described in Example 2.

Alternatively, a compound of Formula (I) where L$_1$ is a group of formula (a) where G is —NR$^7$— and R$^3$ and R$^4$ together with the carbon atom to which they are attached form —C=O and L$_2$ is a group of formula Ar—W— where W is —NH—C(O)[CR$^8$R$^9$]— wherein both L$_1$ and L$_2$ are attached to the linker, X, via an amino group can be described in Scheme C below.

Scheme C

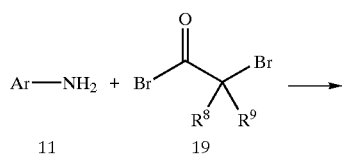

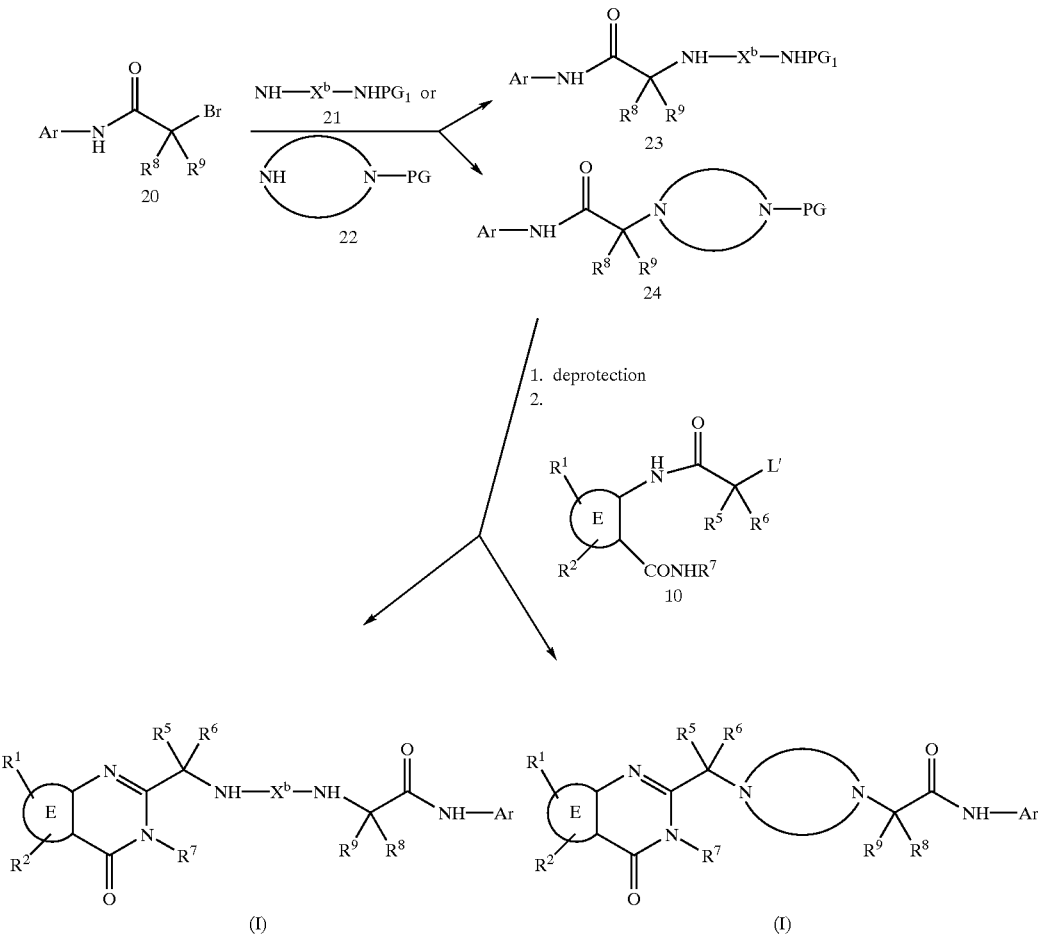

Reaction of a compound of formula 11 where Ar is as defined in the Summary of the Invention with an alpha bromoacetyl bromide of formula 19 in glacial acetic acid and sodium acetate provides a compound of formula 20.

Compound 19 is commerically available. For example alpha bromoacetyl bromide and alpha bromobutryl bromide are commercially available.

Reaction of 20 with an acyclic linker 21 [linker X where $X^a$ are NH and $—Z^a—(Y^a—Z^a)_m—$ are represented as $X^b$] or a cyclic linker 22 respectively under the reaction conditions described above provide a compound of formula 23 or 24 respectively. Compounds 23 and 24 are then converted to a compound of Formula (I) wherein the linker is acyclic or cyclic under the reaction conditions described above.

Figure 4:
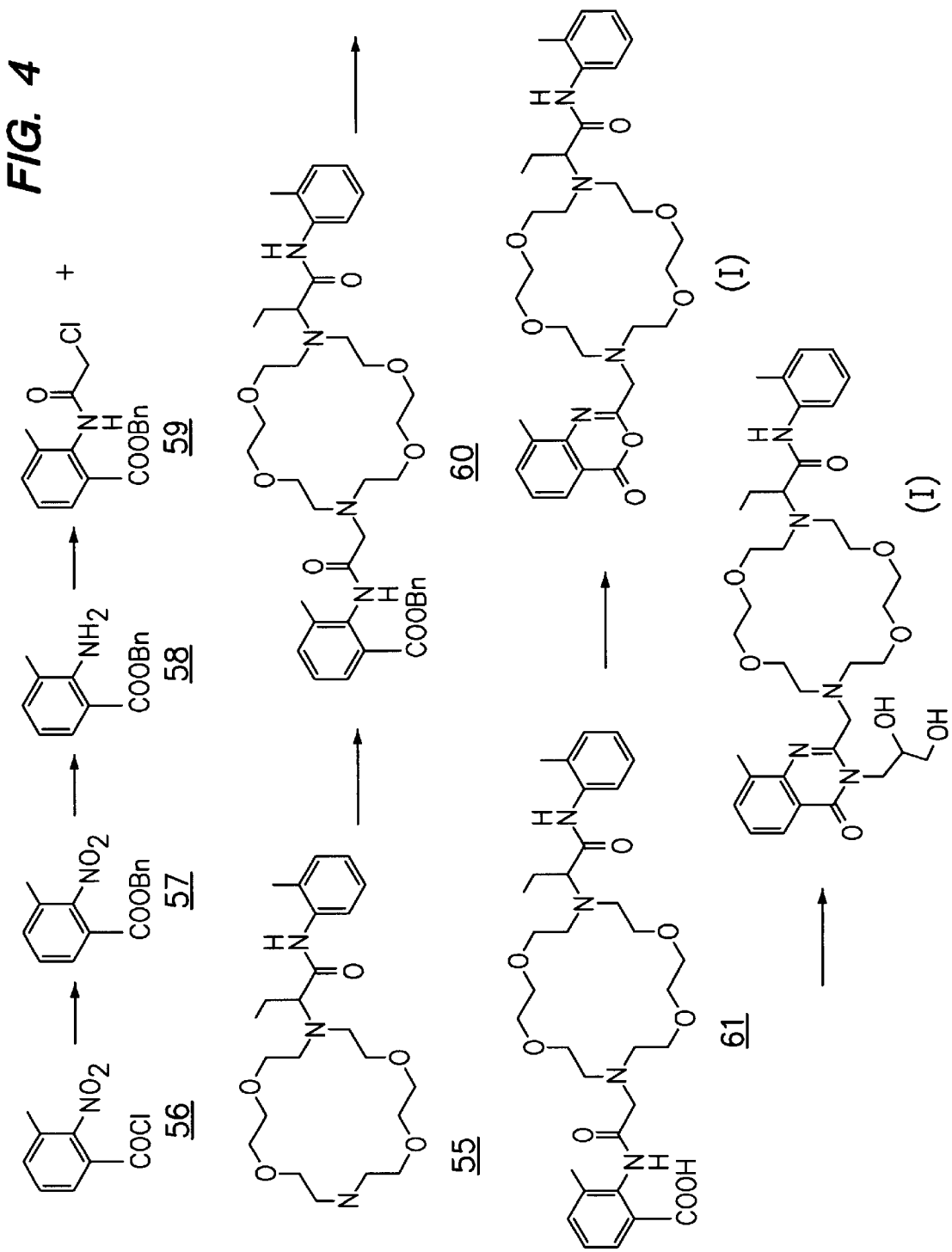
Figure 5:
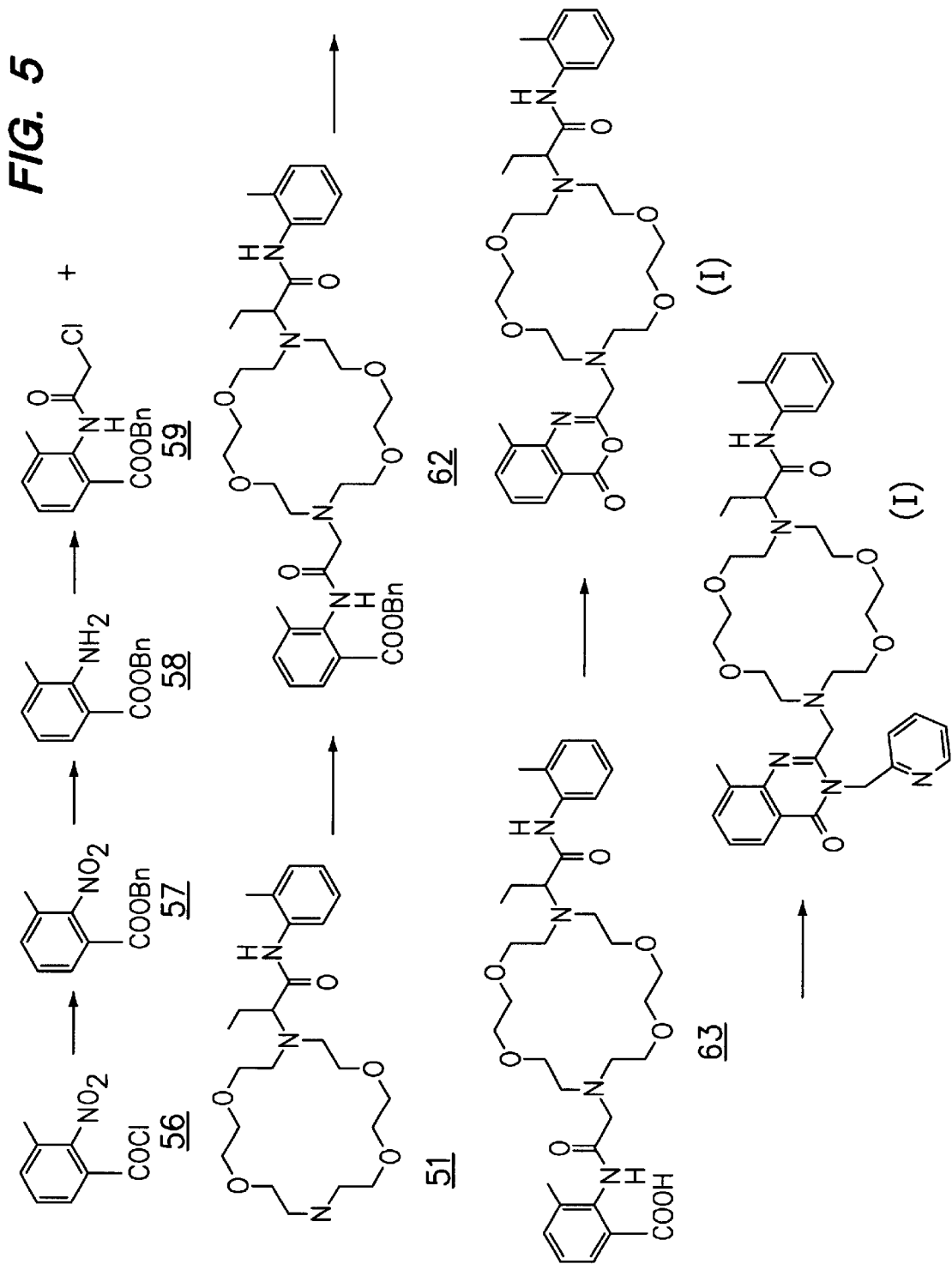

Acyclic and cyclic diamines are commercially available (see FIG. 4 and 5).

A compound of Formula (I) where $L_1$ is a group of formula (a) where G is —O— and $R^3$ and $R^4$ together with the carbon atom to which they are attached form —C═O and $R^5$ and $R^6$ are as defined in the Summary of the Invention and $L_2$ is a group of formula Ar—W— where W is —NH—C(O)[$CR^8R^9$]— and wherein both the $L_1$ and $L_2$ are attached to the linker, X, via an amino group can also be prepared as described in Scheme D below.

Scheme D

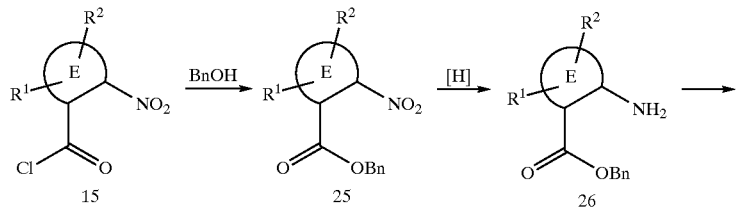

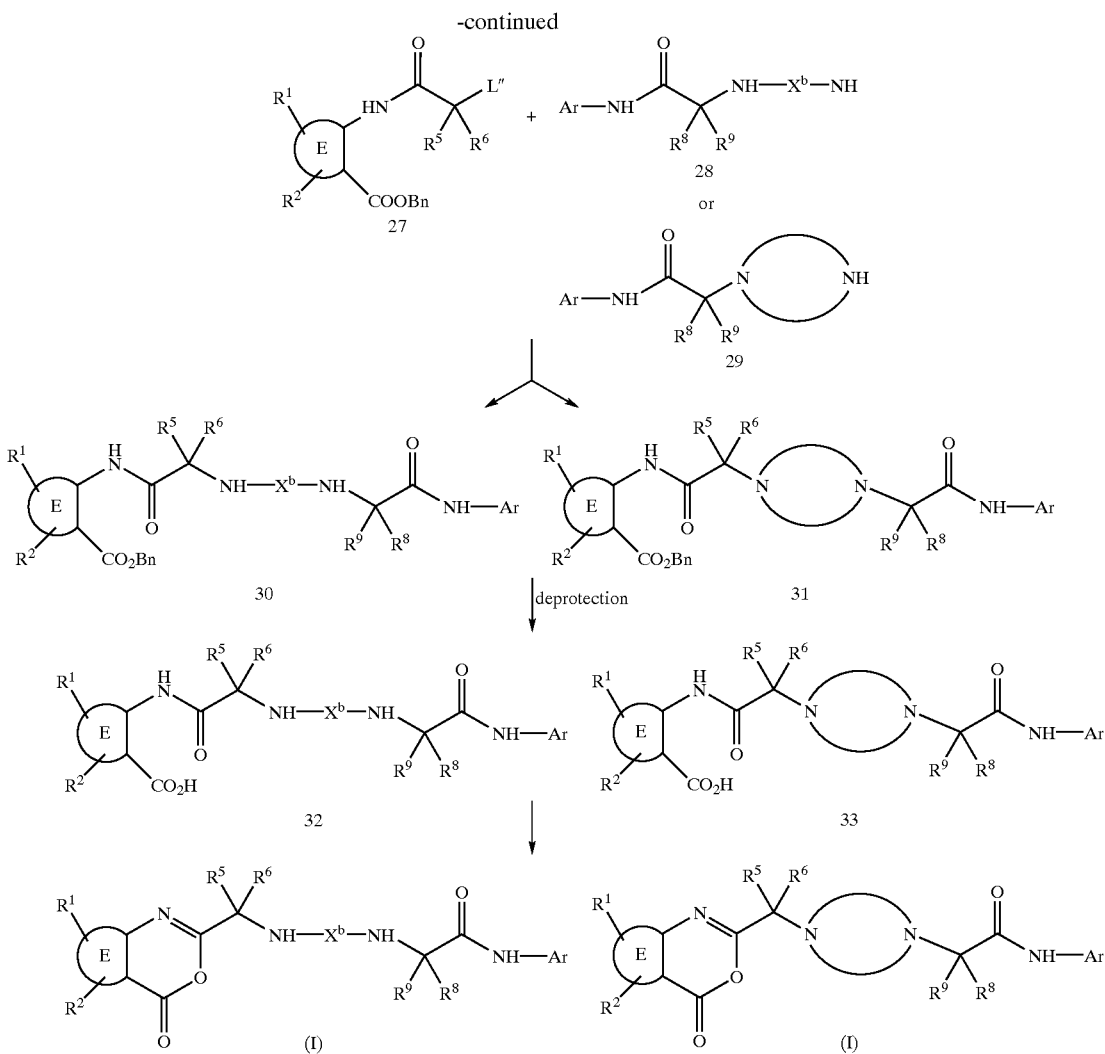

Reaction of acid chloride 15 with benzylalcohol in the presence of base such as diisopropylethyl amine, triethylamine, and the like provides a compound of formula 25. The reaction is carried out in inert organic solvent such as dichloromethane. Reduction of the nitro group under catalytic hydrogenation reaction conditions, followed by treatment of the resulting amine with a compound of formula 18 provides a compound of formula 27. The reaction is carried out under the reaction conditions described above. Treatment of 27 with a compound of formula 28 or 29 provides a compound of formula 30 or 31 respectively. Removal of the benzyl group under catalytic hydrogenation reaction conditions followed by cyclization of compound 32 or 33 provides a compound of Formula (I) where G is —O—. The cyclization reaction is carried out in the presence of 1-hydroxy-7-azabenzotriazole (HOAT) and N-[(dimethylamino)-1H-1,2,3-triazolo[4,5-b]pyridin-1-ylmethylene]-N-methyl-methanaminium hexafluorophosphate N-oxide (HATU) in polar organic solvent such as a mixture of dimethylformamide and tetrahydrofuran.

Compounds of Formula (I) can be prepared from other compounds of Formula (I). Some such methods are described below:

(a) A compound of Formula (I) where $L_1$ is a group of formula (a) where G is —$NR^7$— and $R^3$ and $R^4$ together with the carbon atom to which they are attached form —C=O and $L_2$ is a group of formula Ar—W— where W is —NH—C(O)[$CR^8R^9$]— can be prepared from a corresponding compound of Formula (I) where G is —O— as shown in described in Scheme E below.

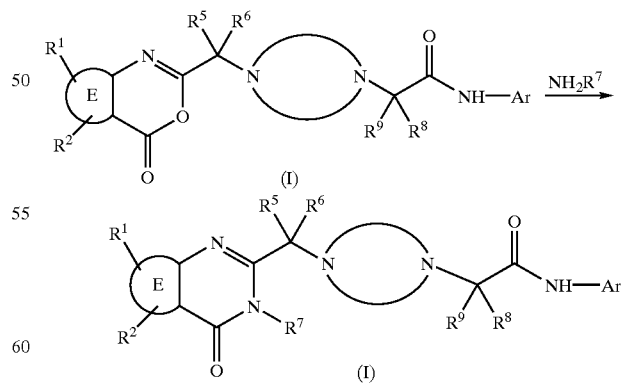

A compound of Formula (I) wherein $L_1$ is a group of formula (a) where G is —O— can be converted to a corresponding compound of Formula (I) where G is —$NR^7$— where $R^7$ is as defined in the Summary of the Invention by either:

i) heating compound (I) where G is —O— with an amine of formula $NH_2R^7$ in a non-nucleophilic organic base such as pyridine; or (ii) heating compound (I) where G is —O— with an amine of formula $NH_2R^7$ in the presence of glacial acetic acid in a high boiling organic solvents such as dioxane; or (iii) heating compound (I) where G is —O— first with an amine of formula $NH_2R^7$ alone, and then in the presence of an acid such as glacial acetic acid. Suitable solvents are high boiling organic solvents such as dioxane. This is the preferred route.

(b) A compound of Formula (I) where $R^1$ and/or $R^2$ are hydroxy can be converted to a corresponding compound of Formula (I) where $R^1$ and/or $R^2$ are alkoxy by reacting with an alkyl halide in the presence of a base.

(c) The $R^7$ group in a compound of Formula (I) can also be transformed to give corresponding compounds of Formula (I) with different $R^7$ group. For example, compound (I) where $R^7$ is —$CH_2COOH$ can be converted to corresponding compound (I) where $R^7$ is —$CH_2COR$ where R is heterocycle, cycloalkyl, heteroaryl by following the procedures described in *J. Indian Chem. Soc.*, Vol. LIX, pages 1196, 1982.

A wide variety of linkers are commercially available (see, e.g., Chem Sources USA and Chem Sources International; the ACD electronic database; and Chemical Abstracts). Many of the linkers that are suitable for use in this invention fall into this category. Others can be readily synthesized by methods known in the art.

Other methods and examples for preparing compounds of this invention are disclosed in Applicants co-pending U.S. patent application Ser. No. 09/671,626 filed on even date herewith the disclosure of which is incorporated herein in its entirety.

Utility

The compounds of Formulae (I) are useful in modulating the activity of voltage-gated $Na^+$ channels in mammals, e.g., humans. They will typically be used for the prevention and alleviation of pain, e.g., for topical anesthesia, infiltration anesthesia, field block anesthesia, nerve block anesthesia, spinal anesthesia, epidural anesthesia, post-operative analgesia, post-arthroscopic pain management, inflammatory pain, neuropathic pain, depression, seizure (epilepsy) and neuroprotection (stroke) and are useful for other indications, e.g., protection and recovery from ischemia (Lantos et al, *Int. Pharmacodyn. Ther.* 331: 179 (1996)), asthma (Hunt et al., *Mayo Clin. Proc.* 71: 361 (1996), rapid heartbeat (Gorgels et al. *Am. J. Cardiol.* 78: 43 (1 996)), cardiac arrhythmia (Rosen et al, *Am. Heart J.* 89: 526 (1975), natriuresis (Wyeth et al, *Life Sci.* 60: 473 (1997) proctitis and active distal ulcerative colitis (Arlander et al, *Aliment. Pharmacol. Ther.* 10: 73 (1996)), inflammatory bowel disease and irritable bowel syndrome.

Testing

Local anesthetics can be tested for activity in various well-known assays (e.g., the batrachotoxin (BTX) displacement assay (McNeal et al., *J. Med. Chem.* 28: 381 (1985)), patch clamp method (see, Neher and Sakmann, "The Patch Clamp Technique "*Scientific American*" pp. 44–51 (1992); Hamill et al., *Pflügers Arch.* 391:85 (1981); intact isolated nerve assay, e.g., isolated frog sciatic nerve (see Example 13 described below); blockage of the cutaneous trunci muscle reflex (CTMR) in guinea pigs (Bulbring et al.,*J. Pharmacol. Exp. Therap.* 85: 78–84 (1945); Blight et al, *J. Compar. Neurology* 296: 614–633 (1990); Choi et al., *Life Sci.* 61: PL177-84 (1997)). Evaluation of motor and sympathetic function during sciatic nerve block in the rat is described, e.g., in Grant et al., *Anesth. Analg.* 75: 889–94 (1992), and Thalhammer et al., *Anesthesiology* 82: 1013–25 (1995).

The compounds in the compound table were screened for voltage-gated $Na^+$ ion channel binding and functional activities as exemplified in Biological Examples 1–5 below.

Pharmaceutical Formulations

When employed as pharmaceuticals, the compounds of Formula (I) are usually administered in the form of pharmaceutical compositions. This invention therefore provides pharmaceutical compositions which contain, as the active ingredient, one or more of the compounds of Formula (I) above or a pharmaceutically acceptable salt thereof and one or more pharmaceutically acceptable excipients, carriers, diluents, permeation enhancers, solubilizers and adjuvants. One or more compounds of Formula (I) may be administered alone or in combination with other therapeutic agents (e.g., vasoconstrictors, anti-inflammatory agents, antibiotics, other local anesthetic bases and salts, counter-irritants), carriers, adjuvants, permeation enhancers, and the like. The compounds may be formulated using conventional techniques such as those described in *Remington's Pharmaceutical Sciences*, Mace Publishing Co., Philadelphia, Pa. $17^{th}$ Ed. (1985) and "*Modern Pharmaceutics*," Marcel Dekker, Inc. $3^{rd}$ Ed. (G. S. Banker & C. T. Rhodes, Eds.). Pharmaceutically acceptable salts of the active agents (e.g., acid addition salts) may be prepared using standard procedures known to those skilled in the art of synthetic organic chemistry and described, e.g., by J. March, *Advanced Organic Chemistry:* Reactions, Mechanisms and Structure, $4^{th}$ Ed. (New York: Wiley-Interscience, 1992).

The compounds of Formula (I) may be administered by any of the accepted modes of administration of agents having similar utilities, for example, by oral, topical, or by parenteral routes (e.g., intradermal, intravenous, subcutaneous, intramuscular), intra-articular, intraspinal, epidural , rectal, vaginal, or transdermal/transmucosal routes. The most suitable route will depend on the nature and seventy of the condition being treated. Subcutaneous, intradermal and percutaneous injections (intended to deliver the agent in close proximity to a peripheral nerve trunk) are preferred routes for the compounds of this invention. In making the compositions of this invention, the active ingredient is customarily diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Alternatively, the compounds of this invention may be solubilized and encapsulated (e.g., in a liposome or a biodegradable polymer), or used in the form of microcrystals coated with an appropriate nontoxic lipid (see, e.g., P. J. Kuzma et al, *Regional Anesthesia* 22 (6): 543–551 (1997).

The compositions may be formulated to provide for drug latentation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across tissue barriers.

These compositions may be formulated as oral sprays. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

For topical use, the compositions can be in the form of emulsions, creams, jelly, solutions, ointments containing, for example, up to 5% by weight of the active compound. For parenteral administration, the compositions can be in the form of sterile injectable solutions and sterile packaged powders. Preferably, injectable solutions are formulate at a pH of 4.5±0.3. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, *Regional Anesthesia* 22 (6): 543–551 (1997), all of which are incorporated herein by reference.

Another preferred formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252; 5,719,197; and 4,992,445, all of which are incorporated herein by reference. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., an ampoule).

The compounds of the present invention, or their pharmaceutically acceptable salts, are administered in a therapeutically effective amount. The duration of action and/or potency of such compounds will be increased by comparison with local anesthetics, thus dosage and dosing schedule must be adjusted accordingly. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

The following formulation examples illustrate representative pharmaceutical compositions of the present invention and should not be considered as limiting in any way the invention being disclosed. In particular, a vasoconstrictor, preferably epinephrine, may be added to the following formulations. Additionally, a conventional local anesthetic, preferably lidocaine, may be added to the formulations of this invention.

Formulation Example 1

| Solution for Injection | |
|---|---|
| Ingredient | Quantity |
| Sodium Chloride | 0.9% (0.9 g/100 mL) |
| Methylparaben | 1 mg/mL |
| Compound of Formula (I) | 0.5% (0.5 g/100 mL) |
| Water for injection | to 100 mL |

Formulation Example 1B

| Solution for Injection | |
|---|---|
| Ingredient | Quantity |
| Compound of formula (I) | 20 mg (di-HCl salt) |
| Mannitol | 15.7 mg |
| Sucrose | 37.1 mg |
| 0.1M NaOH | qs. pH 4.7–4.8 |
| 0.1M HCl | qs. pH 4.7–4.8 |
| Water for injection | qs. to 1 mL |

Formulation Example 1C

| Solution for Injection | |
|---|---|
| Ingredient | Quantity |
| Compound of formula (I) | 20 mg (di-HCl salt) |
| 0.85% (Isotonic) Saline Solution | qs. to 1 mL |
| 0.1M NaOH | qs. pH 4.7–4.8 |
| 0.1M HCl | qs. pH 4.7–4.8 |

Formulation Example 2

| Paste | |
|---|---|
| Ingredient | Quantity (%) |
| Compound of Formula (I) | 1 |
| Zinc oxide | 25 |
| Starch | 25 |
| Calamine | 5 |
| White petrolatum | to 100 |

Formulation Example 3

| Ointment | |
|---|---|
| Ingredient | Quantity (%) |
| Compound of Formula (I) | 10 |
| White petrolatum | to 100 |
| White wax | 5 |

Formulation Example 4

| Cream | |
|---|---|
| Ingredient | Quantity (%) |
| Compound of Formula (I) | 0.5 |
| Oleaginous phase | |
| Spermaceti | 12.5 |
| White wax | 12.0 |
| Almond oil | 55.5 |
| Aqueous phase | |
| Sodium borate | 0.5 |
| Stronger rose water | 2.5 |
| Purified water | 16.5 |
| Aromatic Rose oil | 0.02 |

Formulation Example 5

| Gel | |
|---|---|
| Ingredient | Quantity (%) |
| Compound of Formula (I) | 2 |
| Methocel 90 H.C. 4000 | 0.8 |
| Carbopol 934 | 0.24 |
| Propylene glycol | 16.7 |
| Methylparaben | 0.015 |
| Purified water | to 100 |

Formulation Example 6

Preparation of Injectable Formulation

The dihydrochloride salt of Compound 1 (2.2 grams) was dissolved in 50 mL of water. The pH was adjusted to 4.75 by slow addition of 0.1 M NaOH with very efficient stirring (pH adjustment may require up to 4 hours, since during the addition of 0.1 M NaOH, compound 1 precipitates heavily and re-dissolves very slowly). About 17–18 mLs of 0.1 M NaOH are needed for the pH adjustment. Mannitol (1.57 grams) and sucrose (3.71 grams) were then dissolved in the above solution. The volume was adjusted to 95 mL with water and the pH was adjusted with 0.1 M NaOH and/or 0.1 M HCl to 4.7–4.8, if necessary. The volume was then adjusted to 100 mL with water and the formulation was sterile filtered under aseptic conditions.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

The following abbreviations have the following meanings. If an abbreviation is not defined, it has its generally accepted meaning.

| | | |
|---|---|---|
| BTX | = | batrachotoxin |
| DIPEA | = | diisopropylethylamine, Hunig's base |
| DMF | = | N,N-dimethylformamide |
| DMSO | = | dimethylsulfoxide |
| HATU | = | 6-(7-azabenzotriazol-1-yl)-N,N,N'N'-tetramethyluronium hexafluorophosphate |
| HOAT | = | 1-hydroxybenzotriazole |
| HOAT | = | 1-hydroxy-7-azabenzotriazole |
| TFA | = | trifluoroacetic acid |
| THF | = | tetrahydrofuran |
| $CH_2Cl_2$ | = | methylene chloride |
| MeOH | = | methanol |
| EtOAc | = | ethyl acetate |
| NaOH | = | sodium hydroxide |

Synthetic Examples

Example 1

Preparation of a compound (I) where $L_1$ is a group of formula (a) where $R^1$ is hydrogen, $R^2$ is methyl, G is $-NR^7-$ where $R^7$ is $-CH_2CO$morpholine and $R^3$ and $R^4$ together with the carbon atom to which they are attached form $-C=O$ and $L_2$ is a group of formula Ar—W— where Ar—W is 2-methylphenyl-NH—C(O)*CH($CH_2CH_3$)— where *C=(R) and further wherein both $L_1$ and $L_2$ are attached to the linker, X, via 1,4,10,13-tetraoxa-7,16-diazacyclooctadecane following FIG. 1

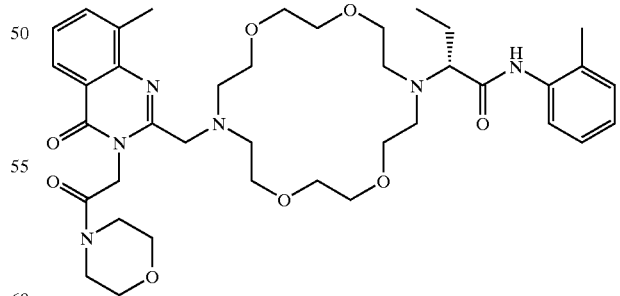

Step 1

Carbobenzyloxyglycine 34 (25.8 g, 123 mmol, 1.0 equiv.), 1-hydroxy-7-azabenzotriazole (HOAT) (3.36 g, 24.7 mmol, 0.2 equiv.) and N-[(dimethylamino)-1H-1,2,3,-triazolo[4,5-b]pyridin-1-ylmethylene]-N-methylmethanaminium hexafluorophosphate N-oxide (HATU) (46.9 g, 123 mmol, 1.0 equiv.) were added to N,N-dimethylformamide (DMF) (500 ml) in a 1-liter 2-necked round bottom flask equipped with a magnetic stir bar under a nitrogen atmosphere. The solution was cooled to 0° C. using an ice bath. N,N-diisopropylethylamine (DIPEA) (32.2 ml, 185 mmol, 1.5 equiv.) was added all at once to the stirred reaction mixture. This was followed by the addition of morpholine (10.8 ml, 123 mmol, 1.0 equiv.). The reaction mixture was warmed to room temperature and stirring was continued. After 8 h, the reaction mixture was poured into a stirred solution of sodium chloride (100 g) in water (3 1) and ice (1.5 1), resulting in precipitation of the product. The suspension was stirred for 1 h after which time the precipitate was isolated by filtration using a Buchner funnel and thoroughly rinsed with water (2 1). The solid was dried in vacuum to give compound 35 (31.4 g, 91.6%) as a white solid with >95% purity ($^1$H NMR in DMSO).

Step 2

A solution of compound 35 (31.4 g, 113 mmol, 1.0 equiv.) in methanol (MeOH) (100 ml) and THF (300 ml) was added to a 1-liter Parr bottle containing 10% palladium on carbon (4.0 g) and tetrahydrofuran (THF) (100 ml) under nitrogen. The Parr bottle was degassed under vacuum, filled with hydrogen gas. Hydrogenation was carried out at 35 psi for 1 h. The reaction mixture was filtered through filter paper using a Buchner funnel and thoroughly rinsed with THF:MeOH (1:1) (300 ml). The filtrate was concentrated to dryness on a rotary evaporator to give compound 36 (16.2 g, 99.6%) as a white solid with >95% purity.

Step 3

3-Methyl-2-nitrobenzoic acid 37 (30.0 g, 166 mmol, 1.0 equiv.) was added to $CH_2Cl_2$ (150 ml) in a 1-liter round bottom flask equipped with a magnetic stir bar under a nitrogen atmosphere. The resulting suspension was cooled to 0° C. in an ice bath. Oxalyl chloride (2.0 M in $CH_2Cl_2$, 166 ml, 332 mmol, 2.0 equiv.) was added to the stirred reaction mixture through a pressure equalizing dropping funnel over 30 min. DMF (10 drops) was added slowly and the reaction mixture was allowed to warm up to room temperature. After 30 min., the suspended material dissolved to give a homogeneous solution and effervescence stopped. The reaction mixture was concentrated to dryness on a rotary evaporator. The solid material was re-dissolved in $CH_2Cl_2$ (200 ml) and was concentrated to dryness on a rotary evaporator to give compound 38 (32.9 g, 99%) as an off white solid Step 4

A solution of compound 38 (26.9 g, 135 mmol, 1.2 equiv.) in $CH_2Cl_2$ (200 ml) in a 1-liter round bottom flask equipped with a magnetic stir bar, was cooled to 0° C. using an ice bath under a nitrogen atmosphere. After adding DIPEA (29.4 ml, 169 mmol, 1.5 equiv.), a solution of compound 36 (16.2 g, 113 mmol, 1.0 equiv.), prepared in step 2 above, in $CH_2Cl_2$ (200 ml) was added dropwise over 1 h using a pressure equalizing dropping funnel. The reaction mixture was warmed to room temperature and stirring was continued for 0.5 h. The reaction mixture was poured into a separatory funnel and washed with saturated sodium bicarbonate ($NaHCO_3$) (250 ml). Washing with $NaHCO_3$ was repeated three times. The organic layer was separated and washed once with saturated sodium chloride (NaCl) (200 ml), dried over anhydrous magnesium sulfate ($MgSO_4$) (20 g), filtered through filter paper using a Buchner funnel. The residue thoroughly rinsed with $CH_2Cl_2$ (200 ml). The combined filtrate was concentrated to dryness on a rotary evaporator. The residue was purified using a silica gel plug using 98:2 $CH_2Cl_2$:MeOH (500 ml) as the eluent to give compound 39 (32.8 g, 95.0%) as a white solid with >95% purity.

Step 5

A solution of compound 39 (35.5 g, 116 mmol, 1.0 equiv.) in THF (300 ml) was added to a 1-liter Parr bottle containing 10% palladium on carbon (4.5 g) and tetrahydrofuran (THF) (100 ml) under $N_2$. The Parr bottle was degassed under vacuum, filled with hydrogen gas and hydrogenation was carried out at 35 psi for 2 h. The reaction mixture was filtered through filter paper using a Buchner funnel and the residue was thoroughly rinsed with THF (300 ml). The filtrate was concentrated to dryness on a rotary evaporator to give compound 40 (31.83 g, 99.1%) as a white solid with >95% purity ($^1$H NMR in DMSO).

Step 6

A solution of aniline 40 (20.0 g, 72.2 mmol, 1.0 equiv.) in acetic acid (64.0 ml) was cooled to 10° C. using a cold water bath. Chloroacetyl chloride (6.33 ml, 79.4 mmol, 1.1 equiv.) was added, followed by the addition of a solution of sodium acetate (24.8 g) in water (126 ml). The reaction was allowed to warm to room temperature over 20 min. The reaction mixture was filtered through filter paper using a Buchner funnel and the solid was thoroughly rinsed with water (3 1). The solid was dried in vacuum to give compound 41 (20.12 g, 78.8%) as a white solid with 99% purity.

Step 7

(R)-(+)-2-aminobutyric acid 42 (100 g, 970 mmol, 1.0 equiv.) was dissolved in 2 N sodium hydroxide (NaOH) (500.0 ml) contained in a 2-liter 3-necked round bottom flask equipped with a magnetic stir bar under nitrogen atmosphere. The solution was cooled to 0° C. using an ice bath. Benzyl chloroformate (166 ml, 1160 mmol, 1.2 equiv.) and 2 N NaOH (800 ml) were added alternately in small portions (approximately ten portions each). The ice bath was then replaced by a 20° C. water bath, and vigorous stirring was continued for an additional hour. The reaction mixture was extracted three times with ether (500 ml each) and discarded. The aqueous layer was made acidic by the addition of 3 N hydrochloric acid (HCl) (400 ml) and extracted three times with ether (500 ml each). The combined ether layers were washed once with saturated sodium chloride (NaCl) (400 ml), dried over anhydrous magnesium sulfate ($MgSO_4$) (80 g), filtered through filter paper using a Buchner funnel and the residue was thoroughly rinsed with ether (500 ml). The filtrate was concentrated to dryness on a rotary evaporator to give compound 43 (228 g, 99 %) as a white solid with >95% purity.

Step 8

Carbobenzyloxy-(R)-2-aminobutyric acid 43 (40.0 g, 169 mmol, 1.0 equiv.), 1-hydroxy-7-azabenzotriazole (HOAT) (4.59 g, 33.8 mmol, 0.2 equiv.) and N-[(dimethylamino)-1H-1,2,3,-triazolo[4,5-b]pyridin-1-ylmethylene]-N-methylmethanaminium hexafluorophosphate N-oxide (HATU) (64.2 g, 169 mmol, 1.0 equiv.) were dissolved in N,N-dimethylformamide (DMF) (350 ml) in a 1-liter 2-necked round bottom flask equipped with a magnetic stir bar under nitrogen atmosphere. The solution was cooled to 0° C. using an ice bath. N,N-diisopropyl-ethylamine (DIPEA) 44.1 ml, 253 mmol, 1.5 equiv.) was added, followed by the addition of o-toluidine 44 (18.0 ml, 169 mmol, 1.0 equiv.). The reaction mixture was warmed to room temperature and stirring continued for 8 h. The reaction mixture was poured into a stirred solution of sodium chloride (500 g) in water (3 1) and ice (1.5 1), causing the product to precipitate. The precipitates were filtered through a Buchner funnel and thoroughly rinsed with water (2 1). The solid was dried in vacuum to give compound 45 (51.2 g, 93%) as a white solid with >95% purity.

Step 9

Compound 45 (55.0 g, 162 mmol, 1.0 equiv.) was dissolved in MeOH (250 ml) and THF (200 ml) and added to a 1-liter Parr bottle containing 10% palladium on activated carbon (5.8 g) and tetrahydrofuran (THF) (100 ml) under nitrogen. The bottle was degassed and filled with hydrogen. Hydrogenation was carried out at 35 psi for 1 h. The reaction mixture was filtered through filter paper using a Buchner funnel and the residue was thoroughly rinsed with 50% THF, 50% MeOH (300 ml). The filtrate was concentrated to dryness on a rotary evaporator to give compound 46 (32.6 g, 98%) as a white solid with >95% purity.

Step 10

Benzylamine 47 (40.0 g, 373 mmol, 1.0 equiv.) and 1,2-bis-(2-iodoethoxy)-ethane 48 (414.3 g, 1120 mmol, 3.0 equiv.) were dissolved in ethanol (EtOH) (200 ml) contained in a 1-liter 1-necked round bottom flask equipped with a magnetic stir bar and reflux condenser. N,N-diisopropylethylamine (DIPEA) (162.6 ml, 933 mmol, 2.5 equiv.) was added and the reaction mixture was warmed to 70° C. After 8 h, the reaction mixture was cooled to room temperature at which time crystallization of byproducts occurred. To help precipitation of these salts, hexanes (500 ml) was added to the stirred suspension. The salts were filtered off using a Buchner funnel and rinsed with hexanes (1 l). The filtrate was concentrated to a thick oil on a rotary evaporator. The residue was purified using a silica gel plug to give compound 49 (63.4 g, 28.7%) as a yellow oil with >95% purity.

Step 11

A solution of compound 49 (9.6 g, 50 mmol, 1.0 equiv.), prepared as described in Step 9 above, compound 46 (36.8 g, 62.2 mmol, 1.25 equiv.), prepared as described in Step 10 above, sodium iodide (3.8 g, 25 mmol, 0.5 equiv.), and sodium carbonate (26.5 g, 250 mmol, 5.0 equiv.) in acetonitrile (992 ml, 0.05 M) was divided among 32 sealed tubes each equipped with a magnetic stir bar under nitrogen. The reaction mixture was warmed to 120° C. and stirring was continued for 12 h. The reaction mixture was cooled to room temperature. The contents of the tubes were poured into a round bottom flask (2 l) and the tubes were thoroughly rinsed with acetonitrile to recover all residue (including the insoluble salts). The suspension was concentrated to a thick suspension and the residue was partitioned between water (200 ml) and EtOAc (300 ml). The water layer was extracted with EtOAc (100 ml). The combined organic layers were dried over anhydrous magnesium sulfate ($MgSO_4$) (30 g), filtered through filter paper using a Buchner funnel and the residue was thoroughly rinsed with EtOAc (100 ml). The filtrate was concentrated to dryness on a rotary evaporator. The resulting material was purified by preparatory HPLC ((Varian ROOPK201K8 (8 μm) column (100 mm×250 mm) with a flow rate of 250 ml/min. Product eluted at 28% acetonitrile/water and was detected by UV absorbency at 214 nm). Product was isolated by removing the water:acetonitrile mixture on a rotary evaporator and partitioning the residue with 3 N NaOH (50 ml). The product was extracted with EtOAc (2×200 ml) and the combined organic layers were washed once with saturated sodium chloride (NaCl) (100 ml), dried over anhydrous magnesium sulfate ($MgSO_4$) (40 g), and filtered through filter paper using a Buchner funnel. The residue was thoroughly rinsed with EtOAc (100 ml) and the filtrate was concentrated to dryness on a rotary evaporator to give compound 50 (11.3 g, 42.8 %) as a clear oil with >95% purity.

Step 12

Compound 50 (5.0 g, 9.5 mmol, 1.0 equiv.) was dissolved in MeOH (100 ml) and added to a 1-liter Parr bottle containing 10% Palladium on activated carbon (5.0 g) and methanol (MeOH) (100 ml) under nitrogen. The Parr bottle was degassed under vacuum and filled with hydrogen gas. Debenzylation was carried out at 35 psi for 12 h. The reaction mixture was filtered through filter paper using a Buchner funnel and thoroughly rinsed with MeOH (300 ml). The filtrate was concentrated to dryness on a rotary evaporator to give compound 51 (3.5 g, 85%) as a white solid with >95% purity.

Step 13

Compound 41 (8.9 g, 25.3 mmol, 1.3 equiv.), prepared in Step 6 above, compound 51 (8.5 g, 19.5 mmol, 1.0 equiv.), prepared in Step 12 above, EtOH (15 ml), DMF (18 ml) and N,N-diisopropylethylamine (DIPEA) (5.1 ml, 29.2 mmol, 1.5 equiv.) were combined and then divided equally into three pressure tubes, each containing a magnetic stir bar. The tubes were sealed and heated to 120° C. with stirring for 5 h. The contents of the tubes were combined in a separatory funnel and partitioned between 1 N HCl (200 ml) and EtOAc (500 ml). The aqueous layer was washed with EtOAc (4×400 ml). The acidic layer was made basic (pH>10) with the addition of 3 N NaOH (300 ml) and extracted with EtOAc (1×400 ml). The EtOAc layer was washed once with saturated sodium bicarbonate ($NaHCO_3$) (250 ml) and once with saturated sodium chloride (NaCl) (200 ml). The solution was dried over anhydrous magnesium sulfate ($MgSO_4$) (50 g), filtered through filter paper using a Buchner funnel and the residue thoroughly rinsed with EtOAc (200 ml). The filtrate was concentrated to dryness on a rotary evaporator. The product was partially purified using a silica gel plug ((elution gradient: $CH_2Cl_2$ (500 ml), 2:98 MeOH:$CH_2Cl_2$ (500 ml) and then 5:95 MeOH:$CH_2Cl_2$ (500 ml)). The organic solvents were concentrated and the resulting material was loaded onto a preparatory HPLC for further purification ((Varian ROOPK201K8 (8 μm) column (100 mm×250 mm) with a flow rate of 250 ml/min. The product eluted with 28% acetonitrile/water and was detected by UV absorbency at 214 nm)). The water:acetonitrile mixture was concentrated on a rotary evaporator. The residue was partitioned with 3 N NaOH (25 ml), extracted with EtOAc (2×150 ml). The combined EtOAc layers were washed with saturated sodium chloride (NaCl) (100 ml), dried over anhydrous magnesium sulfate ($MgSO_4$) (20 g), and filtered through filter paper using a Buchner funnel. The filtrate was concentrated to dryness on a rotary evaporator to give compound (I) (6.0 g, 41.9%) as a clear oil with >98% purity (analytical HPLC). The bis-hydrochloride salt was prepared by dissolving the oil in MeOH (3 ml), adding 4.0 N HCl in dioxane (20 ml, 5.0 equiv.). After stirring for 5 min., the solution was dripped into ether (1000 ml) with vigorous stirring in order to precipitate the product. Approximately 800 ml of the ether was decanted and the product was isolated from the remaining suspension by filtration using a Buchner funnel. The product was thoroughly rinsed with ether (300 ml), dried under vacuum, and dissolved in 20:80 acetonitrile:water (500 ml). The solution was frozen using a dry ice-acetone bath, and lyophilized to give compound (I) dihydrochloride salt as a white powder.

Example 2

Preparation of a compound (I) where $L_1$ is a group of formula (a) where $R^1$ is hydrogen, $R^2$ is methyl, G is —$NR^7$— where $R^7$ is —$CH_2$COmorpholin-4-yl and $R^3$ and $R^4$ together with the carbon atom to which they are attached form —C=O and $L_2$ is a group of formula Ar—W— where Ar—W is 2-methylphenyl-NH—*C(O)CH($CH_2CH_3$)— where *C=(RS) and further wherein both $L_1$ and $L_2$ are attached to the linker, X, via 1,4,10,13-tetraoxa-7,16-diazacyclooctadecane following FIG. 2

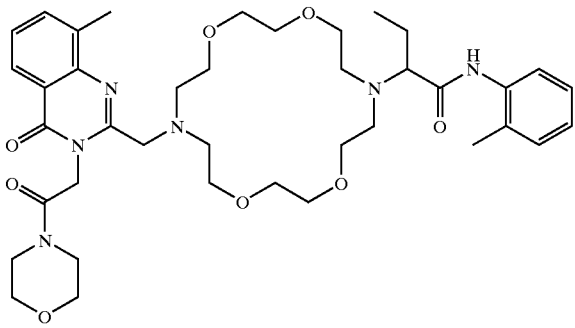

Step 1

To a solution of 1,4,10,13-tetraoxa-7,16-diazacyclooctadecane 52 (50.0 g, 0.19 mol) in 1,4-dioxane (700 ml) was added a solution of di-tert-butyl dicarbonate 41.5 g, 0.19 mol) in 1,4 dioxane (100 ml) over 1 h. After stirring overnight, dioxane was removed in vacuo and water (200 ml) was added to the remaining slurry with vigorous stirring. The white precipitate was removed by filtration (28 g of bis-Boc-18-crown-6) and the filtrate was lyophilized to dryness. Trituration of the solid with $CH_2Cl_2$ afforded compound 53 (32g, 46% yield) as a white solid.

Step 2

α-Bromobutyryl bromide (80 ml, 0.66 mol) was added to an ice cold mixture (~15° C.) of o-toluidine 44 (64 ml, 0.60 mol) and glacial acetic acid (520 ml) in a 2 1 flask. The reaction mixture was stirred vigorously and a cold solution of sodium acetate trihydrate (204 g) in water (1100 ml) was added. A white precipitate began to form instantly. After 30 min., the solid was filtered off, washed with water and dried to give compound 54 (200 g, 80%) as a white solid.

Step 3

A solution of α-bromo-n-butyryl-o-toluidine 54 (10.5 g, 0.04 mol), N,N-diisopropylethylamine ( 7.0ml, 0.04 mol) in ethanol (15 ml) was added to a 35 ml pressure tube containing N-boc-4,13-diaza-18-crown-6 53 (7.5 g, 0.02 mol). The tube was closed and immersed into an oil bath maintained at 120° C. After 36 h, the reaction mixture was cooled and the organics were evaporated in vacuo. The oily residue was purified by elution through a plug of silica using 1% methanol/dichloromethane as the eluent. The organics were removed to give the desired product as well as unreacted α-bromo-n-butyryl-o-toluidine. The crude product was dissolved in 50% trifluoroacetic acid/dichloromethane (50 ml). After stirring for 30 min. the reaction mixture was concentrated to a thick oil, redissolved in water (100 ml) and extracted with ethyl acetate (3×100 ml) to remove residual α-bromo-n-butyryl-o-toluidine. The aqueous solution was then basified to pH 10 with 1N NaOH and the desired product was extracted with ethyl acetate (3×100 ml). The ethyl acetate layer was washed with brine, dried over anhydrous sodium sulfate, filtered and concentrated in vacuo to give compound 55 (6.0 g, 66% of theory) as a thick light yellow oil. MS: M+H▽438.

Step 4

Compound 41 (8.9 g, 25.3 mmol, 1.3 equiv.), prepared as described in Example 1, Steps 1–6, compound 55 (8.5 g, 19.5 mmol, 1.0 equiv.), prepared as described in Step 3 above, EtOH (15 ml), DMF (18 ml) and N,N-diisopropylethylamine (DIPEA) (5.1 ml, 29.2 mmol, 1.5 equiv.) were combined and then divided equally into three pressure tubes, each containing a magnetic stir bar. The tubes were sealed and heated to 120° C. with stirring. After 5 h, the contents of the tubes were combined in a separatory funnel and partitioned between 1 N HCl (200 ml) and EtOAc (500 ml). The aqueous layer was washed with EtOAc (4×400 ml). The acidic layer was made basic (pH>10) with the addition of 3 N NaOH (300 ml) and extracted with EtOAc (1×400 ml). The EtOAc layer was washed with saturated sodium bicarbonate ($NaHCO_3$) (250 ml) and saturated sodium chloride (NaCl) (200 ml). The solution was dried over anhydrous magnesium sulfate ($MgSO_4$) (50 g), filtered through filter paper using a Buchner funnel and the residue thoroughly rinsed with EtOAc (200 ml). The filtrate was concentrated to dryness on a rotary evaporator. The crude product was partially purified using a silica gel plug (a Buchner funnel was filled with a slurry of silica gel in $CH_2Cl_2$ (200 ml). A solution of impure product (15 g) in $CH_2Cl_2$ (10 ml) was loaded onto the plug and a vacuum was applied to draw the solution into the silica gel plug. The plug was eluted with $CH_2Cl_2$ (500 ml) using vacuum to pull solvent through the plug. The plug was eluted with 2:98 MeOH:$CH_2Cl_2$ (500 ml) and then eluted with 5:95 MeOH:$CH_2Cl_2$ (500 ml) until all product had eluted. The purified fractions were combined and concentrated to dryness on a rotary evaporator. [This plug was used to remove all polar material before loading onto a preparatory HPLC]. The resulting material was purified by HPLC as described in Example 1, Step 13 above to provide the desired compound of Formula (I).

Proceeding as described in Example 2 above but substituting appropriate starting material following compounds were prepared:

Compound Nos. as identified in the compound table above: 2, 3, 3, 4, 6, 7, 8, 14, 16, 17, 18, 19, 34, 36, 37, 38, 39, and 40.

Example 3

Preparation of a compound (I) where $L_1$ is a group of formula (b) where $R^1$ is hydrogen, $R^2$ is methyl, G is —O—, and $R^3$ and $R^4$ together with the carbon atom to which they are attached form —C═O and $L_2$ is a group of formula Ar—W— where Ar—W is 2-methylphenyl-NH—C(O)*CH ($CH_2CH_3$)— where *C═(RS) and further wherein both $L_1$ and $L_2$ are attached to the linker, X, via 1,4,10,13-tetraoxa-7,16-diazacyclooctadecane following FIG. 3

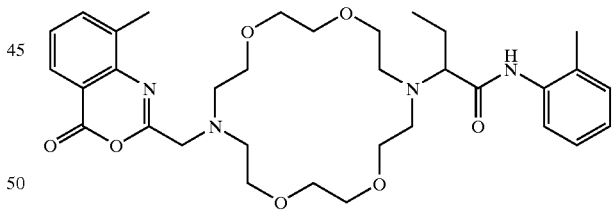

Step 1

Benzyl alcohol (39 g, 361 mmol) in dichloromethane (410 ml) was added slowly to a solution of 3-methyl-2-nitro-benzoylchloride 56 (71g, 356 mmol) and diisopropylethylamine (93 ml, 534 mmol) in dichloromethane (410 ml) at 0° C. The reaction mixture was warmed to room temperature and stirred for 2 h. The solvents were evaporated and the residue was partitioned between ethyl acetate and saturated sodium bicarbonate. The organic phase was washed with brine, dried, filtered through a thin pad of silica gel and concentrated to afford 3-methyl-2-nitro-benzylbenzoate 57 (88 g, 91%) as a brown oil. 3-Methyl-2-nitro-benzylbenzoate 57 was converted to compound 59 by following the procedures described in Step 1, in Example 2 below.

Step 2

A solution of compound 59 (36 g, 113.4 mmol) and compound 55 (41 g, 93.8 mmol) prepared in Example 2 above and diisopropylamine (33 ml, 189.4 mmol) in acetonitrile (500 ml) was heated at 90° C. overnight. The solvents were evaporated and the residue was partititioned between ethyl acetate and 1N hydrochloric acid. Aqueous phase was basified to pH 10 with 20% (w/w) sodium hydroxide and the product was extracted with ethyl acetate. The organic phase was washed with brine, dried, filtered and concentrated to give compound 60 (67.5 g, 100%).

Step 3

A solution of compound 60 (67.5 g, 94 mmol) in methanol (1100 ml) was hydrogenated overnight, in the presence of palladium hydroxide on carbon (28 g). The reaction mixture was filtered and concentrated to afford compound 61 (56.5 g, 96%) as an off-white foam.

Step 4

A mixture of compound 61 (54.5 g, 87.3 mmol), O—(7-azabenzotriazol-1-yl)-N,N,N', N'-tetramethyluronium hexafluorophosphate (33.2 g, 87.3 mmol), 1-hydroxy-7-azabenzotriazole (5.94 g, 43.7 mmol) in DMF (44 ml) and THF (200 ml) was stirred at room temperature overnight. After aqueous work-up, The crude was purified by flash chromatography using $CH_3OH/CH_2Cl_2$ (1/99 to 10/90) to afford desired compound of Formula (I) (33.5 g, 70%) as an off-white solid.

Example 4

Preparation of a compound (I) where $L_1$ is a group of formula (a) where $R^1$ is hydrogen, $R^2$ is methyl, G is —$NR^7$— where $R^7$ is 2,3-dihydroxypropyl and $R^3$ and $R^4$ together with the carbon atom to which they are attached form —C=O and $L_2$ is a group of formula Ar—W— where Ar—W— is 2-methylphenyl-NH—C(O)*CH($CH_2CH_3$)— where *C=(RS) and further wherein both $L_1$ and $L_2$ are attached to the linker, X, via 1,4,10,13-tetraoxa-7,16-diazacyclooctadecane following FIG. 4

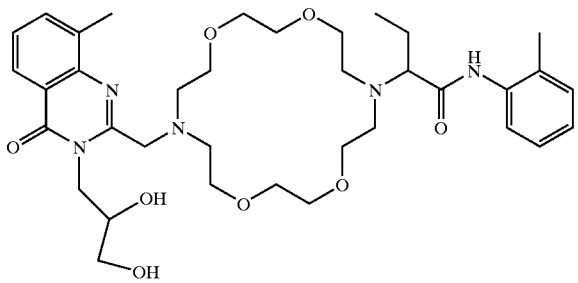

Step 1

Zinc was added portionwise to a solution of 3-methyl-2-nitro-benzylbenzoate 57 (88 g, 325 mmol) prepared as described in Example 3, Step 1 above, in glacial acetic acid (250 ml). During adding of zinc, the reaction temperature was maintained at <30° C. After addition, the reaction mixture was stirred at room temperature overnight. The reaction mixture was filtered and concentrated. The residue was partitioned between ethyl acetate and saturated sodium bicarbonate. The organic phase was washed with saturated sodium bicarbonate, brine, and dried over sodium sulfate. After filtration, the filtrate was concentrated and compound 58 was precipitated from ethyl acetate and hexane (62.4 g, 80%) as a light yellow solid.

Step 2

Chloroacetyl chloride (12 ml, 151 mmol) was added to a solution of compound 58 (30 g, 124 mmol) in glacial acetic acid (110 ml) kept in a cold water bath. The reaction mixture was stirred at room temperature for 15 min. A solution of sodium acetate (43 g, 316 mmol) in water (217 ml) was added and stirring was continued. After 30 min., the reaction mixture was filtered and the solid was dissolved in dichloromethane. The solution was washed with saturated sodium bicarbonate, dried, filtered, and concentrated to give compound 59 (39 g, 99%). Compound 59 was converted to a compound of Formula (I) where $L_1$ is a compound of formula (a) wherein G is oxygen (33.5 g, 70%) by following the procedures described in Example 3, Steps 2–4 above.

Step 3

A mixture of compound (I) (500 mg, 0.82 mmol) and 3-amino-1,2-propanediol (150 mg, 1.64 mmol) in dioxane (2 ml) was stirred at 100° C. in a sealed tube overnight. Glacial acetic acid (2 ml) was added and continued stirring at 100 ° C. overnight. The reaction mixture was partitioned between dichloromethane and 10% sodium hydroxide. The organic phase was washed with brine, dried, filtered, and concentrated. The crude product was purified by preparative HPLC. The pure fractions were combined and concentrated in vacuo. Saturated sodium bicarbonate was added and the product was extracted with dichloromethane. The organic layer was dried, filtered, concentrated and converted to its dihydrochloride salt by treating the free base with 4 N HCl solution in dioxane (200 mg, 32%).

Compound Nos. as identified in the compound table above: 25, 26, 27, 28, 29, 30, 31, 32, 33, 35, 43, 44, 45, 46, 47, 49, 50, 51, 52, 53, and 54.

Example 5

Preparation of a compound (I) where $L_1$ is a group of formula (a) where $R^1$ is hydrogen, $R^2$ is methyl, G is —$NR^7$— where $R^7$ is pyridin-2-ylmethyl and $R^3$ and $R^4$ together with the carbon atom to which they are attached form —C=O and $L_2$ is a group of formula Ar—W— where Ar—W is 2-methylphenyl-NH—*C(O)CH—($CH_2CH_3$)— where *C=(RS) and further wherein both $L_1$ and $L_2$ are attached to the linker, X, via 1,4,10,13-tetraoxa-7,16-diazacyclooctadecane following FIG. 5

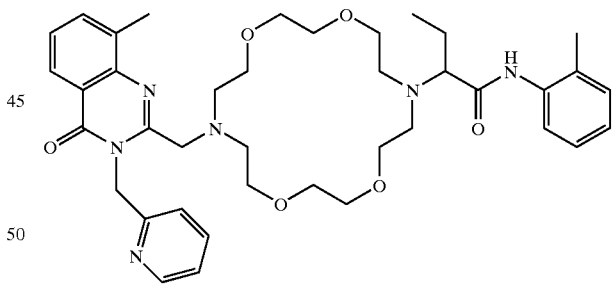

Step 1

A mixture of compound (I) prepared as described in Example 4 above, and 2-aminomethyl-pyridine (0.15 ml, 1.45 mmol) in dioxane (3 ml) was heated at 98 ° C. for 18 h. After 4 h precipitates formed. Acetic acid (3 ml) was added and the stirring was continued at 90 ° C. After 48 h, the reaction mixture was concentrated under reduced pressure and was poured into 1N NaOH solution, followed by extraction with dichlormethane (3×50ml). The organic phase was washed with brine to pH ~7, dried over $Na_2SO_4$, filtered and the filtrate was concentrated to dryness. The residue was purified by chromatography over silica-gel using a mixture of ethyl acetate and hexane, containing 1% triethylamine, as eluent. The collected fractions was concentrated to give the compound (I) as a yellow solid, which was converted to its dihydrochloride salt as described above. MS: 701 (M+H$^+$).

Example 6

Preparation of a compound (I) where $L_1$ is a group of formula (a) where $R^1$ is hydrogen, $R^2$ is methyl, G is —$NR^7$— where $R^7$ is —$CH_2CON(CH_3)_2$ and $R^3$ and $R^4$ together with the carbon atom to which they are attached form —C=O and $L_2$ is a Ar—W where Ar is a group of formula (d) where where $R^{10}$ is hydrogen, $R^{11}$ is methyl, W is —$NR^{16}$— where $R^{16}$ is —$CH_2CON(CH_3)_2$ and $R^{12}$ and $R^{13}$ together with the carbon atom to which they are attached form —C=O and W is —$CH_2$— and further wherein both $L_1$ and $L_2$ are attached to the linker, X, via 1,4,10,13-tetraoxa-7,16-diazacyclooctadecane following FIG. 6

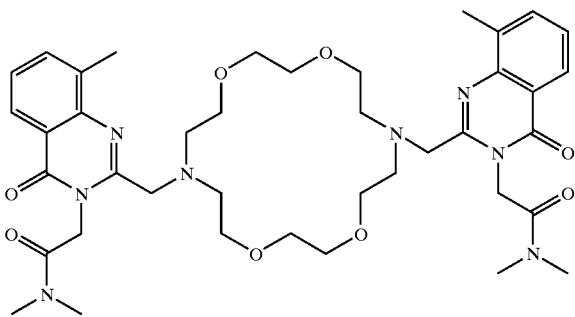

Step 1

2-Chloro-N,N-dimethylacetamide 64 (3.0 g, 25 mmol, 1 equiv.) was dissolved in EtOH (125 ml) and the reaction mixture was heated to 78 ° C. Sodium azide (1.6 g, 25 mmol, 1 equiv.) was added along with enough water to dissolve the azide (2 ml). After 4 h, the solution was filtered and the filtrate containing compound 65 was used in the next step without further purification.

Step 2

Compound 65 was hydrogenated overnight, in the presence of 10% palladium hydroxide on carbon (1.0 g) at 35 psi for 4 h. The reaction mixture was filtered through filter paper using a Buchner funnel and thoroughly rinsed with EtOH (50 ml). The filtrate was concentrated to dryness on a rotary evaporator to give compound 66 (1.97 g, 77%) as a yellow oil with >95% purity.

Step 3

3-Methyl-2-nitrobenzoic acid 67 (30.0 g, 166 mmol, 1.0 equiv.) was suspended in $CH_2Cl_2$ (150 ml) and the suspension was cooled to 0° C. using an ice bath. Oxalyl chloride (2.0 M in $CH_2Cl_2$, 166 ml, 332 mmol, 2.0 equiv.) was added to the stirred reaction mixture through a pressure equalizing dropping funnel over 30 min. DMF (10 drops) was added dropwise. The reaction mixture was allowed to warm up to room temperature. After 30 min., the reaction was concentrated to dryness on a rotary evaporator. The solid material was re-dissolved in $CH_2Cl_2$ (200 ml) and was concentrated to dryness on a rotary evaporator to give 3-methyl-2-nitrobenzoylchloride 68 (32.9 g, 99%) as an off white solid.

Step 4

N,N-Diisopropylethylamine (7.1 ml, 41 mmol, 1.5 equiv.) was added to a solution of compound 68 (6.0 g, 30 mmol, 1.1 equiv.) in $CH_2Cl_2$ (50 ml) at 0° C. A solution of compound 66 (2.79 g, 27 mmol, 1.0 equiv.), prepared in Step 2 above, in methylene chloride (50 ml) was added dropwise (50 ml) over 1 h using a pressure equalizing dropping funnel. The reaction mixture was warmed to room temperature and stirring continued for 0.5 h. The reaction mixture was poured into a separatory funnel and washed with saturated sodium bicarbonate ($NaHCO_3$) (150 ml). The organic layer was washed with saturated sodium chloride (NaCl) (100 ml), dried over anhydrous magnesium sulfate ($MgSO_4$) (20 g), and filtered. The filtrate was concentrated to dryness on a rotary evaporator. The crude product was purified using a silica gel plug to give compound 69 (2.5 g, 34.5%) as a white solid with >95% purity.

Step 5

A solution of compound 69 (2.5 g, 9.4 mmol, 1.0 equiv.) in tetrahydrofuran (THF) (150 ml) was hydrogenated in the presence of 10% palladium hydroxide on carbon (1.0 g) at 35 psi for 1 h. The reaction mixture was filtered through filter paper using a Buchner funnel and thoroughly rinsed with THF (100 ml). The filtrate was concentrated to dryness on a rotary evaporator to give compound 70 (2.2 g, 100%) as a yellow oil with >95% purity.

Step 6

A solution of compound 70 (2.2 g, 9.4 mmol, 1.0 equiv.), prepared as described in Step 5 above, in acetic acid (8.3 ml) was cooled to 10° C. using a cold water bath. Chloroacetyl chloride (0.82 ml, 10.3 mmol, 1.1 equiv.) was added, followed by the addition of a solution of sodium acetate (3.2 g) in water (16 ml). The reaction was allowed to warm to room temperature over 20 min. The reaction mixture was filtered through filter paper using a Buchner funnel and the solid was thoroughly rinsed with water (1 l). The solid was dried in vacuum to give compound 71 (2.6 g, 89.6%) as a white solid with 99% purity.

Step 7

Compound 71 (0.3 g, 0.96 mmol, 2.0 equiv.), prepared as described in Step 6 above, 1,4,10,13-tetraoxa-7,16-diazacyclooctadecane (0.13 g, 0.48 mmol, 1.0 equiv.), EtOH (0.5 ml), DMF (0.5 ml) and N,N-diisopropylethylamine (DIPEA) (0.18 ml, 1.0 mmol, 2.1 equiv.) were combined in a pressure tube, containing a magnetic stir bar. The tube was sealed and heated to 100° C. with stirring for 5 h. The contents of the tube were poured in a separatory funnel and partitioned between 1 N HCl (20 ml) and EtOAc (50 ml). The aqueous layer was washed with EtOAc (4×40 ml). The acidic layer was made basic (pH>10) with the addition of 3 N NaOH (30 ml) and extracted with EtOAc (1×100 ml). The EtOAc layer was washed with saturated sodium bicarbonate ($NaHCO_3$) (50 ml) and saturated sodium chloride (NaCl) (20 ml), and dried over anhydrous magnesium sulfate ($MgSO_4$) (10 g). The organics were filtered and the residue thoroughly rinsed with EtOAc (50 ml). The filtrate was concentrated to dryness on a rotary evaporator. Purification by column chromatography (elution gradient: 2:98 MeOH:$CH_2Cl_2$ (500 ml) and then 5:95 MeOH:$CH_2Cl_2$ (500 ml) gave the desired compound as an oil which was converted to the bis-hydrochloride salt as follows. 4.0 N HCl in dioxane (0.5 ml, 5.0 equiv.) was added to a solution of the free amine in MeOH (1 ml). The resulting solution was slowly dripped into ether (100 ml) with vigorous stirring. The product was filtered off, rinsed with ether (30 ml), dried under vacuum, and dissolved in 20:80 acetonitrile:water (50 ml). The solution was frozen using a dry ice-acetone bath, and lyophilized to yield the desired compound (I) dihydrochloride as a white powder.

Example 7

Figure 7:
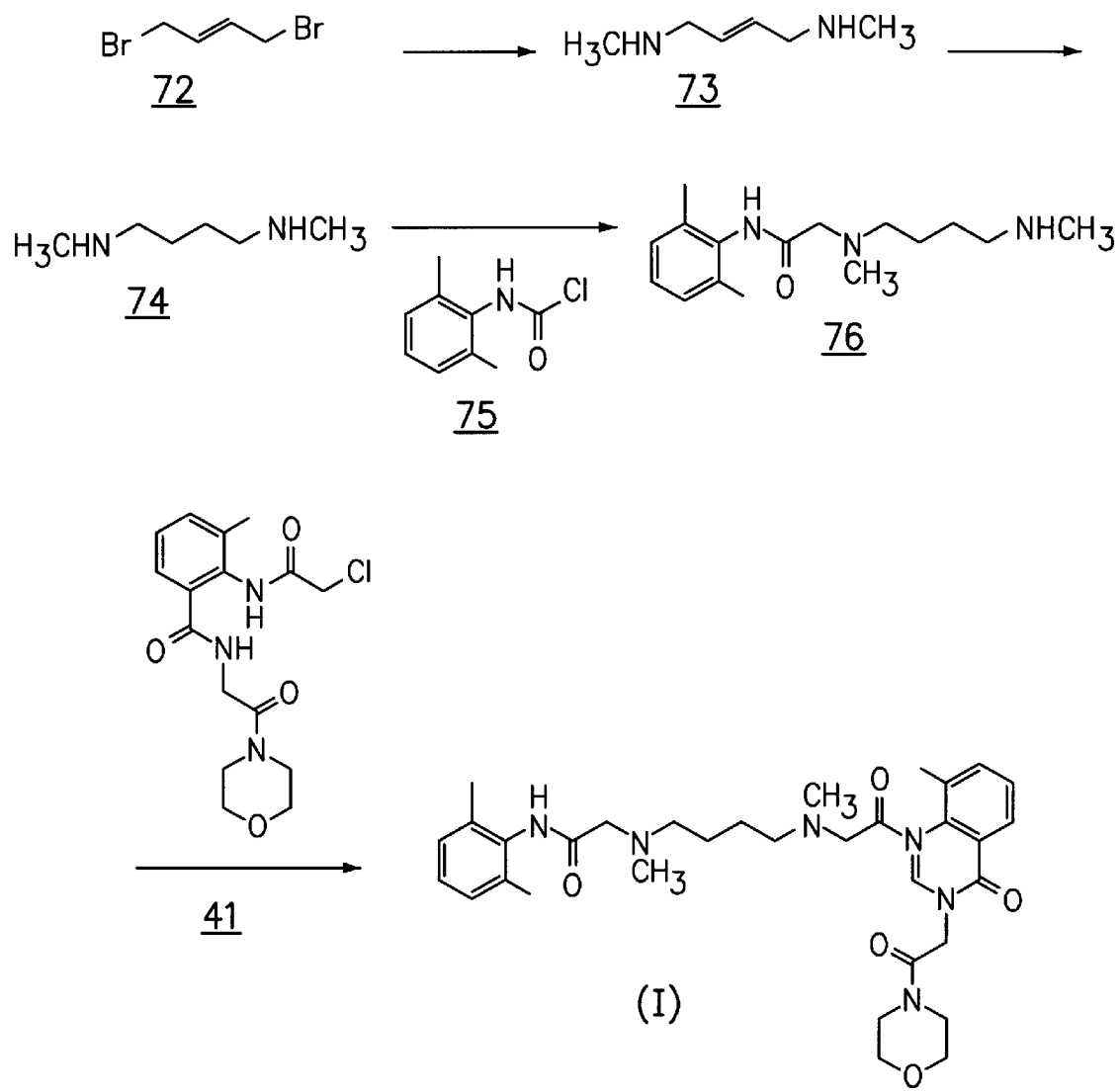

Preparation of a compound (I) where $L_1$ is a group of formula (a) where $R^1$ is hydrogen, $R^2$ is methyl, G is —$NR^7$— where $R^7$ is —$CH_2CO$morpholin-4-yl and $R_3$ and $R_4$ together with the carbon atom to which they are attached form —C=O and $L_2$ is a group of formula Ar—W— where Ar—W is 2-methylphenyl-NH—C(O)CH$_2$— and further wherein both $L_1$ and $L_2$ are attached to the linker, X, via 1,4-N,N'-dimethylaminobutane following FIG. 7

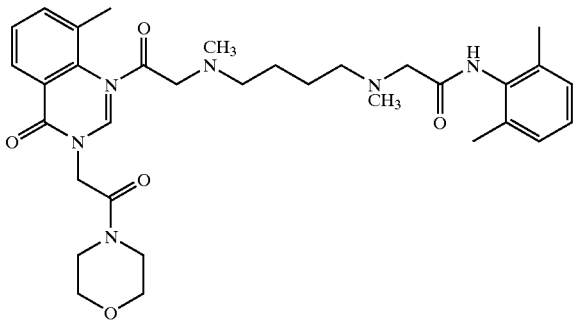

Step 1

A solution of 1,4-dibrombutene 72 (60 g, 0.28 mol) was added slowly to a mixture of 2 N methylamine solution in methanol (1 1) and 8N methylamine solution in ethanol (0.5 1) below 30 ° C. After addition, the reaction mixture was stirred at room temperature for 1 h and then heated at 40 ° C. overnight. The reaction mixture was concentrated and the obtained residue was dissolved in a mixture of isopropanol and ethanol. Acetonitrile was added to give N,N'-dimethyl-2-butene-1,4-diamine dihydrobromide 73 (35.5g, 45%) as white solid.

Step 2

N,N'-dimethyl-2-butene-1,4-diamine dihydrobromide 73 (35 g) dissolved in a mixture of MeOH (600 ml), i-PrOH (50 ml) and water (100 ml) was hydrogenated in the presence of 10% Pd/C (4 g) at 30 psi for 18 h. The reaction mixture was filtered and the filtrate was concentrated to give N,N'-dimethylputrescine dihydrobromide 74 (32 g) as a white solid.

Step 3

A mixture of N,N'-dimethylputrescine dihydrobromide 74 (38 g, 0.14 mol), N-chloroacetyl-2,6-dimethylaniline 75 (16 g, 0.08 mol) and diisopropylethyl-amine (32 ml, 0.18 mol) in ethanol (750 ml) was heated at 85° C. for 18 h. After cooling to room temperature, precipitation occurred and the mixture was filtered. The filtrate was concentrated to dryness. The residue was taken into a mixture of CHCl$_3$/i-PrOH (4/1, 800 ml), washed with a saturated solution of sodium bicarbonate (2×150 ml) and brine (1×150 ml), dried over Na$_2$SO4, filtered and concentrated. Purification by column chromatography using CH$_2$Cl$_2$/MeOH/25%NH$_4$OH (94.5/5/0.5–89/10/1) as eluent, gave compound 76 as a white solid (19.1 g, 86%).

Step 3

In a sealed tube, a mixture of compound 76 (277 mg, 1 mmol), compound 41 (355 mg, 1 mmol), prepared as described in Example 1 above, and diisopropylethylamine (0.2 ml, 1.1 mmol) in EtOH (4 ml ) and DMF (1 ml) was heated at 110° C. overnight. After concentrating under reduced pressure, the reaction mixture was taken into ethyl acetate and acidified with 0.25 N HCl to pH ~2. The aqueous phase was washed with ethyl acetate, basified with 25% NaOH solution, and then extracted with ethyl acetate. The organic phase was washed with brine, dried over Na$_2$SO$_4$, filtered and concentrated. The residue was purified by column chromatography using CH$_2$Cl$_2$/MeOH/25%NH$_4$OH (97/2.3/0.3–96/3.7/0.3) as eluent to give desired compound (I) as a colorless oil (223 mg, 39%), which was converted to its corresponding dihydrochloride salt. MS: 577 (M+H$^+$).

Example 8

Figure 8:
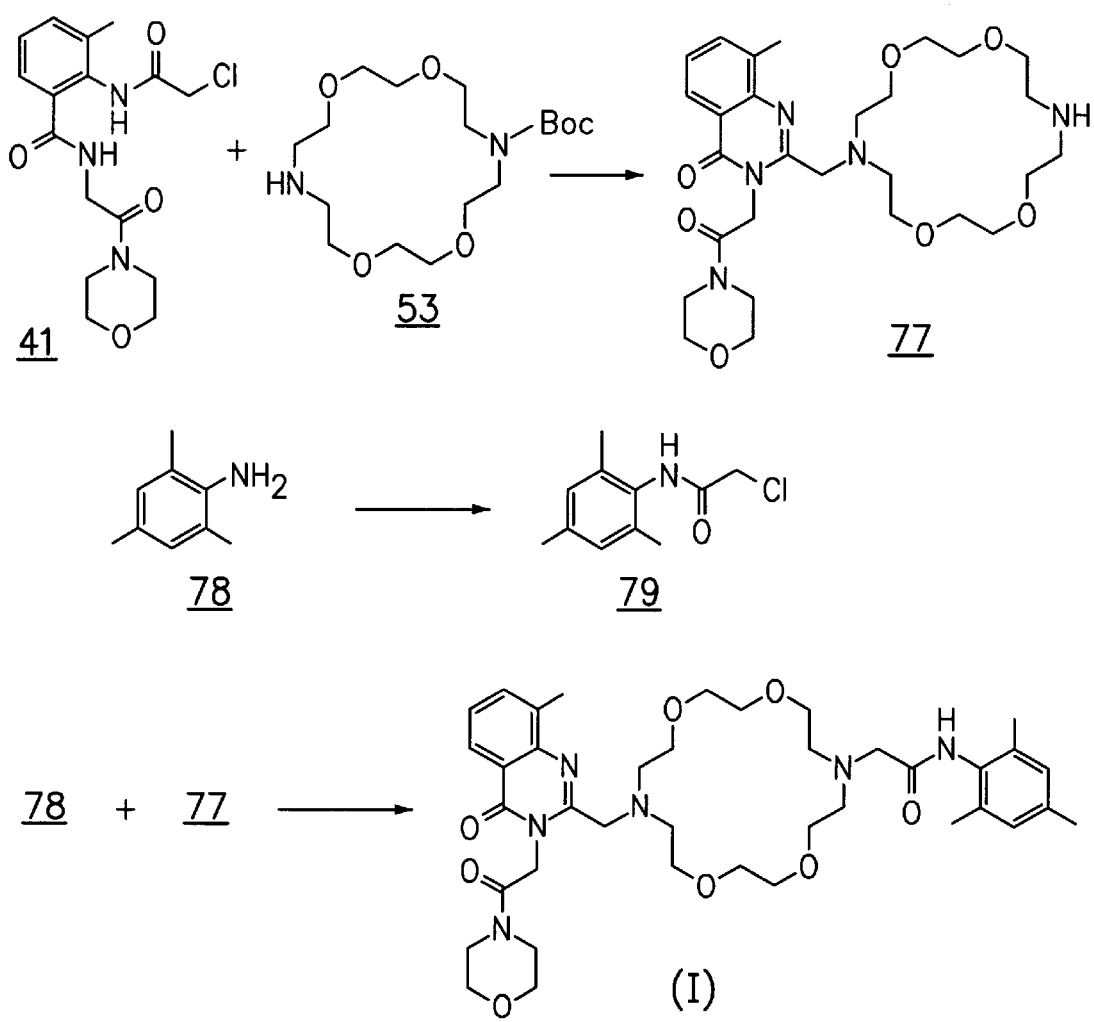

Preparation of a compound (I) where $L_1$ is a group of formula (a) where $R^1$ is hydrogen, $R^2$ is methyl, G is —NR$^7$— where R$^7$ is —CH$_2$COmorpholin-4-yl and $R^3$ and $R^4$ together with the carbon atom to which they are attached form —C=O and $L_2$ is a group of formula Ar—W— where Ar—W is 2,4,6-trimethylphenyl-NH—C(O)CH$_2$— and further wherein both $L_1$ and $L_2$ are attached to the linker, X, via 1,4,10,1 3-tetraoxa-7,16-diazacyclooctadecane following FIG. 8

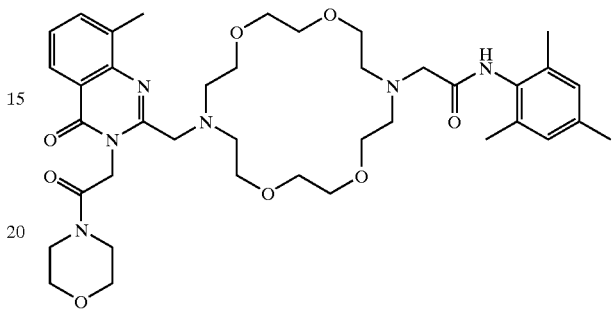

Step 1

A mixture of compound 41 (9.19 g, 26.0 mmol, 1.2 equiv.) and compound 53 (7.84 g, 21.7 mmol, 1.0 equiv.) in EtOH (20 ml), DMF (10 ml) and N,N-diisopropylethylamine (DIPEA) (3.77 ml, 21.7 mmol, 1.0 equiv.) was heated to 95° C. for 12 h. The solvent was removed under reduced pressure and the residue re-dissolved in ethyl acetate (200 ml). The ethyl acetate layer was washed with brine, dried over magnesium sulfate, and concentrated to give an oil. The oil was re-dissolved in methylene chloride (50 ml) and loaded onto a pad of silica gel. The product was eluted with a gradient of 0 to 5% methanol in methylene chloride. The solvents were removed to give an oil which was dissolved in methylene chloride (30 ml) and cooled to 0° C. Trifluoroacetic acid (30 ml) was added and the solution was stirred for 4 h. The reaction mixture was concentrated to an oil which was re-dissolved in 1.0 N HCl (100 ml). The aqueous solution was washed with ethyl acetate (2×100 mL) and then made alkaline by dropwise addition of 6N NaOH until the pH was 12. The aqueous solution was then extracted with three 100 mL portions of ethyl acetate. The ethyl acetate extracts were combined, dried over magnesium sulfate and concentrated to give compound 77 ( 9.36 g, 77%) as a pale brown oil with >90% purity.

Step 2

A solution of compound 78 (13.5 g, 100 mmol, 1.0 equiv.) in acetic acid (88 ml) was cooled to 10° C. using a cold water bath. Chloroacetyl chloride (10.7 ml, 120 mmol, 1.2 equiv.) was added all at once to the stirring reaction mixture. This was immediately followed by the addition of a solution of sodium acetate (34 g) in water (175 ml). The reaction mixture was warmed to room temperature while stirring for 20 min. Manual shaking was applied periodically to break up thick clumps of precipitate. The reaction mixture was filtered and the solid thoroughly rinsed with water (2 1). The solid was dried in to give compound 79 (16.9 g, 79.7%) as a white solid Step 3

A mixture of compound 77 (0.34 g, 1.6 mmol, 1.8 equiv.), compound 79 (0.5 g, 0.89 mmol, 1.0 equiv.), EtOH (1.5 ml), and N,N-diisopropylethylamine (DIPEA) (0.23 ml, 1.3 mmol, 1.5 equiv.) was taken in a pressure tube, containing a magnetic stir bar. The tube was sealed and heated to 100°

C. with stirring for 5 h. The contents of the tube were placed in a separators funnel and partitioned between 1 N HCl (20 ml) and EtOAc (50 ml). The aqueous layer was washed with EtOAc (4×40 ml). The acidic layer was made basic (pH>10) with the addition of 3 N NaOH (30 ml) and extracted with EtOAc (1×100 ml). The EtOAc layer was washed with saturated sodium bicarbonate (NaHCO$_3$) (50 ml) and saturated sodium chloride (NaCl) (20 ml). The solution was dried over anhydrous magnesium sulfate (MgSO$_4$) (10 g), filtered, and the residue was thoroughly rinsed with EtOAc (50 ml). The filtrate was concentrated to dryness and the crude product was purified using a silica gel column using 2:98 MeOH:CH$_2$Cl$_2$ (500 ml) and then eluted with 5:95 MeOH:CH$_2$Cl$_2$ (500 ml) as the eluent. The purified fractions were combined and concentrated to dryness to the free amine as an oil. The bis-hydrochloride salt was prepared by dissolving the oil in MeOH (1 ml) and adding 4.0 N HCl in dioxane (1. 1 ml, 5.0 equiv.) and stirring for 5 min. This solution was dripped into ether (100 ml) with vigorous stirring in order to precipitate the product. The product was filtered, thoroughly rinsed with ether (30 ml), dried under vacuum, and dissolved in 20:80 acetonitrile:water (50 ml). The solution was frozen using a dry ice-acetone bath, and lyophilized to yield the desired compound (I) as a white powder.

Example 9

Figure 9:
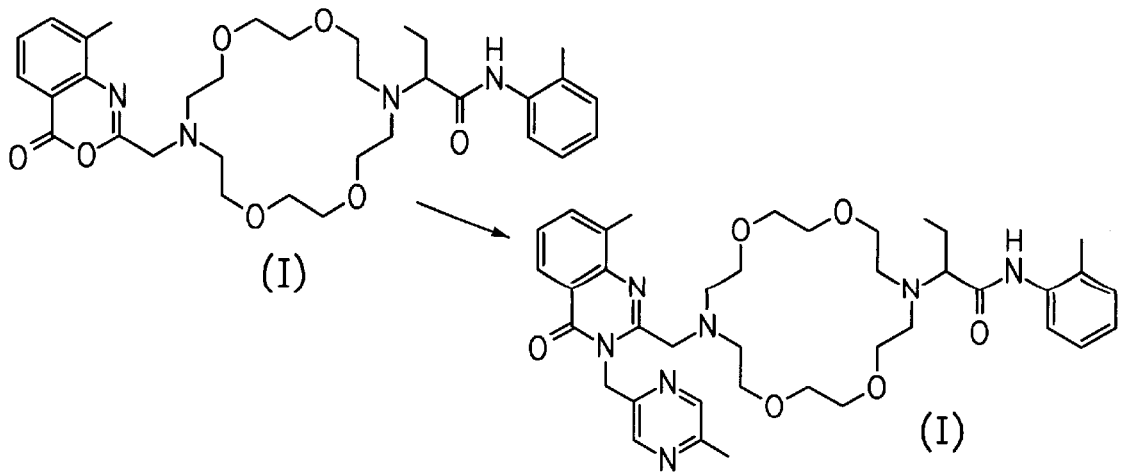
Figure 11:
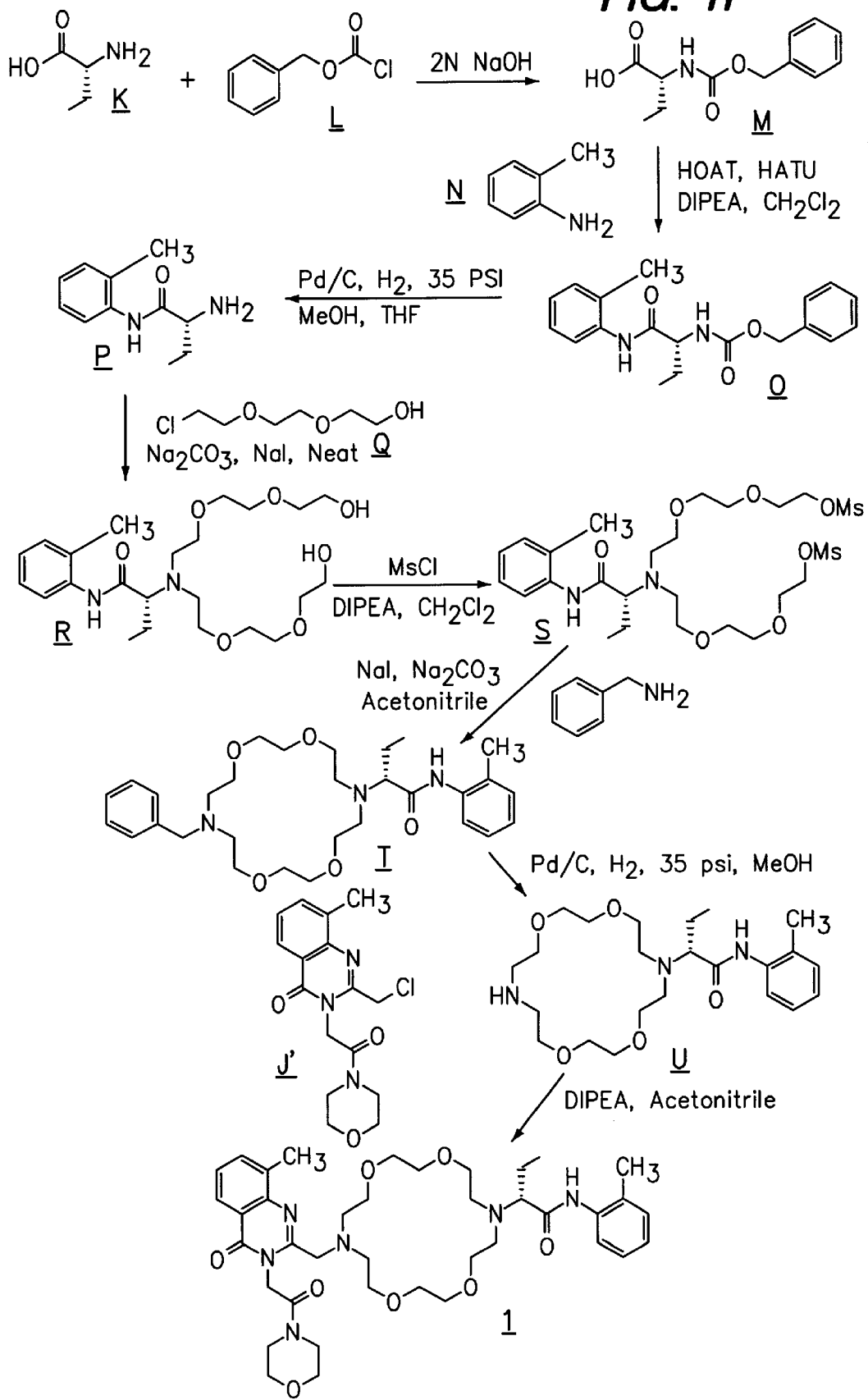

Preparation of a compound (I) where L$_1$ is a group of formula (a) where R$^1$ is hydrogen, R$^2$ is methyl, G is —NR$^7$— where R$^7$ is 5-methylpyrazin-2-ylmethyl and R$^3$ and R$^4$ together with the carbon atom to which they are attached form —C=O and L$_2$ is a group of formula Ar—W— where Ar—W is 2-methylphenyl-NH—C(O)*CH (CH$_2$CH$_3$)— where *C=(RS) and further wherein both L$_1$ and L$_2$ are attached to the linker, X, via 1,4,10,13-tetraoxa-7,16-diazacyclooctadecane following FIG. 9

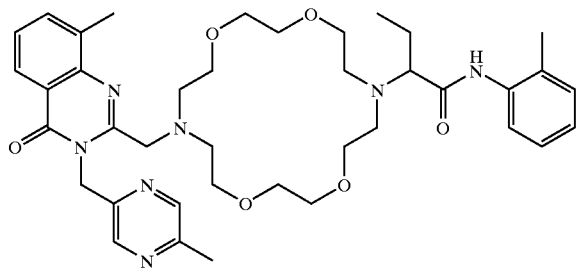

Step 1

A mixture of compound (I) where L$_1$ is a compound of formula (a) where G is oxygen (500 mg, 0.82 mmol), 2-(aminomethyl)-5-methylpyrazine (210 mg, 1.7 mmol) in dioxane (2 ml) was stirred at 100° C. in a sealed tube overnight. Glacial acetic acid (2 ml) was added, and stirring was continured at 100° C. overnight. The reaction mixture was partitioned between dichloromethane and 20% sodium hydroxide. The organic phase was washed with brine, dried, filtered, and concentrated. The crude was purified by preparative HPLC, pure fractions were pooled, solvents were evaporated, saturated sodium bicarbonate was added, extracted with dichloromethane. The organic phase was dried, filtered, concentrated, and further converted to its dihydrochloride salt (300 mg, 46%) by treating with 4N HCl solution in dioxane.

Example 10

Preparation of a compound (I) where L$_1$ is a group of formula (a) where R$^1$ is hydrogen, R$^2$ is methyl, G is —NR$^7$— where R$^7$ is —CH$_2$COmorpholin-4-yl and R$^3$ and R$^4$ together with the carbon atom to which they are attached form —C=O and L$_2$ is a group of formula Ar—W— where Ar—W is 2-methylphenyl-NH—C(O)*CH(CH$_2$CH$_3$)— where *C=(R) and further wherein both L$_1$ and L$_2$ are attached to the linker, X, via 1,4,10,1 3-tetraoxa-7,16-diazacyclooctadecane following FIG. 10

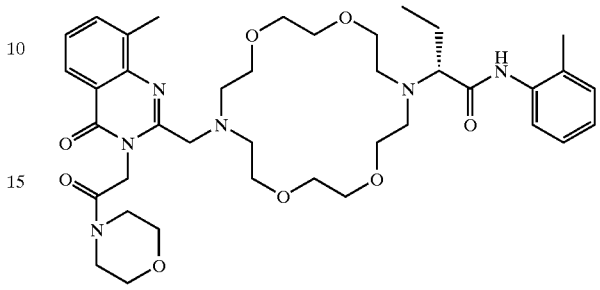

Step 1

Under N$_2$ in a 1-liter 2-necked round bottom flask equipped with a magnetic stir bar, carbobenzyloxyglicine A (25.8 g, 123 mmoles, 1.0 equiv.), 1-hydroxy-7-azabenzotriazole (HOAT) (3.36 g, 24.7 mmoles, 0.2 equiv.) and N-[(dimethylamino)-1H-1,2,3,-triazolo[4,5-b]pyridin-1-ylmethylene]-N-methylmethanaminium hexafluorophosphate N-oxide (HATU) (46.9 g, 123 mmoles, 1.0 equiv.) were dissolved in N,N-dimethylformamide (DMF) (500 mL). The solution was cooled to 0° C. using an ice bath. N,N-Diisopropylethylamine (DIPEA) (32.2 mL, 185 mmoles, 1.5 equiv.) was added all at once to the stirred reaction mixture. This was followed by the addition of morpholine B (10.8 mL, 123 mmoles, 1.0 equiv.). The reaction was warmed to room temperature and stirring continued for 8 hours. The reaction mixture was poured into a stirred solution of sodium chloride (100 g) in water (3 L) and ice (1.5 L), resulting in precipitation of the product. The suspension was stirred for 1 h after which time the precipitate was isolated by filtration using a Buchner funnel and thoroughly rinsed with water (2 L). The solid was dried in vacuum to provide 31.4 g (91.6%) of compound C as a white solid with >95% purity ($^1$H NMR in DMSO).

On small scale it is advantageous to dry the product quickly using the following method. The solid is dissolved in CH$_2$Cl$_2$ (1 L) and partitioned with water (100 mL), the layers separated, and the organic layer washed with saturated aqueous NaCl (300 mL) and dried with MgSO$_4$ (50 g), filtered through filter paper, rinsing with CH$_2$Cl$_2$ (100 mL), concentrated under reduced pressure and place on vacuum line to dry (15 minutes).

Step 2

Under N$_2$, to a 1-liter Parr bottle was added 10% palladium on carbon (4.0 g) and tetrahydrofuran (THF) (100 mL). Compound C (31.4 g, 113 mmoles, 1.0 equiv.) was dissolved in methanol (MeOH) (100 mL) and THF (300 mL) and added to the Parr bottle. The Parr bottle was degassed under vacuum and filled to 35 psi with hydrogen gas. The shaker was turned on and the reaction allowed to shake for 1 minute, at which time the Parr bottle was degassed under vacuum and filled to 35 psi with hydrogen gas. This was repeated two more times. The reaction was kept under a constant pressure of hydrogen gas (between 25 and 35 psi) for the duration of the reaction time (1 hour). The reaction was monitored by TLC using 90:10 CH$_2$Cl$_2$:MeOH (starting material R$_f$=0.8 using UV and ninhydrin staining; product R$_f$=0.0 using ninhydrin staining). The reaction mixture was filtered through filter paper using a Buchner funnel and thoroughly rinsed with THF:MeOH (1:1) (300 mL). The filtrate was concentrated to dryness on a rotary evaporator to afford 16.2 g (99.6%) of compound D as a white solid with >95% purity ($^1$H NMR in DMSO).

Step 3

Under $N_2$ in a 1-liter round bottom flask equipped with a magnetic stir bar, 3-methyl-2-nitrobenzoic acid E (30.0 g, 166 mmoles, 1.0 equiv.) was suspended in $CH_2Cl_2$ (150 mL). The suspension was cooled to 0°0 C. using an ice bath. Oxalyl chloride (2.0 M in $CH_2Cl_2$, 166 mL, 332 mmoles, 2.0 equiv.) was added to the stirred reaction mixture through a pressure equalizing dropping funnel over 30 minutes. DMF (10 drops) was added dropwise. The reaction mixture was allowed to warm up to room temperature. After 30 minutes the suspended material dissolves and effervescence stops. The reaction was concentrated to dryness on a rotary evaporator. The solid material was redissolved in $CH_2Cl_2$ (200 mL) and was concentrated to dryness on a rotary evaporator to afford 32.9 g (99%) of compound F as an off white solid.

Step 4

Under $N_2$, in a 1-liter round bottom flask equipped with a magnetic stir bar, compound F (26.9 g, 135 mmoles, 1.2 equiv.) was dissolved in $CH_2Cl_2$ (200 mL). The solution was cooled to 0° C. using an ice bath. DIPEA (29.4 mL, 169 mmoles, 1.5 equiv.) was added all at once to the stirring reaction mixture. This was followed by the dropwise addition of the compound D (16.2 g, 113 mmoles, 1.0 equiv.) dissolved in $CH_2Cl_2$ (200 mL) over one hour using a pressure equalizing dropping funnel. The reaction was warmed to room temperature and stirring continued for 0.5 hour. The reaction mixture was poured into a separatory funnel and washed with saturated sodium bicarbonate ($NaHCO_3$) (250 mL). Washing with $NaHCO_3$ was repeated three times. The organic layer was washed once with saturated sodium chloride (NaCl) (200 mL), dried over anhydrous magnesium sulfate ($MgSO_4$) (20 g), filtered through filter paper using a Buchner funnel and the residue thoroughly rinsed with $CH_2Cl_2$ (200 mL). The filtrate was concentrated to dryness on a rotary evaporator. The product was purified using a silica gel plug. A Buchner funnel was filled with a slurry of silica gel in 98:2 $CH_2Cl_2$:MeOH (200 mL) and a solution of impure product in 98:2 $CH_2Cl_2$:MeOH (10 mL) was loaded onto the plug and a vacuum was applied to draw the solution into the silica gel plug. The plug was eluted with 98:2 $CH_2Cl_2$:MeOH (500 mL) using vacuum to pull solvent through the plug until all of the product had eluted. The pure fractions were combined and concentrated to dryness on a rotary evaporator to afford 32.8 g (95.0%) of compound G as a white solid with >95% purity ($^1$H NMR in DMSO). During the above procedure, the product was monitored by TLC using 90:10 $CH_2Cl_2$:MeOH (starting material as carboxylic acid $R_f$=0.25 using UV; product $R_f$=0.6 using UV and ninhydrin staining).

Step 5

Under $N_2$, to a 1-liter Parr bottle was added 10% palladium on activated carbon (4.5 g) and tetrahydrofuran (THF) (100 mL). Compound G (35.5 g, 116 mmoles, 1.0 equiv.) was dissolved in THF (300 mL) (starting material will precipitate out of THF if any MeOH is added) and added to the Parr bottle. The Parr bottle was degassed under vacuum and filled to 35 psi with hydrogen gas. The shaker was turned on and the reaction allowed to shake for 1 minute, at which time the Parr bottle was degassed under vacuum and filled to 35 psi with hydrogen gas. This was repeated two more times. The reaction was kept under a constant pressure of hydrogen gas (between 25 and 35 psi) for the duration of the reaction time (2 hours). The reaction was monitored by TLC using 90:10 $CH_2Cl_2$:MeOH (starting material $R_f$=0.6 using UV and ninhydrin staining; product $R_f$=0.55 using UV and ninhydrin staining). The reaction mixture was filtered through filter paper using a Buchner funnel and the residue thoroughly rinsed with THF (300 mL). The filtrate was concentrated to dryness on a rotary evaporator to afford 31.83 g (99.1 %) of compound H as a white solid with >95% purity ($^1$H NMR in DMSO).

Step 6

Under $N_2$ in a 1-liter 3-necked round bottom flask equipped with a magnetic stir bar, compound H (20.0 g, 72.2 mmoles, 1.0 equiv.) was dissolved in acetic acid (64.0 mL). The round bottom was cooled to 10° C. using a cold water bath (cooling is desirable to control reaction exothermicity, but it is necessary to avoid freezing the acetic acid solution). Chloroacetyl chloride I (6.33 mL, 79.4 mmoles, 1.1 equiv.) was added all at once to the stirring reaction mixture. This was immediately followed by the addition of a solution of sodium acetate (24.8 g) in water (126 mL) (the product precipitates out at this point as a white solid). The reaction was warmed to room temperature while stirring for 20 minutes. Manual shaking was applied periodically to break up thick clumps of precipitate. The mixture was filtered through filter paper using a Buchner funnel and the solid thoroughly rinsed with water (3 L). The solid was dried in vacuum to afford 20.12 g (78.8%) of compound J as a white solid with 99% purity ($^1$H NMR in DMSO).

On small scale it is advantageous to dry the product quickly using the following method. The solid is suspended in diethyl ether and stirred vigorously to dissolve residual water and acetic acid. If an aqueous layer forms, it is removed by decanting. The solid is isolated by filtration. The ether wash may be repeated once or twice more if necessary.

Step 7

A suspension of compound J (30.0 g, 84.9 mmol) in acetic acid (80 mL) and EtOH (80 mL) was heated at 85° C. After a few minutes heating, a homogeneous solution was obtained and the stirring was continued at 85° C. for 12 h. Upon cooling to room temperature, the product crystallized. The solid was filtered and washed with EtOH. The filtrate was concentrated and a second crop of crystals was obtained by recrystalization from ethanol. The solid was filtered and washed with EtOH. The filtrate was concentrated and a third crop of crystals was obtained by recrystallization from ethanol. The three crops of crystals (crop 1=17.8 g, crop 2=3.6 g, crop 3=1.3 g) were determined to be pure by HPLC analysis and combined to give compound as a white crystalline solid (22.7 g, 80%). During the above procedure, the reaction was monitored by TLC using 70:30 ethyl acetate:hexanes with detection by UV absorbance (product $R_f$=0.38). The reaction can also be monitored by HPLC and product purity was determined by HPLC using a Zorbax Bonus RP (5 $\mu$m) column (2.1 mm×50 mm) with a gradient of 10 to 70% acetonitrile/0.2% TFA in water/0.2% TFA over 5.0 min with a flow rate of 0.5 mL/min and detection by U/V absorbency at 214 nm. Under these conditions, the product elutes at 3.4 min and the starting material elutes at 2.1 min.

Step 8

Under $N_2$ in a 2-liter 3-necked round bottom flask equipped with a magnetic stir bar, (R)-(+)-2-aminobutyric acid K (100 g, 970 mmoles, 1.0 equiv.) was dissolved in 2 N sodium hydroxide (NaOH) (500.0 mL). The solution was cooled to 0° C. using an ice bath. Benzyl chloroformate L (166.0 mL, 1160 mmoles, 1.2 equiv.) and 2 N NaOH (800 mL) were added alternately in small portions (approximately ten portions each). The reaction mixture should remain alkaline: if necessary more 2 N NaOH is added. The temperature of the reaction mixture is kept between 5 and 10° C. by the rate of addition of the reactants. Addition over approximately 1.5 hours allows the temperature to remain in this range. The ice bath was then replaced by a 20° C. water bath, and vigorous stirring was continued for an additional hour. The alkaline solution was extracted three times with ether (500 mL each); the ether extracts were discarded. The alkaline layer was made acidic by the addition of 3 N hydrochloric acid (HCl) (400 mL) and extracted three times with ether (500 mL each). The combined ether layers were washed once with saturated sodium chloride (NaCl) (400 mL), dried over anhydrous magnesium sulfate ($MgSO_4$) (80 g), filtered through filter paper using a Buchner funnel and the residue thoroughly rinsed with ether (500 mL). The filtrate was concentrated to dryness on a rotary evaporator to afford 228 g (99%) of compound M as a white solid with >95% purity ($^1$H NMR in DMSO).

Step 9

Under $N_2$ in a 1-liter 2-necked round bottom flask equipped with a magnetic stir bar, carbobenzyloxy-(R)-2-aminobutyric acid M (40.0 g, 169 mmoles, 1.0 equiv.), 1-hydroxy-7-azabenzotriazole (HOAT) (4.59 g, 33.8 mmoles, 0.2 equiv.) and N-[(dimethylamino)-1H-1,2,3,-triazolo[4,5-b]pyridin-1-ylmethylene]-N-methylmethanaminium hexafluorophosphate N-oxide (HATU) (64.2 g, 169 mmoles, 1.0 equiv.) were dissolved in N,N-dimethylformamide (DMF) (350 mL). The solution was cooled to 0° C. using an ice bath. N,N-diisopropylethylamine (DIPEA) (44.1 mL, 253 mmoles, 1.5 equiv.) was added all at once to the stirred reaction mixture. This was followed by the addition of o-toluidine N (18.0 mL, 169 mmoles, 1.0 equiv.). The reaction was warmed to room temperature and stirring continued for 8 hours. The reaction mixture was poured into a stirred solution of sodium chloride (500 g) in water (3 L) and ice (1.5 L), causing the product to precipitate. The precipitate isolated by filtration using a Buchner funnel and thoroughly rinsed with water (2 L). The solid was dried in vacuum to afford 51.2 g (93%) of compound O as a white solid with >95% purity ($^1$H NMR in DMSO).

On small scale it is advantageous to dry the product quickly using the following method. The solid is dissolved in $CH_2Cl_2$ (1-liter) and washed with water (100 mL) followed by saturated NaCl (300 mL), the $CH_2Cl_2$ layer is dried with $MgSO_4$ (50 g), filtered through filter paper, the residue rinsed with $CH_2Cl_2$ (100 mL), concentrated under reduced pressure and placed on vacuum line to dry (15 minutes).

Step 10

Under $N_2$, to a 1-liter Parr bottle was added 10% palladium on activated carbon (5.8 g) and tetrahydrofuran (THF) (100 mL). Compound O (55.0 g, 162 mmoles, 1.0 equiv.) was dissolved in MeOH (250 mL) and THF (200 mL) and added to the Parr bottle. The Parr bottle was degassed under vacuum and filled to 35 psi with hydrogen gas. The shaker was turned on and the reaction allowed to shake for 1 minute, at which time the Parr bottle was degassed under vacuum and filled to 35 psi with hydrogen gas. This was repeated two more times. The reaction was kept under a constant pressure of hydrogen gas (between 25 and 35 psi) for the duration of the reaction time (1 hour). The reaction was monitored by TLC using 50:50 ethyl acetate:hexanes (starting material $R_f$=0.8 using UV and ninhydrin staining; product $R_f$=0.0 using UV and ninhydrin staining). The reaction mixture was filtered through filter paper using a Buchner funnel and thoroughly rinsed with 50% THF, 50% MeOH (300 mL). The filtrate was concentrated to dryness on a rotary evaporator to afford 32.6 g (98%) of compound P as a white solid with >95% purity ($^1$H NMR in DMSO).

In the above procedure, the starting material O can be dissolved by heating in THF/MeOH at the concentrations described and will remain in solution for some time, however it does begin to crystallize over time. Therefore, it may be advantageous to carry out this reaction at slightly elevated temperature or to use a solvent mixture in which the starting material is more soluble.

Step 11

In a 3-neck 1000 mL flask equipped with a mechanical stirrer, amine P (113 g, 587 mmol), 2-[2-(chloroethoxy)ethoxy]ethanol O (188 mL, 218 g, 1290 mmol, 2.2 equiv.), sodium iodide (88.0 g, 587 mmol, 1.0 eq), and sodium carbonate (218 g, 2050 mmol, 3.5 equiv.) were combined and heated to 120° C. Evolution of gas was observed during heating and a red color developed. After 8 h, the reaction was cooled to room temperature and transferred to a separatory funnel. The mixture was dissolved by shaking with a mixture of 1.5 L ethyl acetate and 1.5 L water. The layers were separated and the ethyl acetate was washed with 1000 mL water. The aqueous layers were combined and extracted with 500 mL ethyl acetate. The ethyl acetate layers were combined and washed with saturated aqueous sodium bicarbonate (1 L) and then extracted with two 700 mL portions of 1 N HCl. The aqueous acid layers were combined and washed two times with 1000 mL portions of ethyl acetate. The aqueous acid was then made basic by dropwise addition of 3.0 N NaOH until the pH reached 8.0. The resulting cloudy suspension was then extracted with 1000 mL ethyl acetate. The pH of the aqueous layer was adjusted up to 9.0 and extracted twice with 1000 mL portions of ethyl acetate. These ethyl acetate layers (extracts of basic aqueous solution) were combined and dried over anhydrous magnesium sulfate ($MgSO_4$) (50 g), filtered through filter paper using a Buchner funnel and the residue thoroughly rinsed with ethyl acetate (600 mL). The filtrate was concentrated on a rotary evaporator to give a 229 g (86%) of diol R as a pale yellow oil with >85% purity (HPLC, 214 nm, NMR). During this procedure, the reaction was monitored by TLC using 90:10 $CH_2Cl_2$:MeOH with detection by UV absorbance (product $R_f$=0.58). The reaction can also be monitored and product purity can be assessed by HPLC using a Zorbax Bonus RP (5 µm) column (2.1 mm×50 mm) with a gradient of 10 to 70% acetonitrile/0.2% TFA in water/0.2% TFA over 5.0 min with a flow rate of 0.5 mL/min and detection by UV absorbency at 214 nm. Under these conditions the product elutes at 1.8 min.

Step 12

Under $N_2$, in a 5000-mL three-neck flask equipped with a magnetic stir bar, diol R (229 g, 502 mmoles, 1.0 equiv.) was dissolved in $CH_2Cl_2$ (3000 mL). The solution was cooled to −10° C. using an ice/isopropanol bath. DIPEA (210 mL, 1200 mmoles, 2.4 equiv.) was added all at once to the stirring reaction mixture. This was followed by the dropwise addition of methanesulfonyl chloride (81 mL, 1040 mmoles, 2.07 equiv.). Upon completion of addition, TLC indicated that the reaction was complete. Saturated aqueous sodium bicarbonate (1000 mL) was added to the cold reaction mixture with vigorous stirring, and the mixture was transferred to a separatory funnel. The layers were separated and the methylene chloride layer was extracted with a second portion (500 mL) of saturated aqueous sodium bicarbonate. The aqueous layers were combined and extracted once with $CH_2Cl_2$ (600 mL). The organic layers were combined, washed with saturated aqueous sodium chloride (500 mL), dried over anhydrous magnesium sulfate (MgSO$_4$) (50 g), filtered through filter paper using a Buchner funnel and the residue thoroughly rinsed with CH$_2$Cl$_2$ (100 mL). The filtrate was concentrated to dryness on a rotary evaporator to yield a brown oil. This oil was purified in six batches of approximately 50 g each by filtering through plugs of silica as follows. A Buchner funnel was filled with a slurry of silica gel in CH$_2$Cl$_2$ (450 mL). A solution of impure product in CH$_2$Cl$_2$ (60 mL) was loaded onto the plug and a vacuum was applied to draw the solution into the silica gel plug. The plug was washed with CH$_2$Cl$_2$ (400 mL) and eluted with 99:1 CH$_2$Cl$_2$:MeOH (600 mL) using vacuum to pull solvent through the plug until all of the product had eluted. The pure fractions were combined and concentrated to dryness on a rotary evaporator. This process was repeated once to afford the product in 96% purity. The pure fractions from all silica plugs were combined and concentrated to afford 234 g (76%) of compound S as a yellow oil with >97% purity (HPLC, 214 nm, NMR CDCl$_3$. During this procedure, the reaction was monitored by TLC using 90:10 CH$_2$Cl$_2$:MeOH with detection by UV absorbance (starting material R$_f$=0.58; product R$_f$=0.74). The reaction can also be monitored and the purity of the product determined by HPLC using a Zorbax Bonus RP (5 μm) column (2.1 mm×50 mm) with a gradient of 10 to 70% acetonitrile/0.2% TFA in water/0.2% TFA over 5.0 min with a flow rate of 0.5 mL/min and detection by UV absorbency at 214 nm. Under these conditions, the starting material elutes at 1.8 min, and the product elutes at 2.8 min.

Step 13

Divided equally between two 5000-mL 3-neck round bottom flasks equipped with mechanical stirrers, thermometers and reflux condensers, dimesylate S (234 g, 381 mmol, 1.15 equiv.) and benzylamine (36.2 mL, 35.5 g, 331 mmol, 1.0 equiv) were dissolved in acetonitrile (6000 mL). Sodium iodide (109 g, 723 mmol, 2.2 equiv) and sodium carbonate (158 g, 1490 mmol, 4.5 equiv) were added (half of each to each of the two flasks) and the suspensions were heated between 60 and 70° C. for 40 h. The suspensions were combined and filtered through filter paper using a Buchner funnel and the residue thoroughly rinsed with acetonitrile (800 mL). The filtrate was concentrated in vacuo to a thick yellow oil and redissolved in ethyl acetate (1000 mL). The suspension was washed with two 1 L portions of saturated sodium bicarbonate followed by 250 mL of saturated aqueous sodium chloride. The ethyl acetate layer was then shaken with 500 mL of 0.2 N HCl. The pH was gradually lowered by portionwise addition of 1.0 N HCl followed by shaking until the aqueous layer had a pH of 4. The layers were separated. The ethyl acetate layer was extracted with a second portion of 0.2 N HCl (500 mL), again adding portions of 1.0 N HCl and shaking until the pH reached 3. This process was repeated a third time, bringing the final aqueous extract to a pH of 1. HPLC confirmed that no product remained in the ethyl acetate layer and this layer was discarded. The aqueous acid layers were combined and a milky precipitate formed. The pH of the combined aqueous layers was reduced to 3 by dropwise addition of concentrated HCl at which point a clear solution was obtained. Activated carbon (50 g decolorizing carbon, Aldrich # 16155-1) was added and stirred for 10 min. Activated carbon was removed by filtration through a buchner funnel (although it would have been preferable to have continued the charcoal treatment in aqueous acid at this point, the product was extracted into the organic in order to avoid leaving the product exposed to aqueous acid overnight due to concerns about racemization at low pH). The aqueous acid was made basic by dropwise addition of 6.0 N NaOH until the pH reached 6.0. The resulting cloudy suspension was then extracted with 300 mL ethyl acetate. The pH of the aqueous layer was adjusted up to 8.0 and extracted with 600 mL ethyl acetate. These ethyl acetate layers (extracts of basic aqueous solution) were combined and concentrated to give 155 g of crude product. Purity was 74% by HPLC. The crude product was dissolved in the minimal amount of 1 N HCl (approximately 1 L). Upon complete dissolution of product, the pH reached 3. To this solution was added 236 g of decolorizing carbon in three batches followed by 30 g of DARCO G60. The activated carbon was removed by filtration using a Buchner funnel and the residue throroughly washed with 0.1 N HCl (300 mL). To the filtrate was added 130 g DARCO G60. After 10 min, the DARCO was removed by filtration using a Buchner funnel and the residue thoroughly washed with 0.1 N HCl (300 mL). The filtrate was then made basic by dropwise addition of 6.0 N NaOH until the pH reached 7.0. The resulting cloudy suspension was then extracted with 500 mL ethyl acetate. The pH of the aqueous layer was adjusted back up to 7.0 and extracted with 500 mL ethyl acetate. These ethyl acetate layers (extracts of neutral aqueous solution) showed high purity by HPLC and were combined, washed with 400 mL saturated aqueous sodium bicarbonate, and dried over anhydrous magnesium sulfate (MgSO$_4$) (25 g), filtered through filter paper using a Buchner funnel and the residue thoroughly rinsed with ethyl acetate (200 mL). The filtrate was concentrated on a rotary evaporator to give a 62 g (35%) of compound T as a colorless oil, 96% pure by HPLC. During the above procedure, the reaction was monitored by TLC using 90:10 CH$_2$Cl$_2$:MeOH with detection by UV absorbance (product R$_f$=0.48). The reaction can also be monitored and the purity of the product determined by HPLC using a Zorbax Bonus RP (5 pm) column (2.1 mm ×50 mm) with a gradient of 10 to 70% acetonitrile/0.2% TFA in water/0.2% TFA over 5.0 min with a flow rate of 0.5 mL/min and detection by UV absorbency at 214 nm. Under these conditions, starting material elutes at 2.8 min, but is rapidly converted to a diilodide which elutes at 3.8 min; and product elutes at 2.1 min.

Step 14

Under N$_2$, to a 1000-mL Parr bottle was added 10% palladium on activated carbon (6.2 g) and methanol (MeOH) (75 mL). Compound T (62.4 g, 118 mmoles) was dissolved in MeOH (75 mL) and added to the Parr bottle. The Parr bottle was degassed under vacuum and filled to 40 psi with hydrogen gas. The shaker was turned on and the reaction allowed to shake for 1 minute, at which time the Parr bottle was degassed under vacuum and filled to 40 psi with hydrogen gas. This was repeated two more times. The reaction was kept under a constant pressure of hydrogen gas (between 35 and 40 psi) for the duration of the reaction time (4 hours). The reaction mixture was filtered through filter paper using a Buchner funnel and thoroughly rinsed with MeOH (100 mL). The filtrate was concentrated to dryness on a rotary evaporator to afford 54.5 g (>98%) of compound U as a colorless oil with >95% purity (HPLC). During this procedure, the reaction was monitored by TLC using 10:90 MeOH:CH$_2$Cl$_2$ (starting material R$_f$=0.55 using UV and ninhydrin staining; product R$_f$=0.25 using UV and ninhydrin staining). The reaction can also be monitored and the product purity determined by HPLC using a Zorbax Bonus RP (5 μm) column (2.1 mm×50 mm) with a gradient of 2 to 50% acetonitrile/0.2% TFA in water/0.2% TFA over 5.0 min with a flow rate of 0.5 mL/min and detection by UV absorbency at 214 nm. Under these conditions, the starting material elutes at 3.0 min and the product elutes at 2.2 min.

Step 15

A mixture of compound J' (37.0 g, 110 mmol, 1.1 equiv), compound U (43.7 g, 100 mmol, 1.0 equiv) and diisopropylethylamine (20.0 mL, 129 mmol, 1.15 equiv) in acetonitrile (400 mL) was heated at 65° C. for 15 h. HPLC analysis indicated that the reaction was incomplete. An additional 3.5 g of compound J' was added and the reaction was allowed to proceed an addtional 15 h. HPLC analysis indicated that the reaction was complete. The solution was concentrated in vacuo to an oil and redissolved in ethyl acetate (600 mL). The ethyl acetate solution was washed with water (3×150 mL). The aqueous washes were combined and extracted with 100 mL ethyl acetate. The ethyl acetate phases were combined and extracted with portions of 1.0 N HCl (500 mL followed by 250 mL). The aqueous acid layers were combined and washed twice with 150 mL portions of ethyl acetate. The yellow acidic aqueous layer was treated with 29 g of activated carbon. The mixture was stirred vigorously for 30 min and then filtered. The colorless filtrate was treated with 1.0 N NaOH by dropwise addition until the pH had reached 4.5 and a milky suspension had formed. This suspension was extracted with 400 mL ethyl acetate. The aqueous layer was further treated by dropwise addition of 1.0 N NaOH until the pH reached 6.0. The resulting cloudy suspension was extracted with 250 mL ethyl acetate. The aqueous layer was further treated by dropwise addition of 1.0 N NaOH until the pH reached 8.5 and extracted with 250 mL ethyl acetate. These ethyl acetate layers (extracts of basic aqueous solution) were combined, dried over anhydrous magnesium sulfate ($MgSO_4$) (20 g), filtered through filter paper using a Buchner funnel and the residue thoroughly rinsed with ethyl acetate (100 mL). The filtrate was concentrated on a rotary evaporator to afford 62 g of compound 1 as pale yellow oil (84%), 94% pure by HPLC. This material was further purified by silica gel chromatography in two batches of approximately equal mass. For each batch, a Buchner funnel was filled with a slurry of silica gel in $CH_2Cl_2$ (400 mL). A solution of impure product in $CH_2Cl_2$ (25 mL) was loaded onto the plug and a vacuum was applied to draw the solution into the silica gel plug. The plug was washed with $CH_2Cl_2$ (1000 mL) and eluted with 99:1 $CH_2Cl_2$:MeOH (2000 ml) followed by 98:2 $CH_2Cl_2$:MeOH (2000 mL) using vacuum to pull solvent through the plug until all of the product had eluted. The pure fractions from both silica plugs were combined and concentrated to dryness on a rotary evaporator to afford 46.5 g (63%) of the product as a colorless oil, >99% pure by HPLC. MS M+H=737.7. During this procedure, the reaction was monitored by TLC using 90:10 $CH_2Cl_2$:MeOH with detection by UV absorbance (product $R_f$=0.60). The reaction can also be monitored and the product purity determined by HPLC using a Zorbax Bonus RP (5 μm) column (2.1 mm ×50 mm) with a gradient of 10 to 70% acetonitrile/0.2% TFA in water/0.2% TFA over 5.0 min with a flow rate of 0.5 mL/min and detection by UV absorbency at 214 nm. Under these conditions, the product elutes at 2.7 min and the starting materials elute at 3.4 min (J') and 1.3 min (U).

Alternatively, intermediate H can be prepared by the following procedure:

Step 1

2-Amino-3-methylbenzoic acid (100 g, 662 mmoles, 1.0 equiv.), glycine methyl ester hydrochloride (100 g, 797 mmoles, 1.2 equiv), and diisopropylethylamine (175 mL, 1000 mmoles, 1.5 equiv) were dissolved in acetonitrile (860 mL) and chilled to 0° C. 1-[3-(dimethyhlaminopropyl]-3-ethylcarbodiimide hydrochloride (141 g, 736 mmoles, 1.11 equiv.) was added in one portion. The reaction was stirred and allowed to warm slowly to room temperature. After 16 h, the reaction was concentrated in vacuo and diluted with ethyl acetate and washed with saturated aqueous ammonium chloride followed by saturated aqueous sodium chloride. Significant amounts of product remained in the aqueous layers. These were washed with additional portions of ethyl acetate. All ethyl acetate layers were combined, dried ($Na_2SO_4$) and concentrated. The product was recrystallized from ethyl acetate/hexanes to yield a first crop of 118 g (80%). Additional product present in the mother liquor was purified by silica gel chromatography to afford an addtional 5.0 g (4%). This reaction can be monitored by TLC using 50:50 ethyl acetate:hexanes with detection by UV absorbance (product $R_f$=0.46).

Step 2

N-(2-Amino-3-methylbenzoyl)glycine methyl ester (123 g, 554 mmol) was combined with morpholine (530 mL, 6070 mmol), the mixture was stirred at 130° C. for 16 h. Excess morpholine was removed under vacuum and the residue was treated with methanol to precipitate the product (ethyl acetate is also effective at precipitating the product). The precipitate was collected by filtration and dried to afford 68 g of compound H in good purity. The filtrate was concentrated and filtered through silica gel. Product was eluted with ethyl acetate and precipitated from the pure fractions.

This product was collected by filtration. The filtrate was concentrated and treated with methanol to precipitate additional product. The filtrate was again concentrated and treated with methanol to precipitate additional product. All crops of product were evaluated for purity and were found to be of excellent quality. All crops were combined to afford 102 g (67%) of compound H which was characterized by NMR. This reaction can be monitored by TLC using 90:10 $CH_2Cl_2$:MeOH (product $R_f$=0.55 using UV and ninhydrin staining).

Biological Examples

Assay Procedures

The compounds of Formula I were found to exhibit significant activity in the assays described below, and demonstrated improved properties when compared to conventional local anesthetics (i.e., lidocaine, bupivacaine).

Example 1

Whole-Cell Voltage Clamp

The whole cell variant of the patch-clamp method (*Hamill* et al., *Pflügers Arch.* 391:85–100, 1981) was used to measure $Na^+$ currents in $GH_3$ cells. The external solution contained (in mmol) 150 choline Cl, 0.2 $CdCl_2$, 2 $CaCl_2$, and 10 hydroxethylpiperazine ethane sulfonic acid (HEPES) adjusted to pH 7.4 with tetramethyl hydroxide. Micropipettes were fabricated and had a tip resistance of ~1 MΩ when filled with an Na+solution containing (in mmol) 100 NaF, 30 NaCl, 10 EGTA (ethylene glycol-bis(β-aminoethyl ether)-N,N,N',N'-tetraacetic acid), and 10 hydroxyethylpiperazineethane sulfonic acid, adjusted to pH 7.2 with CsOH.

The junction potential of electrodes was nulled before seal formation. After the rupture of the patch membrane, the cell was allowed to equilibrate with the pipette solution for at least 15 min at the holding potential of –100 mV. Under these reversed $Na^+$ gradient conditions, outward $Na^+$ currents were activated at approximately –30 mV. Test compounds, at appropriate concentrations, were applied to cells with a flow rate of about 0.12 mL/min via a series of narrow-bored capillary tubes positioned within 200 μm of the cell. Typically, the more soluble salt form, rather than the free base, was used. Washout of drugs was performed via a tube containing the external solution without drug present. Voltage-clamp protocols were created with pClamp software (Axon Instruments, Inc., Foster City, Calif.). Leak and capacitance were subtracted by a leak and capacity compensator (Hille and Campbell, *J. Gen. Physiol.* 67:265—93, 1976). Additional compensation was achieved by the patch clamp device (EPC7, List-Electronic, Darmstadt/Eberstadt, Germany). All experiments were performed at room temperature. At the end of the experiments, the drift in the junction potential was generally <2 mV.

Example 2

Rat Sciatic Nerve Sucrose-Gap Assay

Sprague-Dawley rats (42–56 days old) obtained from Charles River Laboratories were used in these experiments. Animals were euthanized and the sciatic nerves were excised and maintained in Ringer solution.

The Ringer solution contained: 124 mM NaCl, 3 mM KCl, 1.3 mM $NaH_2PO_4$, 2 mM $MgCl_2H_2O$, 2 mM $MgCl_2$–$6H_2O$, 26 mM $NaHCO_3$, and 10 mM Dextrose. The pH was adjusted to 7–7.5 using bubbled 95% $O_2$–5% $CO_2$ This Ringer solution was used for storing nerves and for filling the two stimulating pools (500 ul) and the recording "intracellular" pool.

The compounds to be tested for local anesthetic activity were prepared as 10 mM solutions in 15% PEG 400. The solutions were stored at 4° C. to minimize loss of potency. The working solutions were prepared by diluting stock solution in Ringer solution just prior to their use in experiments.

Segments of nerves measuring 5 mm were desheathed and mounted in a polycarbonate sucrose-gap chamber. In the chamber, the nerves were laid across a series of pools and within a cylindrical gap with the proximal end in the "test" pool. Petroleum jelly (Vaseline, Cheeseborough Pons) was used to create watertight seals around regions of the nerves passing between aqueous pools.

The proximal end of the nerve was stimulated by a pair of bipolar Ag/AgCl electrodes inserted into the stimulating pools. The "test" pool (500 μl volume) contained the Ag/AgCl electrode that recorded the extracellular electrical potential. Flowing at 1.0 mL/min, a nonionic sucrose solution (320 mM) prevented the action potential from propagating beyond the test pool. The intracellular potential, conducted passively through the sucrose gap to the distal end of the preparation, was recorded using Ag/AgCl ("intracellular") electrodes in a Ringers containing pool. Using a stimulator (A360 Stimulus Isolator, WPI), nerves were stimulated for 0.1 ms at two times the intensity required to induce the maximal compound action potential (CAP). The electrical signal from the nerve, the compound action potential (CAP) from large myelinated fibres, was amplified 10 times using an amplifier (IsoDam 8, WPI). The signal was displayed on an oscilloscope and also recorded on a computer using BioPak software. A nerve preparation was considered acceptable if the CAP measured not less than 10 mV, and the experiment was carried out after CAP stabilized (i.e. did not vary more than 1–2mV over a 10–20min period).

Nerves were stimulated at less than 1 Hz during the full experiment time to assess "tonic" block, and "phasic" block was measured by 50 Hz trains applied 400 ms every 4 secs. All the data was recorded at room temperature.

Example 3

Measurement of Sciatic Nerve Block in the Rat

Sprague-Dawley male rats in groups of 3–6 were injected percutaneously with a 27 G needle close to the sciatic nerve (about one third of the distance between the greater trochanter and the ischial tuberosity and caudal to the greater trochanter) with 0.2 mL of 10–90 mM solution of test compounds, pH 3–4.5 (i.e., compounds of Formula I, lidocaine and bupivacaine (Marcaine®)). Animals were observed at least three times on the day of the procedure, and each day thereafter.

At 3, 15 and 30 minutes and every 30 minutes thereafter for up to 10 hours after injection, the animals were assessed for motor and sensory nerve block. Where the anesthesia lasted longer than 10 hours, daily assessments were made for up to 5 days. Motor deficit was assessed by placing the animal on a flat surface and noting whether the paw is spread out under the animal (normal position) or whether it is kept closed and not used for locomotion (deficit). For assessment of sensory block, the animal was held above the bench surface and the skin between the two lateral-most toes was pinched using a pair of "rat-tooth forcepts". A withdrawal response is normal, whereas no response indicates sensory block.

In animals that showed full recovery of motor and sensory nerve function within 48 hours, a second compound is tested after a period of one week has elapsed. The tests are performed in the same way as described above, but on the contralateral limb. Results are analyzed for statistical significance using a one way analysis of variance.

Example 4

Use of a Compound of Formula I for Surgical Anesthesia and/or Post-operative Analgesia Compounds of Formula I are used in patients requiring both surgical anesthesia and post-operative analgesia (e.g., surgical repair of an inguinal hernia) or post-procedure pain relief only (e.g., post-operative pain relief of long duration; post-arthroscopy).

A patient requiring surgical repair of an inguinal hernia is prepared for surgery. It is desired to provide local anesthesia prior to incision, and for 18 to 36 hours post-operatively. Accordingly, prior to incision, a sterile injectable solution containing about 0. 1–2.5% of a compound of Formula I (with or without 5 ug/mL epinephrine, at the discretion of the surgeon) is infiltrated incrementally at the site of incision until the patient no longer senses cutaneous pain when pinched with a hemostat. Additional drug is administered during the procedure if required. The total volume of solution required is in the range of about 10–30 mL.

For post-operative analgesia in a patient requiring a major abdominal operation (e.g., a C-section), who will receive a general anesthetic during the operation, the wound area is infiltrated either pre-incisionally or at the end of the procedure with a compound of Formula I.

For relief of joint pain following an arthroscopic procedure, the patient's joint is infiltrated with a compound of Formula I.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

What is claimed is:

1. A compound of Formula (Ia):

(Ia)

wherein:
$R^1$ and $R^2$ are independently selected from the group consisting of hydrogen, alkyl, halo, cyano, hydroxy, alkoxy, amino, monosubstituted or disubstituted amino, carboxy, and alkoxycarbonyl;

$R^5$ and $R^6$ are independently selected from the group consisting of hydrogen and alkyl;

$R^7$ is alkyl, substituted alkyl, aryl, substituted aryl, heteroaryl, substituted heteroaryl, heterocycle, or substituted heterocycle;

$R^8$ and $R^9$ are independently selected from the group consisting of hydrogen, alkyl, substituted alkyl and —$NR^aR^b$— where $R^a$ and $R^b$ are alkyl; and Ar is selected from the group consisting of aryl, substituted aryl, heteroaryl, substituted heteroaryl, heterocycle, substituted heterocycle, cycloalkyl and substituted cycloalkyl; or a pharmaceutically acceptable salt thereof.

2. The compound of claim 1 wherein:
Ar is aryl or substituted aryl;
$R^1$, $R^2$, and $R^6$ are independently selected from hydrogen and alkyl;
$R^5$ is hydrogen; and
$R^8$ is hydrogen and $R^9$ is hydrogen or alkyl.

3. The compound of claim 2 wherein:
Ar is phenyl or phenyl substituted with one or two alkyl.

4. The compound of claim 3 wherein $R^7$ is 2-methoxyethyl, 2-morpholin-4-ylethyl, 2-N,N-dimethylaminoethyl, 2-N,N-diethylaminoethyl, 3-N,N-dimethyl-aminopropyl, 2-acetyl-aminoethyl, 2-[N,N-(2-acetyloxyethyl)amino]ethyl, 3-acetyloxy-2-hydroxypropyl, 2-hydroxyethyl, 3-hydroxypropyl, 2,3-dihydroxypropyl, 2-(imidazol-4-yl)ethyl, 2-(pyridin-3-yl)ethyl, 2-(indol-3-yl)ethyl, 2-(5-methoxyindol-3-yl)ethyl, 3-(imidazol-1-yl)ethyl, 3-(2-oxo-pyrrolidin-1-yl)propyl, 2-(2-oxoimidazolidin-1-yl)-ethyl, phenyl, morpholin-4-ylcarbonylmethyl, N,N-dimethylaminocarbonylmethyl, 2-(N,N-dimethylaminoethyl)carbonylmethyl, 2-N,N-(2-hydroxyethyl)aminoethyl, N,N-diethylaminocarbonylmethyl, piperidin-1-ylcarbonylmethyl, N,N-(2-methoxyethyl)-aminocarbonylmethyl, N-ethylamino-carbonylmethyl, N-(2-dimethyl-aminoethyl)-aminocarbonylmethyl, N-pyridin-3-ylaminocarbonylmethyl, 1-methylpiperazin-4-yl-carbonylmethyl, 4-oxopiperidin-1-ylcarbonylmethyl, 2-piperidin-1-ylethyl, 3-(4-methylpiperazin-1-yl)propyl, 2-pyrrolidin-1-ylethyl, 3-pyrrolidin-1-ylpropyl, 2-N,N-dimethylaminoethyl, N-tetrahydropyran-4-ylaminocarbonylmethyl, N-pyridin-3-ylaminocarbonylmethyl, benzoylmethyl, 4-methoxybenzoylmethyl, benzyloxycarbonyl-methyl, benzyl, pyridin-2-ylmethyl, pyridin-3-ylmethyl, pyridin-4-ylmethyl, 5-methylpyrazin-2-ylmethyl, or furan-2-ylmethyl.

5. The compound of claim 4 wherein $R^7$ is morpholin-4-ylcarbonylmethyl, phenyl, pyridin-3-ylmethyl, pyridin-4-ylmethyl, N-ethylaminocarbonylmethyl, 2-(imidazol-4-yl)ethyl, furan-2-ylmethyl, or 2-(indol-3-yl)ethyl.

6. The compound of claim 1 wherein:
$R^5$ is hydrogen; and $R^6$ is hydrogen or alkyl;
Ar is aryl or substituted aryl; and
$R^8$ is hydrogen and $R^9$ is hydrogen or alkyl.

7. The compound of claim 1 wherein:
$R^1$ and $R^2$ are independently selected from the group consisting of hydrogen, methyl, ethyl, n-propyl, 2-propyl, chloro, fluoro, cyano, hydroxy, methoxy, ethoxy, n-propoxy, 2-propoxy, amino, methylamino, or dimethylamino;

$R^5$ and $R^6$ are independently selected from the group consisting of hydrogen and alkyl; and Ar is 2-methylphenyl, 2,6-dimethylphenyl, 2-isopropylphenyl, 2,6-dimethyl-phenyl, or 2,4,6-trimethylphenyl.

8. The compound of claim wherein:
$R^7$ is 2-methoxyethyl, 2-morpholin-4-ylethyl, 2-N,N-dimethylaminoethyl, 2-N,N-diethylam inoethyl, 3-N,N-dimethylam inopropyl, 2-acetyl-aminoethyl, 2-[N,N-(2-acetyloxyethyl)aminoethyl, 3-acetyloxy-2-hydroxypropyl, 2-hydroxyethyl, 3-hydroxypropyl, 2,3-dihydroxypropyl, 2-(imidazol-4-yl)ethyl, 2-(pyridin-3-yl)ethyl, 2-(indol-3-yl)ethyl, 2-oxoimadazolidin-1-yl) ethyl, phenyl, morpholin-4-yl-carbonylmethyl, N,N-dimethylaminocarbonylmethyl, 2-(N,N-dimethyl-aminoethyl)carbonylmethyl, 2-N,N-(2-hydroxyethyl) aminoethyl,N,N-diethylaminoacarbonylmethyl, piperidin-1-ylcarbonylmethyl, N,N-(2-methoxy-ethyl)-aminocarbonylmethyl, N-ethylamino-carbonylmethyl, N-(2-dimethyl-aminoethyl)aminoacarbonylmethyl, N-pyridin-3-ylam inocarbonylmethyl, 1-methylpiperazin-4-ylcaronylmethyl, 4-oxopiperidin-1-ylcarbonylmethyl, 2-piperidin-1-ylethyl, 3-(4-methylpiperazin-1-yl)propyl, 2-pyrrolidin-1-ylethyl, 3-pyrrolidin-1-ylpropyl, 2-N,N-dimethylaminoethyl, N-tetrahydropyran4-yl-aminocarbonylmethyl, N-pyridin-3-ylamino-carbonylmethyl, benzoylmethyl, 4-methoxybenzoylmethyl, benzyloxycarbonyl-methyl, benzyl, pyridin-2-ylmethyl, pyridin-3-ylmethyl, pyridin4-ylmethyl, 5-methylpyrazin-2-ylmethyl, furan-2-ylmethyl; and Ar—W— is 2-methylphenyl-NH—C(O)—*CH(CH$_2$CH$_3$), 2-isopropylphenyl-NH—C(O)—CH$_2$—, 2,6-dimethylphenyl-NH—C(O)—*CH(CH$_2$CH$_3$)-2,4, 6-trimethylphenyl-NH—C(O)—CH$_2$— or 2-ethylphenyl-NH—C(O)*CH(CH$_2$CH$_3$)— wherein the stereochemistry at *C is (S), (R), or 9. The compound of claim 7 wherein:

$R^1$, $R^5$ and $R^6$ are hydrogen;

$R^2$ is methyl and is located at the C-8 position of the quinazolin-4-one ring;

$R^7$ is morpholin-4-ylcarbonylmethyl, phenyl, pyridin-3-ylmethyl, pyridin-4-ylmethyl, N-ethylaminocarbonylmethyl, 2-(imidazol-4-yl)ethyl, furan-2-ylmethyl, or 2-(indol-3-yl)ethyl.

10. The compound of claim 9 wherein:

$R^7$ is morpholin-4-ylcarbonylmethyl; and

Ar—W— is 2-methylphenyl-NH—C(O)—*CH(CH$_2$CH$_3$)— wherein the stereochemistry at *C is (S), (R), or (RS).

11. The compound of claim 1 wherein $R^7$ is morpholin-4-ylcarbonylmethyl, phenyl, pyridin-3-ylmethyl, pyridin-4-ylmethyl, N-ethylaminocarbonylmethyl, 2-(imidazol-4-yl)ethyl, furan-2-ylmethyl, or 2-(indol-3-yl)ethyl.

12. A pharmaceutical composition comprising a pharmaceutically acceptable excipient and a therapeutically effective amount of a compound of any of claims 1–11.

13. A method for producing local anesthesia in a mammal, which method comprises administering to a mammal in need of such treatment a pharmaceutical composition comprising a pharmaceutically acceptable excipient and a therapeutically effective amount of a compound of any of claims 1–11.

* * * * *

UNITED STATES PATENT AND TRADEMARK OFFICE
CERTIFICATE OF CORRECTION

PATENT NO. : 6,436,919 B1
DATED : August 20, 2002
INVENTOR(S) : Sabine Axt et al.

It is certified that error appears in the above-identified patent and that said Letters Patent is hereby corrected as shown below:

Column 69,
Line 40, "Rb" should read -- $R^b$ --.

Column 70,
Line 36, after "claim", insert -- 1 --.
Line 43, after "2-(indol-3-yl)ethyl," insert -- 2-(5-methoxyindol-3-yl)ethyl, 3-(imidazol-1-yl)ethyl, 3-(2-oxo-pyrrolidin-1-yl)propyl, 2-( --.
Line 47, "N,N-diethylaminoacarbonylmethyl" should read -- N,N-diethylaminocarbonylmethyl --.
Line 50, "N-(2-dimethyl-aminoethyl)aminoacarbonylmethyl," should read -- N-(2-dimethylaminoethyl)aminocarbonylmethyl, --.
Line 52, "1-methylpiperazin-4-ylcaronylmethyl," should read -- 1-methylpiperazin-4-ylcarbonylmethyl, --.
Line 56, "N-tetrahydropyran4-yl-aminocarbonylmethyl," should read -- N-tetrahydropyran-4-yl-aminocarbonylmethyl, --.
Line 60, "pyridin4-ylmethyl," should read -- pyridin-4-ylmethyl, --.
Line 67, after "or", insert -- (RS). --.

Signed and Sealed this

Fourth Day of April, 2006

JON W. DUDAS
*Director of the United States Patent and Trademark Office*